United States Patent
Ehrlich

(10) Patent No.: US 11,977,085 B1
(45) Date of Patent: May 7, 2024

(54) DATE RAPE DRUG DETECTION DEVICE AND METHOD OF USING SAME

(71) Applicant: Elan Ehrlich, Tel-Aviv (IL)

(72) Inventor: Elan Ehrlich, Tel-Aviv (IL)

( * ) Notice: Subject to any disclaimer, the term of this patent is extended or adjusted under 35 U.S.C. 154(b) by 0 days.

(21) Appl. No.: 18/242,561

(22) Filed: Sep. 6, 2023

Related U.S. Application Data

(60) Provisional application No. 63/536,524, filed on Sep. 5, 2023.

(51) Int. Cl.
   *G01N 33/94* (2006.01)
   *G01N 21/78* (2006.01)
   *G01N 33/52* (2006.01)

(52) U.S. Cl.
   CPC ............. *G01N 33/94* (2013.01); *G01N 21/78* (2013.01); *G01N 33/528* (2013.01)

(58) Field of Classification Search
   CPC ....... G01N 33/94; G01N 21/78; G01N 33/528
   See application file for complete search history.

(56) References Cited

U.S. PATENT DOCUMENTS

| | | |
|---|---|---|
| 4,939,705 A | 7/1990 | Hamilton et al. |
| 5,399,581 A | 3/1995 | Laragh |
| 5,605,911 A | 2/1997 | Olney et al. |
| 6,150,353 A | 11/2000 | Broekkamp et al. |
| 6,156,742 A | 12/2000 | Mackenzie |
| 6,300,332 B1 | 10/2001 | Chang et al. |
| 6,468,504 B1 | 10/2002 | Richards et al. |
| 6,482,426 B1 | 11/2002 | Podolski |
| 6,620,626 B1 | 9/2003 | Bodily |
| 6,663,846 B1 | 12/2003 | McCombs et al. |
| 7,034,036 B2 | 4/2006 | Schoenhard |

(Continued)

FOREIGN PATENT DOCUMENTS

| | | |
|---|---|---|
| AU | 2002342707 | 6/2003 |
| AU | 2011218662 | 1/2013 |

(Continued)

OTHER PUBLICATIONS

"G-Check Date Rape Drug Detection Sticker", from https://metro-spy-supply.com/products/is-your-drink-safe-date-rape-drug-detection-sticker, webarchive Aug. 8, 2022, pp. 1-8, hereinafter referred to as "G-Check"). (Year: 2022 ).*

(Continued)

*Primary Examiner* — Dennis White

(57) ABSTRACT

The present invention relates to devices and methods for detecting date rape drugs (DRDs) in beverages during social events. The device includes a cellphone, and further includes one or more protective covers, screen cover, stylus, or other add-ons, either individually or in combination. The device incorporates a user-friendly DRD detection system physically attached or integrated with the cellphone or any one of its accessories, ensuring uninterrupted use of the device's primary functions, wherein this physical attachment and/or integration minimizes the likelihood of users forgetting the device elsewhere and/or removing the DRD detection system, thus ensuring its immediate availability when needed. The DRD detection system's operation does not significantly impact the regular use of the cellphone or its accessories, maintaining convenience and safety in social settings.

12 Claims, 20 Drawing Sheets

(56) References Cited

U.S. PATENT DOCUMENTS

| | | |
|---|---|---|
| 7,374,946 B2 | 5/2008 | Glattstein |
| 7,915,285 B2 | 3/2011 | Johnson et al. |
| 7,995,203 B2 | 8/2011 | Babichenko et al. |
| 8,071,075 B2 | 12/2011 | Reed et al. |
| 8,138,169 B2 | 3/2012 | Oronsky et al. |
| 8,231,915 B2 | 7/2012 | Davis |
| 8,334,263 B2 | 12/2012 | Nadeson et al. |
| 8,404,488 B2 | 3/2013 | Babichenko et al. |
| 8,410,064 B2 | 4/2013 | Radominska-Pandya et al. |
| 8,461,146 B2 | 6/2013 | Seol et al. |
| 8,703,099 B2 | 4/2014 | Reis et al. |
| 8,883,817 B2 | 11/2014 | Sadée et al. |
| 8,889,707 B2 | 11/2014 | Cohen-Armon et al. |
| 8,958,112 B2 | 2/2015 | Matsui et al. |
| 8,975,268 B2 | 3/2015 | Berde et al. |
| 8,987,304 B2 | 3/2015 | Matsumoto et al. |
| 9,085,793 B2 | 7/2015 | Parkinson |
| 9,228,991 B2 | 1/2016 | Patolsky et al. |
| D750,988 S | 3/2016 | Goldring |
| D751,435 S | 3/2016 | Goldring |
| 9,291,504 B2 | 3/2016 | Goldring et al. |
| 9,377,396 B2 | 6/2016 | Goldring et al. |
| 9,383,258 B2 | 7/2016 | Goldring et al. |
| 9,448,114 B2 | 9/2016 | Goldring et al. |
| 9,492,541 B2 | 11/2016 | Srinivasan et al. |
| 9,500,523 B2 | 11/2016 | Goldring et al. |
| 9,517,254 B2 | 12/2016 | Sitchon et al. |
| 9,562,848 B2 | 2/2017 | Goldring et al. |
| 9,574,942 B2 | 2/2017 | Goldring et al. |
| 9,587,982 B2 | 3/2017 | Goldring et al. |
| 9,597,335 B2 | 3/2017 | Tuiten et al. |
| 9,642,563 B2 | 5/2017 | Crawford et al. |
| 9,701,645 B2 | 7/2017 | Chang et al. |
| 9,933,305 B2 | 4/2018 | Goldring et al. |
| 9,939,318 B2 | 4/2018 | Goldring et al. |
| 9,952,098 B2 | 4/2018 | Goldring et al. |
| 10,066,990 B2 | 9/2018 | Rosen et al. |
| 10,203,246 B2 | 2/2019 | Rosen et al. |
| 10,254,215 B2 | 4/2019 | Wilk et al. |
| 10,274,475 B2 | 4/2019 | Abramson et al. |
| 10,323,982 B2 | 6/2019 | Goldring et al. |
| 10,330,531 B2 | 6/2019 | Goldring et al. |
| 10,502,679 B2 | 12/2019 | Aphek |
| 10,625,063 B2 | 4/2020 | Altschul et al. |
| 10,641,657 B2 | 5/2020 | Goldring et al. |
| 10,648,861 B2 | 5/2020 | Goldring et al. |
| 10,704,954 B2 | 7/2020 | Goldring et al. |
| 10,751,300 B2 | 8/2020 | Mukunda et al. |
| 10,753,952 B2 | 8/2020 | Reisinger |
| 10,760,964 B2 | 9/2020 | Goldring et al. |
| 10,791,933 B2 | 10/2020 | Goldring et al. |
| 10,793,644 B2 | 10/2020 | Hryhorenko et al. |
| 10,799,467 B2 | 10/2020 | Whalley |
| 10,842,434 B2 | 11/2020 | Macchi |
| 10,942,065 B2 | 3/2021 | Goldring et al. |
| 11,067,443 B2 | 7/2021 | Goldring et al. |
| 11,118,971 B2 | 9/2021 | Goldring et al. |
| 11,207,322 B2 | 12/2021 | France et al. |
| 11,237,050 B2 | 2/2022 | Goldring et al. |
| 11,320,307 B2 | 5/2022 | Goldring et al. |
| 11,333,552 B2 | 5/2022 | Goldring et al. |
| 11,378,449 B2 | 7/2022 | Milo et al. |
| 11,609,119 B2 | 3/2023 | Goldring et al. |
| 11,624,651 B2 | 4/2023 | Goldring et al. |
| 11,761,898 B2 | 9/2023 | Lee et al. |
| 2001/0001144 A1 | 5/2001 | Kapp |
| 2001/0046710 A1 | 11/2001 | Cutler |
| 2001/0053798 A1 | 12/2001 | Disanto |
| 2002/0090620 A1 | 7/2002 | Davis et al. |
| 2003/0004176 A1 | 1/2003 | Dewey et al. |
| 2003/0013689 A1 | 1/2003 | Helton et al. |
| 2003/0072800 A1 | 4/2003 | Singh et al. |
| 2003/0092706 A1 | 5/2003 | Barsig |
| 2003/0109546 A1 | 6/2003 | Fenton |
| 2003/0114469 A1 | 6/2003 | Cohen |
| 2003/0144220 A1 | 7/2003 | Obach |
| 2003/0224435 A1 | 12/2003 | Seiwert |
| 2004/0024006 A1 | 2/2004 | Simon |
| 2004/0044005 A1 | 3/2004 | Cary |
| 2004/0087484 A1 | 5/2004 | Sahota |
| 2004/0117205 A1 | 6/2004 | Reardan et al. |
| 2004/0213744 A1 | 10/2004 | Lulla et al. |
| 2005/0004106 A1 | 1/2005 | Romano |
| 2005/0038062 A1 | 2/2005 | Burns et al. |
| 2005/0048663 A1 | 3/2005 | Novinski et al. |
| 2005/0065158 A1 | 3/2005 | Naylor et al. |
| 2005/0215567 A1 | 9/2005 | Bakker et al. |
| 2005/0220715 A1 | 10/2005 | Lin |
| 2005/0233459 A1 | 10/2005 | Melker et al. |
| 2006/0009478 A1 | 1/2006 | Friedmann et al. |
| 2006/0128676 A1 | 6/2006 | Shafer et al. |
| 2006/0190419 A1 | 8/2006 | Bunn et al. |
| 2006/0217394 A1 | 9/2006 | Nathanson et al. |
| 2006/0240128 A1 | 10/2006 | Schlagheck |
| 2006/0252749 A1 | 11/2006 | Stohr |
| 2007/0082873 A1 | 4/2007 | Lingenhöhl et al. |
| 2007/0161063 A1 | 7/2007 | Love et al. |
| 2007/0197543 A1 | 8/2007 | Esteve-Soler et al. |
| 2008/0009538 A1 | 1/2008 | Skolnick |
| 2008/0090301 A1 | 4/2008 | Smith |
| 2008/0095718 A1 | 4/2008 | Rubsamen et al. |
| 2008/0103155 A1 | 5/2008 | Mendla et al. |
| 2008/0128482 A1 | 6/2008 | Chen et al. |
| 2008/0181876 A1 | 7/2008 | Johnson et al. |
| 2008/0206310 A1 | 8/2008 | Davis |
| 2008/0248470 A1 | 10/2008 | Kim et al. |
| 2008/0255093 A1 | 10/2008 | Tam et al. |
| 2008/0261991 A1 | 10/2008 | Bar-Or et al. |
| 2009/0023712 A1 | 1/2009 | Ferger et al. |
| 2009/0023744 A1 | 1/2009 | Fava |
| 2009/0137662 A1 | 5/2009 | Gordon et al. |
| 2009/0239881 A1 | 9/2009 | Becker |
| 2010/0016294 A1 | 1/2010 | Cartt |
| 2010/0041689 A1 | 2/2010 | Johnson et al. |
| 2010/0135907 A1 | 6/2010 | Cranley et al. |
| 2010/0210732 A1 | 8/2010 | Babul |
| 2010/0227854 A1 | 9/2010 | Tananbaum et al. |
| 2010/0267736 A1 | 10/2010 | Thomas |
| 2010/0291242 A1 | 11/2010 | Sugimoto et al. |
| 2010/0311717 A1 | 12/2010 | McIntosh et al. |
| 2010/0311785 A1 | 12/2010 | Podolski |
| 2011/0014127 A1 | 1/2011 | Schachtel |
| 2011/0038958 A1 | 2/2011 | Kikuchi et al. |
| 2011/0065628 A1 | 3/2011 | Johnson et al. |
| 2011/0086428 A1 | 4/2011 | Larson et al. |
| 2011/0165262 A1 | 7/2011 | Al-Sari et al. |
| 2011/0198492 A1 | 8/2011 | Black |
| 2012/0070901 A1 | 3/2012 | Bradley et al. |
| 2012/0128733 A1 | 5/2012 | Perrin et al. |
| 2012/0202796 A1 | 8/2012 | Scheel-Krüger et al. |
| 2012/0232066 A1 | 9/2012 | Jenkins et al. |
| 2012/0289515 A1 | 11/2012 | Migaly |
| 2012/0295362 A1 | 11/2012 | Bland |
| 2012/0328602 A1 | 12/2012 | Salvemini |
| 2013/0006068 A1 | 1/2013 | Gemer et al. |
| 2013/0109655 A1 | 5/2013 | Gargaun et al. |
| 2013/0109712 A1 | 5/2013 | Solinas et al. |
| 2013/0209325 A1 | 8/2013 | Harooni |
| 2014/0107104 A1 | 4/2014 | Nishi et al. |
| 2014/0127300 A1 | 5/2014 | Tengler et al. |
| 2014/0274764 A1 | 9/2014 | Zhu et al. |
| 2014/0297306 A1 | 10/2014 | Whiddon et al. |
| 2014/0320858 A1 | 10/2014 | Goldring et al. |
| 2015/0025101 A1 | 1/2015 | Kaiko et al. |
| 2015/0119467 A1 | 4/2015 | Himes et al. |
| 2015/0154377 A1 | 6/2015 | Aull et al. |
| 2015/0157627 A1 | 6/2015 | Boeck |
| 2015/0164835 A1 | 6/2015 | King et al. |
| 2015/0185192 A1* | 7/2015 | Holmes .......... G01N 31/22 |
| | | 73/865.7 |
| 2015/0233762 A1 | 8/2015 | Goldring et al. |
| 2015/0292948 A1 | 10/2015 | Goldring et al. |
| 2015/0300879 A1 | 10/2015 | Goldring et al. |
| 2015/0355024 A1 | 12/2015 | Goldring et al. |

(56) References Cited

U.S. PATENT DOCUMENTS

| | | |
|---|---|---|
| 2015/0359458 A1* | 12/2015 | Erickson .................. G06T 7/90 382/133 |
| 2016/0003857 A1 | 1/2016 | Bennett |
| 2016/0055317 A1 | 2/2016 | Levine et al. |
| 2016/0061807 A1 | 3/2016 | Ravishankar et al. |
| 2016/0146726 A1* | 5/2016 | Aggarwal .............. G01N 21/31 250/226 |
| 2016/0238449 A1 | 8/2016 | Goldring et al. |
| 2016/0290863 A1 | 10/2016 | Goldring et al. |
| 2016/0299061 A1 | 10/2016 | Goldring et al. |
| 2017/0007502 A1 | 1/2017 | Teshima et al. |
| 2017/0010160 A1 | 1/2017 | Rosen et al. |
| 2017/0079574 A1 | 3/2017 | Rodriguez Restrepo et al. |
| 2017/0153142 A1 | 6/2017 | Rosen et al. |
| 2017/0153185 A1* | 6/2017 | Kisner ...................... G06T 7/90 |
| 2017/0160131 A1 | 6/2017 | Goldring et al. |
| 2017/0234729 A1 | 8/2017 | Goldring et al. |
| 2017/0254701 A1 | 9/2017 | Goldring et al. |
| 2017/0258791 A1 | 9/2017 | Miyata |
| 2017/0281652 A1 | 10/2017 | Altschul et al. |
| 2017/0292908 A1 | 10/2017 | Wilk et al. |
| 2018/0003558 A1 | 1/2018 | Goldring et al. |
| 2018/0015270 A1 | 1/2018 | De Laat et al. |
| 2018/0031468 A1 | 2/2018 | Aphek |
| 2018/0085003 A1 | 3/2018 | Goldring et al. |
| 2018/0120155 A1 | 5/2018 | Rosen et al. |
| 2018/0136042 A1 | 5/2018 | Goldring et al. |
| 2018/0143073 A1 | 5/2018 | Goldring et al. |
| 2018/0172510 A1 | 6/2018 | Rosen et al. |
| 2018/0180478 A1 | 6/2018 | Goldring et al. |
| 2018/0180481 A1 | 6/2018 | Goldring et al. |
| 2018/0184972 A1 | 7/2018 | Carmi et al. |
| 2018/0188110 A1 | 7/2018 | Goldring et al. |
| 2018/0238735 A1 | 8/2018 | Rosen et al. |
| 2018/0250585 A1 | 9/2018 | Weissman et al. |
| 2018/0252580 A2 | 9/2018 | Goldring et al. |
| 2018/0321212 A1 | 11/2018 | Letourneau et al. |
| 2018/0353449 A1 | 12/2018 | Yong |
| 2019/0011313 A1 | 1/2019 | Goldring et al. |
| 2019/0033130 A1 | 1/2019 | Goldring et al. |
| 2019/0033132 A1 | 1/2019 | Goldring et al. |
| 2019/0041265 A1 | 2/2019 | Rosen et al. |
| 2019/0056315 A1 | 2/2019 | Kinrot et al. |
| 2019/0388431 A2 | 7/2019 | Kelley, II et al. |
| 2019/0285471 A1 | 9/2019 | Milo et al. |
| 2019/0310134 A1 | 10/2019 | Goldring et al. |
| 2020/0033579 A1* | 1/2020 | Chou ............... G01N 33/54386 |
| 2020/0049555 A1 | 2/2020 | Goldring et al. |
| 2020/0088573 A1 | 3/2020 | Goldring et al. |
| 2020/0113515 A1 | 4/2020 | O'Connor et al. |
| 2020/0116564 A1 | 4/2020 | Goldring et al. |
| 2020/0138771 A1 | 5/2020 | Velasco Diez et al. |
| 2020/0197928 A1 | 6/2020 | Letourneau et al. |
| 2020/0209060 A1 | 7/2020 | Rosen et al. |
| 2020/0253970 A1 | 8/2020 | Cincotta |
| 2020/0292385 A1 | 9/2020 | Goldring et al. |
| 2020/0352901 A1 | 11/2020 | Raber et al. |
| 2020/0368227 A1 | 11/2020 | Maeda et al. |
| 2020/0393297 A1 | 12/2020 | Goldring et al. |
| 2021/0025753 A1 | 1/2021 | Goldring et al. |
| 2021/0069151 A1 | 3/2021 | Del Carmen Garcia Armenta |
| 2021/0116300 A1 | 4/2021 | Goldring et al. |
| 2021/0205296 A1 | 7/2021 | Sadee et al. |
| 2021/0241874 A1 | 8/2021 | Alcorn et al. |
| 2021/0302232 A1 | 9/2021 | Goldring et al. |
| 2021/0310934 A1 | 10/2021 | Heiman et al. |
| 2021/0330516 A1 | 10/2021 | Letourneau et al. |
| 2022/0000861 A1 | 1/2022 | Hirose et al. |
| 2022/0011162 A1 | 1/2022 | Goldring et al. |
| 2022/0064172 A1 | 3/2022 | Zhang et al. |
| 2022/0074791 A1 | 3/2022 | Goldring et al. |
| 2022/0156864 A1 | 5/2022 | Furman et al. |
| 2022/0193091 A1 | 6/2022 | Jahan Panah |
| 2022/0241268 A1 | 8/2022 | Pergolizzi |
| 2022/0257548 A1 | 8/2022 | Rubin |
| 2022/0265641 A1 | 8/2022 | Waldinger et al. |
| 2022/0357201 A1 | 11/2022 | Milo et al. |
| 2023/0022446 A1 | 1/2023 | Molina |
| 2023/0042725 A1 | 2/2023 | Anselmi et al. |
| 2023/0053938 A1 | 2/2023 | Khalili Moghaddam et al. |
| 2023/0221179 A1 | 7/2023 | Goldring et al. |
| 2023/0243742 A1 | 8/2023 | Kinrot et al. |

FOREIGN PATENT DOCUMENTS

| | | |
|---|---|---|
| AU | 2012330761 | 1/2016 |
| BR | 112021006788 | 7/2021 |
| BR | 112022020583 | 11/2022 |
| CA | 3104072 | 7/2022 |
| CN | 104040309 | 9/2014 |
| CN | 105593651 | 5/2016 |
| CN | 106461461 | 2/2017 |
| CN | 107250739 | 10/2017 |
| CN | 110179988 | 8/2019 |
| CN | 107741464 | 12/2020 |
| CN | 113167648 | 7/2021 |
| CN | 114569587 | 6/2022 |
| CN | 114767682 | 7/2022 |
| CN | 115337631 | 11/2022 |
| CN | 115343426 | 11/2022 |
| CN | 113727733 | 1/2023 |
| CN | 115836192 | 3/2023 |
| EP | 0173145 | 3/1986 |
| EP | 0546676 | 6/1993 |
| EP | 0980245 | 2/2000 |
| EP | 0641565 | 3/2000 |
| EP | 0925056 | 12/2000 |
| EP | 1156855 | 11/2001 |
| EP | 0845989 | 3/2002 |
| EP | 0995441 | 7/2002 |
| EP | 1069915 | 6/2003 |
| EP | 1336608 | 8/2003 |
| EP | 1348443 | 10/2003 |
| EP | 1352659 | 10/2003 |
| EP | 1370662 | 12/2003 |
| EP | 1058559 | 5/2004 |
| EP | 1476155 | 11/2004 |
| EP | 1210118 | 12/2004 |
| EP | 1100959 | 3/2005 |
| EP | 1511384 | 3/2005 |
| EP | 0942752 | 4/2005 |
| EP | 1202722 | 7/2005 |
| EP | 1550441 | 7/2005 |
| EP | 1557165 | 7/2005 |
| EP | 1581634 | 10/2005 |
| EP | 1307202 | 5/2006 |
| EP | 1683522 | 7/2006 |
| EP | 1714145 | 10/2006 |
| EP | 1725237 | 11/2006 |
| EP | 0615749 | 12/2006 |
| EP | 1345608 | 4/2007 |
| EP | 1807102 | 7/2007 |
| EP | 1750765 | 9/2007 |
| EP | 0983514 | 12/2007 |
| EP | 1556058 | 12/2007 |
| EP | 1881832 | 1/2008 |
| EP | 2036550 | 3/2009 |
| EP | 1220689 | 7/2009 |
| EP | 2079453 | 7/2009 |
| EP | 2083077 | 7/2009 |
| EP | 2089022 | 8/2009 |
| EP | 2333108 | 6/2011 |
| EP | 2363397 | 9/2011 |
| EP | 2428207 | 3/2012 |
| EP | 2429514 | 3/2012 |
| EP | 2012773 | 6/2012 |
| EP | 2381940 | 12/2012 |
| EP | 2340022 | 11/2013 |
| EP | 2705840 | 3/2014 |
| EP | 2774613 | 9/2014 |
| EP | 2783193 | 10/2014 |
| EP | 2211860 | 4/2015 |
| EP | 2857017 | 4/2015 |
| EP | 2881912 | 6/2015 |

(56) References Cited

FOREIGN PATENT DOCUMENTS

| | | |
|---|---|---|
| EP | 2891491 | 7/2015 |
| EP | 2702060 | 12/2015 |
| EP | 2117554 | 7/2016 |
| EP | 3072516 | 9/2016 |
| EP | 2217926 | 10/2016 |
| EP | 3090239 | 11/2016 |
| EP | 2723888 | 1/2017 |
| EP | 3164693 | 5/2017 |
| EP | 3209983 | 8/2017 |
| EP | 3213748 | 9/2017 |
| EP | 3246047 | 11/2017 |
| EP | 3290038 | 3/2018 |
| EP | 3294313 | 3/2018 |
| EP | 3308785 | 4/2018 |
| EP | 3332780 | 6/2018 |
| EP | 3340984 | 7/2018 |
| EP | 3391886 | 10/2018 |
| EP | 3395366 | 10/2018 |
| EP | 3280330 | 1/2019 |
| EP | 3436001 | 2/2019 |
| EP | 3488204 | 5/2019 |
| EP | 3553871 | 9/2019 |
| EP | 2968775 | 10/2019 |
| EP | 3562477 | 11/2019 |
| EP | 3298006 | 1/2020 |
| EP | 3334422 | 7/2020 |
| EP | 3720844 | 10/2020 |
| EP | 3813906 | 5/2021 |
| EP | 3848032 | 7/2021 |
| EP | 3864384 | 8/2021 |
| EP | 3864668 | 8/2021 |
| EP | 3288918 | 10/2021 |
| EP | 3888641 | 10/2021 |
| EP | 3028020 | 11/2021 |
| EP | 3938531 | 1/2022 |
| EP | 4006542 | 6/2022 |
| EP | 4133243 | 2/2023 |
| EP | 3166491 | 8/2023 |
| EP | 3773654 | 9/2023 |
| GB | 0329424 | 1/2004 |
| GB | 2416349 | 1/2006 |
| GB | 2418248 | 3/2006 |
| GB | 2425350 | 10/2006 |
| GB | 2510777 | 8/2014 |
| GB | 2529070 | 2/2016 |
| GB | 2543655 | 7/2023 |
| IL | 243881 | 7/2016 |
| IL | 246597 | 12/2016 |
| IL | 204157 | 5/2017 |
| IN | 235672 | 3/2007 |
| IN | 201611025138 | 3/2018 |
| IN | 201731045680 | 6/2019 |
| IN | 202041016778 | 5/2020 |
| IN | 202047053511 | 12/2020 |
| JP | 2014-532873 | 12/2014 |
| JP | 2016-528496 | 9/2016 |
| JP | 2017-505901 | 2/2017 |
| JP | 2019-056709 | 4/2019 |
| NZ | 260896 | 7/1997 |
| SG | 11201509855 | 6/2017 |
| SG | 11201509932X | 1/2018 |
| SI | 1225881 | 6/2006 |
| TW | I750590 | 12/2021 |
| WO | WO 98/50039 | 11/1998 |
| WO | WO 00/006160 | 2/2000 |
| WO | WO 00/51685 | 9/2000 |
| WO | WO 01/17521 | 3/2001 |
| WO | WO 01/051638 | 7/2001 |
| WO | WO 01/038566 | 11/2001 |
| WO | WO 01/055692 | 3/2002 |
| WO | WO 02/46426 | 6/2002 |
| WO | WO 02/051442 | 7/2002 |
| WO | WO 03/015820 | 2/2003 |
| WO | WO 03/061594 | 7/2003 |
| WO | WO 03/063844 | 8/2003 |
| WO | WO 03/075958 | 9/2003 |
| WO | WO 03/099010 | 12/2003 |
| WO | WO 2004/000354 | 12/2003 |
| WO | WO 2004/053099 | 6/2004 |
| WO | WO 2004/103359 | 12/2004 |
| WO | WO 2004/109279 | 12/2004 |
| WO | WO 2005/059541 | 6/2005 |
| WO | WO 2005/089486 | 9/2005 |
| WO | WO 2005/102390 | 11/2005 |
| WO | WO 2005/107741 | 11/2005 |
| WO | WO 2005/121793 | 12/2005 |
| WO | WO 2006/119958 | 1/2006 |
| WO | WO 2006/022428 | 3/2006 |
| WO | WO 2006/049933 | 5/2006 |
| WO | WO 2006/054513 | 5/2006 |
| WO | WO 2006/125042 | 11/2006 |
| WO | WO 2007/093587 | 8/2007 |
| WO | WO 2007/128442 | 11/2007 |
| WO | WO 2008/037045 | 4/2008 |
| WO | WO 2008/041751 | 4/2008 |
| WO | WO 2008/045060 | 4/2008 |
| WO | WO 2008/070268 | 6/2008 |
| WO | WO 2009/015244 | 1/2009 |
| WO | WO 2009/015734 | 2/2009 |
| WO | WO 2009/026660 | 3/2009 |
| WO | WO 2009/090556 | 7/2009 |
| WO | WO 2009/114139 | 9/2009 |
| WO | WO 2010/038874 | 4/2010 |
| WO | WO 2010/060742 | 6/2010 |
| WO | WO 2010/062900 | 6/2010 |
| WO | WO 2010/132521 | 11/2010 |
| WO | WO 2011/060026 | 5/2011 |
| WO | WO 2011/073981 | 6/2011 |
| WO | WO 2013/065035 | 5/2013 |
| WO | WO 2014/128882 | 8/2014 |
| WO | WO 2014/145829 | 9/2014 |
| WO | WO 2015/000032 | 1/2015 |
| WO | WO 2015/000033 | 1/2015 |
| WO | WO 2015/015493 | 2/2015 |
| WO | WO 2015/101992 | 7/2015 |
| WO | WO 2015/150069 | 10/2015 |
| WO | WO 2016/059403 | 4/2016 |
| WO | WO 2016/063284 | 4/2016 |
| WO | WO 2016/63284 | 4/2016 |
| WO | WO 2016/125164 | 8/2016 |
| WO | WO 2016/125165 | 8/2016 |
| WO | WO 2016/162865 | 10/2016 |
| WO | WO 2016/164452 | 10/2016 |
| WO | WO 2016/183244 | 11/2016 |
| WO | WO 2016/186949 | 11/2016 |
| WO | WO 2017/51424 | 3/2017 |
| WO | WO 2017/168422 | 10/2017 |
| WO | WO 2017/218018 | 12/2017 |
| WO | WO 2018/15951 | 1/2018 |
| WO | WO 2018/037306 | 3/2018 |
| WO | WO 2018/122845 | 7/2018 |
| WO | WO 2018/209341 | 11/2018 |
| WO | WO 2019/021005 | 1/2019 |
| WO | WO 2019/057133 | 3/2019 |
| WO | WO 2019/090421 | 5/2019 |
| WO | WO 2019/113493 | 6/2019 |
| WO | WO 2019/231993 | 12/2019 |
| WO | WO 2020/003105 | 1/2020 |
| WO | WO 2020/014302 | 1/2020 |
| WO | WO 2020/075036 | 4/2020 |
| WO | WO 2020/145331 | 7/2020 |
| WO | WO 2020/160677 | 8/2020 |
| WO | WO 2020/182189 | 9/2020 |
| WO | WO 2020/183457 | 9/2020 |
| WO | WO 2020/229388 | 11/2020 |
| WO | WO 2021/014370 | 1/2021 |
| WO | WO 2021/205449 | 10/2021 |
| WO | WO 2022/010089 | 1/2022 |
| WO | WO 2022/037524 | 2/2022 |
| WO | WO 2022/052996 | 3/2022 |
| WO | WO 2022/101227 | 5/2022 |
| WO | WO 2022/167822 | 8/2022 |
| WO | WO 2022/271841 | 12/2022 |

(56) References Cited

FOREIGN PATENT DOCUMENTS

| WO | WO 2023/046802 | 3/2023 |
|---|---|---|
| WO | WO 2023/056246 | 4/2023 |
| WO | WO 2023/152477 | 8/2023 |

OTHER PUBLICATIONS

Garcia-Gutierrez et al, "Electroanalytical Sensing of Flunitrazepam Based on Screen Printed Graphene Electrodes" Chemosensors 2013, 1, p. 68-77. (Year: 2013).*

Abe et al. "One-Chip Multichannel Quartz Crystal Microbalance (QCM) Fabricated by Deep RIE", Sensors and Actuators A: Physical, 82(1-3): 139-143, May 15, 2000.

Ai et al. "Recent Progress in Lab-on-A-Chip for Pharmaceutical Analysis and Pharmacological/Toxicological Test", TrAC Trends in Analytical Chemistry, 117: 215-230, Aug. 2019.

Akbar et al. "Chip-Scale Gas Chromatography: From Injection Through Detection", Microsystems & Nanoengineering, 1: 15039-1-15039-8, Published Online Dec. 21, 2015.

Ali et al. "The Detection of Flunitrazepam in Beverages Using Portable Raman Spectroscopy", Drug Testing and Analysis, 9(2): 256-259, Published Online Mar. 16, 2016.

Anders et al. "Progress in Miniaturization and Low-Field Nuclear Magnetic Resonance", Journal of Magnetic Resonance, 322: 106860-1-106860-6, Jan. 2021.

Argente-Garcia et al. "A Passive Solid Sensor for In-Situ Colorimetric Estimation of the Presence of Ketamine in Illicit Drug Samples", Sensors and Actuators B, 253: 1137-1144, Dec. 2017.

Bravo et al. "Reliable, Sensitive, Rapid and Quantitative Enzyme-Based Assay for Gamma-Hydroxybutyric Acid (GHB)", Journal of Forensic Sciences, 49(2): 379-387, Mar. 2004.

Chen et al. "A Dual-Angle Fiber Dynamic Light Scattering System Integrated With Microfluidic Chip for Particle Size Measurement", Optics & Laser Technology, 150: 107891-1-107891-8, Jun. 2022.

Cho et al. "Chemiluminometric Enzyme-Linked Immunosorbent Assays (ELISA)-On-A-Chip Biosensor Based on Cross-Flow Chromatography", Analytica Chimica Acta, 632(2): 247-255, Published Online Nov. 17, 2008.

Chung et al. "Microaffinity Purification of Proteins Based on Photolytic Elution: Toward An Efficient Microbead Affinity Chromatography on A Chip", Electrophoresis, 26(3): 694-702, Feb. 2005.

Coelho Rezende et al. "Micro Photoionization Detectors", Sensors and Actuators B: Chemical, 287: 86-94, May 15, 2019.

Cooman et al. "Implementing Machine Learning for the Identification and Classification of Compound and Mixtures in Portable Raman Instruments", Chemical Physics Letters, 787: 139283-1-139283-10, Jan. 2022.

Fratila et al. "Small-vol. Nuclear Magnetic Resonance Spectroscopy", Annual Review of Analytical Chemistry, 4: 227-249, Published Online Mar. 8, 2011.

Garcia-Gutierrez et al. "Electroanalytical Sensing of Flunitrazepam Based on Screen Printed Graphene Electrodes", Chemosensors, 1(3): 68-77, Dec. 6, 2013.

Greaves et al. "Toward On-Chip X-Ray Analysis", Lab on A Chip, 5(4): 382-391, Advance Access Publication Feb. 18, 2005.

Harper et al. "An Overview of Forensic Drug Testing Methods and Their Suitability for Harm Reduction Point-of-Care Services", Harm Reduction Journal, 14(1): 52-1-52-13, Jul. 31, 2017.

He et al. "Recent Advances in Microchip-Mass Spectrometry for Biological Analysis", TrAC Trends in Analytical Chemistry, 53: 84-97, Jan. 2014.

Ingels et al. "Screening and Confirmation Methods for GHB Determination in Biological Fluids", Analytical and Bioanalytical Chemistry, 406(15): 3553-3577, Published Online Feb. 6, 2014.

Jia et al. "Isothermal Titration Calorimetry in A 3D-Printed Microdevice", Biomedical Microdevices, 21(4): 96-1-96-8, Nov. 11, 2019.

Jiménez-Pérez et al. "Electrocatalytic Performance Enhanced of the Electrooxidation of Gamma-Hydroxybutyric Acid (GHB) and Ethanol on Platinum Nanoparticles Surface. A Contribution to the Analytical determination of GHB in the Presence of Ethanol", Sensors and Actuators B: Chemical, 256: 553-563, Mar. 2018.

Jiménez-Pérez et al. "Electrochemical Behaviour of Gamma Hydroxybutyric Acid at Aplatinum Electrode in Acidic Medium", Electrochimica Acta, 111: 601-607, Available Online Aug. 19, 2013.

Kong et al. "Microfluidic Diatomite Analytical Devices for Illicit Drug Sensing With PPB-Level Sensitivity", Sensors and Actuators B: Chemical, 259: 587-595, Available Online Dec. 16, 2017.

Li et al. "Chip-Based Ion Chromatography (Chip-IC) With A Sensitive Five-Electrode Conductivity Detector for the Simultaneous Detection of Multiple Ions in Drinking Water", Microsystems & Nanoengineering, 6(11): 66-1-66-8, Aug. 24, 2020.

Li et al. "On-Chip Spectrometers Using Stratified Waveguide Filters", Nature Communications, 12(1): 2704-1-2704-9, May 11, 2021.

Mao et al. "Cell Analysis on Chip-Mass Spectrometry", TrAC Trends in Analytical Chemistry, 107: 43-59, Oct. 2018.

Mielczarek et al. "Miniaturization in Mass Spectrometry", Mass Spectrometry Reviews, 39(5-6): 453-470, Sep. 2020.

Morang "A Sensor for A Date-Rape Drug, Incorporated Into A Beverage Container", A Major Qualifying Project Report Submitted to the Faculty of Worcester Polytechnic Institute, in Partial Fulfillment of the Requirements for the Degree of Bachelor of Science, p. 1-32, Apr. 16, 2012.

Muñoz-Martínez et al. "Electrochemical Instrumentation of An Embedded Potentiostat System (EPS) for A Programmable-System-On-A-Chip", Sensors, 18(12): 4490-1-4490-21, Dec. 18, 2018.

Murrihy et al. "Ion Chromatography On-Chip", Journal of Chromatography A, 924(1):233-238, Jul. 27, 2001.

Narang et al. "Naked-Eye Quantitative Assay on Paper Device for Date Rape Drug Sensing Via Smart Phone APP", Vacuum, 153: 300-305, Jul. 1, 2018.

Piendl et al. "2D in Seconds: Coupling of Chip-HPLC With Ion Mobility Spectrometry", Analytical Chemistry, 91(12): 7613-7620, Published Online May 24, 2019.

Piffoux et al. "Potential of On-Chip Analysis and Engineering Techniques for Extracellular Vesicle Bioproduction for Therapeutics", VIEW, 3(1): 20200175-1-20200175-15, Published Online Jan. 31, 2022.

Poulladofonou etl. "Wearable Electronic Finger for Date Rape Drugs Screening: From 'Do-It-Yourself' Fabrication to Self-Testing", Analytical Chemistry, 94(9): 4087-4094, Feb. 23, 2022 & Supporting Information.

Procida et al. "Smartphone-Based Colorimetric Determination of Gamma-Butyrolactone and Gamma-Hydroxybutyrate in Alcoholic Beverage Samples", Journal of Forensic Sciences, 67(4): 1697-1703, Published Online Apr. 3, 2022.

Razlansari et al. "Nanobiosensors for Detection of Opioids: A Review of Latest Advancements", European Journal of Pharmaceutics and Biopharmaceutics, 179: 79-94, Available Online Sep. 5, 2022.

Reichert Technologies "Explained: Sensor Chips for Surface Plasmon Resonance and Other Applications", Protein Expression and Analysis, 6 P., Posted May 19, 2017.

Ren et al. "A Review of the Development and Application of Space Miniature Mass Spectrometers", Vacuum, 155: 108-117, Sep. 2018.

Shaltout et al. "Photonic Spin Hall Effect in Gap-Plasmon Metasurfaces for On-Chip Chiroptical Spectroscopy", Optica, 2(10): 860-863, Published Online Sep. 28, 2015.

Smith et al. "Forensic Electrochemistry: The Electroanalytical Sensing of Rohypnol® (Flunitrazepam) Using Screen-Printed Graphite Electrodes Without Recourse for Electrode or Sample Pre-Treatment", The Analyst, 138(20): 6185-6191, Published Online Aug. 23, 2013.

Tsunoda "On-Chip Liquid Chromatography", Encyclopedia, 2(1): 617-624, Mar. 15, 2022.

Xu et al. "A Smartphone-Based Quantitative Point-of-Care Testing (POCT) System for Simultaneous Detection of Multiple Heavy Metal Ions", Chemical Engineering Journal, 394: 124966-1-124966-9, Available Online Apr. 8, 2020.

(56) References Cited

OTHER PUBLICATIONS

American Friends of Tel Aviv University "New Line of Defense Against Sexual Assault: Researchers Develop Pocket-Sized Sensor to Detect 'Date Rape' Drugs", Science Daily, 3 P., Aug. 9, 2011.
Metro Spy Supply "Is Your Drink Safe? Date Rape Drug Detection Sticker", Metro Spy Supply, The Wayback Machine, 8 P., 2022.

* cited by examiner

GAMMA-HYDROXYBUTYRATE

GC-MS spectrum of

GC-EI-TOF spectrum of
(Ionization Mode positive)

Most downfield peak of 13C Nuclear Magnetic Resonance (NMR) spectrum of GHB

© 2016-2021 W. Robien, Inst. of Org. Chem., Univ. of Vienna. All Rights Reserved.

Orbitrap-based MS spectrum of GHB

Triple quadrupole mass spectrometer (TQMS; QqQ) spectrum of GHB

LC-MS spectrum of
(Ionization Mode negative)

GAMMA-BUTYROLACTONE

FLUNITRAZEPAM

KETAMINE

MDMA (Ecstasy)

carisoprodol (Soma)

Diazepam

1H NMR Spectra

© 2009-2021 John Wiley & Sons, Inc.
All Rights Reserved.

13C NMR Spectra

© 1980, 1981-2021 John Wiley & Sons, Inc.
All Rights Reserved.

Mass Spectrometry
GC-MS
(Ionization mode Positive)

GC-MS
CI-B
(Ionization mode Positive)

MS-MS
(Ionization mode Positive)

LC-MS
LC-ESI-QTOF spectrum of
(Ionization type Positive)

DATE RAPE DRUG DETECTION DEVICE AND METHOD OF USING SAME

RELATED APPLICATION

This application claims the benefit of priority of U.S. Provisional Patent Application No. 63/536,524 filed on Sep. 5, 2023, the contents of which are incorporated herein by reference in their entirety.

FIELD AND BACKGROUND OF THE INVENTION

The present invention, in some embodiments thereof, relates to a portable drug-facilitated sexual assault (DFSA) drugs detection device, and more particularly, but not exclusively, to a date rape drug (DRD) detection device which comprises a cellphone and/or a cellphone protective cover and/or a cellphone screen, front or back protective cover and/or a cellphone stylus and/or other cellphone add-on and/or any combination thereof and a DRD detection system for detecting the DRD. The DRD detection system is physically associated with any one of or more of the cellphone and/or the cellphone protective cover and/or the cellphone screen, front or back protective cover and/or the cellphone stylus and/or other cellphone add-on and/or any combination thereof.

When a young person, such as the present inventor, heads to a bar, pub, party friends gathering or any other social event in which beverages are served, they're seeking a vibrant social atmosphere where they can relax, connect with friends and new people, enjoy a variety of drinks, explore different forms of entertainment like live music or games, and escape the routine in a lively and dynamic setting. However, it's crucial to remain cautious in these settings, given the concern of DFSA. Staying vigilant about their surroundings, watching their drinks, and prioritizing safety, whether they're with friends or meeting new people, takes away some of the fun in going out, but it is paramount. This balance between enjoyment and awareness ensures a memorable and secure night out.

The invention described herein was conceived by the inventor after attending a bar with a group of friends and one of the female friends in the group started to behave as being intoxicated, albeit she was consuming solely non-alcoholic beverages throughout the evening. In this case, the female friend was saved by her group of friends from likely being raped since they noticed and were alarmed by her mental and physical behavior. They drove her to a nearby hospital and she was tested positive to GHB, a common DRD which is frequently used in Israel for date raping. The inventor was aware of the fact that in recent years immense efforts are exercised by the governmental and private sectors to develop efficient methods to detect DRDs in drinks on site (e.g., venues or settings of social events). Many DRD detectors are available on the market, offered inter alia, on line, including, but not limited to, the following products provided by the following companies:

DrinkSafe Technologies: offering test kits like "Drink Safe Coasters" and "Drink Safe Cards" that can detect common colorless, odorless drugs when dipped into a drink.

Undercover Colors: offering a nail polish that changes color when it comes into contact with certain substances, including some commonly used rape drugs.

SipChip: providing a small test strip that can be dipped into a drink to detect the presence of specific drugs, including GHB and Ketamine.

DrinkGuard: offering test strips that change color when exposed to common drugs used in drink spiking.

Test Your Drink: They provide test cards that can detect the presence of common date rape drugs.

Smart Drink Stirrers: These drink stirrers contain test strips that change color when they come into contact with certain drugs.

Drink Safe Technologies: offering portable drink testing kits that can detect the presence of various drugs.

DrinkSavvy: offering cups, straws, and glassware that change color when they come into contact with substances commonly used in drink spiking.

GHB Test Strips: These test strips specifically detect the presence of GHB (Gamma-Hydroxybutyric acid) in liquids.

Safety Cups: These cups have built-in test strips that detect the presence of drugs and change color accordingly.

Drink Detective: offering test coasters that can detect the presence of certain substances in beverages.

Regretfully these products and many others are not used frequently when attending events, venues or settings in which unwilling exposure to a rape drug is possible.

Hence, drug-facilitated sexual assault (DFSA) is a present and ever-growing problem, which spreads in public bars and pubs and other social event venues around the world, whereas these drugs can be used in any context, not just in a dating setting. Rape-date drugs, or "date rape drugs," (DRDs) are drugs that are slipped into someone's drink without their knowledge or consent. These drugs can cause a variety of effects, including impaired judgment, anterograde amnesia (the inability to form new memories), and sedation, all of which make the victim more vulnerable to sexual assault. In a study by the National Institute on Drug Abuse, 1 in 5 women reported having been drugged without their knowledge at some point in their lives. According to the Rape, Abuse & Incest National Network (RAINN), 1 in 7 women will be sexually assaulted in their lifetime.

While there are a variety of communal and personal measures that can be taken to overcome DFSA, one of the explored and attempted measures is the provision of technological means for detection of a drug in a beverage by a layman which can be put to use at the location of beverage consumption (on-site), namely technological means that can be used at the social event by an ordinary person without a technological background, such as the customer or the barkeeper/mixologist. Many analytical methods for detecting DFSA including DRDs, although quite effective, are too elaborate to be used on-site, however, some methods further described below and products listed above, have been employed in several devices which are particularly suitable for on-site detection of DFSA drugs.

US20040146429A1 (2001) provides an apparatus and method for detecting the clandestine placement of an illicit chemical present in a beverage, comprising a manufactured porous substrate, one or more calorimetric indicators embedded in or upon the substrate, and optionally, indication of the placement of the colorimetric indicators, wherein the manufactured porous substrate is a napkin, the paper lining of a beverage coaster, placemat, menu, match book, drink carrier, flyer, coupon, personal test kit or a business card.

US20030026731A1 (2001) provides a package for holding and disguising a chromatographic test of food and drink is formed in the shape of a drinking straw or stirrer. The package encloses test strips which are sensitive to particular drugs and produce a color change upon contact with the drug. The package has a view port or slit to observe the condition of the test strip upon contact with food and drink.

WO2006018619A1 (2004) provides a diagnostic device for potable liquids comprising a housing in the form of a waterproof tube having an inlet at one end for the reception of liquid and an outlet near its other end, and wicking material is arranged in the tube. If the device is dipped into a potable liquid, a sample will enter the reservoir in the tube from the inlet and will be drawn up by the wicking material to the reagent pads which will then indicate if drugs or other illicit obnoxious substances have been added to the liquid.

GB2418248A (2004) provides a testing device for detecting the presence of one or more substances in a fluid. The substances include, for example, covertly administered chemicals, such as date rape drugs. The device comprises a fully functional drinking straw having test means for detecting the presence of each substance in a fluid and indicating a positive test result. A user can thereby be alerted to the presence of the substance in the fluid prior to ingestion using an inconspicuous testing method. The testing device may be integrally formed with the straw or comprise a testing strip applied thereto. The testing device may be sensitive to the presence of benzodiazepines, Rohypnol, gamma hydroxy butyrate, amphetamine, or an allergen such as nuts.

GB2430488A (2005) provides a method of use, and a drinks accessory for insertion into a drink, comprising one or more assay areas disposed thereon which are capable of testing a drink for the presence of a contaminant and conveying results to the user. The device may be a stirrer or straw and may indicate the presence of a contaminant by means of a color change.

GB2438675A (2006) provides an integrated liquid sampling and testing device for potable liquids comprising a housing in the form of a waterproof tube, with the distil end of the device sealed such that it is air and liquid tight. The near end of the tube has an insert which acts as an internal pipette when the device is operated and liquid is sampled into the device. The result of the analysis can be seen as a color change in the diagnostic chemicals through the transparent or translucent tube.

GB2447899A (2007) provides a device and method of automatically testing whether a drink has been spiked, comprising a glass receptacle having integrally incorporated therein means to detect the presence of unwanted substances e.g., Rohypnol (flunitrazepam), GHB (sodium gamma hydroxybutyric acid) etc. The receptacle comprises a testing strip incorporated within the base with valves in the bottom rim through which small amounts of liquid in the glass travel to the testing bay for analysis. The liquid may be released intermittently into the testing bay every time the glass is moved, whereas the testing strip may also be removeable and replaceable.

GB2486472A (2010) provides an apparatus and a method for testing for the presence of at least one date rape drug or prodrug thereof has at least one portion which changes color in the presence of the drug(s) to be tested. The apparatus is in the form of a drinking vessel or comprises a drinking paraphernalia for immersion in a drinking vessel, preferably a drinking straw, a stirring stick or a decorative umbrella. The apparatus may comprise a chamber having a transparent or translucent portion, a port allowing fluid communication with the chamber and a portion changing color in the presence of date rape drug(s) such as 4-hydroxybutanoic acid, 4-hydroxypentanoic acid, ketamine, flunitrazepam or diazepam.

U.S. Pat. No. 9,029,098B1 (2014) provides a date rape drug detector that includes an elongated shaft having a testing strip therein that is deployable and exhibiting a plurality of reactive spots that change color in the presence of a date rape drug that allows a user can test a beverage for the presence of a date rape drug at progressive intervals.

U.S. Ser. No. 10/274,475B2 (2014) provides an apparatus configured to detect a beverage that is contaminated with a substance, which includes a testing material comprising a cavity having a complementary shape to a molecule associated with the testing substance, wherein the taste substance filling the cavity bleeds out into the beverage when the molecule associated with the substance in the beverage replaces the taste substance filling the cavity as an indicator that the substance is present in the beverage.

US20180318145A1 (2018) provides a wearable apparatus and methods for detecting the presence of a targeted substance in a liquid, which can be implemented as a fingernail that detects illicit drugs in a beverage. The wearable apparatus comprises a detection layer comprising an indicator that is configured to display a signal upon the detection of an interaction with the targeted substance. In some examples, the wearable apparatus can include a lateral flow assay.

WO2022248741A1 (2021) discloses a straw or stirrer with a drug detection test, which comprises a test strip containing a chemical reagent that detects the presence of drugs dissolved in beverages, changing color depending on whether the drink contains a dissolved drug.

U.S. Ser. No. 11/448,587B1 (2021) discloses coaster-shaped devices and methods for detecting drugs and alerting the user to the presence of the drug, such as γ-hydroxybutyrate and γ-butyrolactone, using infrared spectrometry.

MYBOUNCER LTD reported filing a patent application titled "Apparatus for Identifying Presence of a Substance of Interest, and Method of Using Thereof", which discloses an electro-optical device that connects to a phone and uses laser-based spectroscopy to detect drink-spiking substances in a beverage.

Additional prior art documents include U.S. Ser. No. 10/894,643B2, U.S. Pat. No. 8,920,857B2, U.S. Ser. No. 11/311,124B2, U.S. Pat. No. 9,285,352B2, US20160209381A1 and US20170086610A1.

The main problems associated with the abovementioned solutions revolve around accessibility, availability, responsibility, liability, willingness and chance. The presently available solutions rely of the provision of a specialized and dedicated device for detecting DRDs, which the users must remember ( . . . or not forget) to bring with them when going to a public establishment for a drink, or rely on the establishment to provide such specialized dedicated device. However, this creates potential challenges since people may forget to bring the specialized device, which is not necessarily with them on regular daily basis, and the establishments are reluctant from providing such specialized devices as they may risk their reputation (if DRD detected in their venue) and face legal consequences if a device provided by the establishment is misused or found to be defective.

While some known DRD detection devices may use cellphone functions such as power, computing, communication and display means, these devices are either NOT operable by a laymen to identify a DRD in a social setting and/or are NOT physically associated (as this phrase is further defined below) with the cellphone and/or its protective cover and/or its screen, front or back covers and/or the cellphone stylus and/or the cellphone add-on or any combination thereof, in a way that allows day-to-day (i.e., daily) use and/or operation of any function of the cellphone and/or the cellphone protective cover and/or the cellphone screen, front or back protective cover and/or the stylus and/or the other cellphone add-on and/or any combination thereof, thereby diminishing the ability, need and/or reducing a chance of removing the DRD detection system from the cellphone and/or the cellphone protective cover and/or the cellphone screen, front or back protective cover and/or the stylus and/or other cellphone add-on and/or any combination thereof, so as to allow instant use of the DRD detection system whenever required Hence, there is a strong felt need for a device for detecting date rape drugs in a beverage that is owned and operated by a laymen seeking to avoid DFSA, and implemented a detection system that is physically associated (as this phrase is further defined below) with a cellphone and/or any cellphone protective cover and/or cellphone screen, front or back protective cover and/or cellphone stylus and/or other cellphone add-on and/or any combination thereof, making it unlikely to be forgotten, misplaced or otherwise missing when and where it is needed.

SUMMARY OF THE INVENTION

One of the objectives of the present invention is to provide ordinary people, users of cellphone, who may not have experience with DRD detection technology, the ability to protect themselves from DFSA. To make this easier and effective, a DRD detection device is physically tethered to, i.e., physically associated with (as this phrase is further defined herein below) an object that people are likely to have with them at all times, a cellphone, its protective cover and/or its screen protective cover. This "cellphone-bound" device solves several problems associated with DRD detection, including:
  a. Accessibility: the ability to detect DRD simply and rapidly in a non-laboratory setting and without academic training, using a personally portable device which is the device carried by all at all times, namely a cellphone, its protective cover and/or its screen protective cover;
  b. Liability: putting the responsibility to provide the device (and carry out a DRD detection assay) on the device owner rather than on a host or a third party; and
  c. Availability: making sure that the device will be with the user when needed, without having to change habits or reeducate the user.

Following is a non-exclusive list including some examples of embodiments of the invention. The invention also includes embodiments which include fewer than all the features in an example and embodiments using features from multiple examples, also if not expressly listed below.

Thus, according to an aspect of some embodiments of the present invention, there is provided a device for detecting at least one date rape drug (DRD) in at least one beverage in a social event, the device that includes a cellphone and/or a cellphone protective cover and/or a cellphone screen, front or back protective cover and/or a cellphone stylus and/or other cellphone add-on and/or any combination thereof and a DRD detection system for detecting the at least one DRD, the DRD detection system being operable by a laymen for DRD detection and being physically associated with the cellphone and/or the cellphone protective cover and/or the cellphone screen, front or back protective cover and/or the stylus and/or the other cellphone add-on and/or any combination thereof, such that day-to-day use and/or operation of any function of the cellphone and/or the cellphone protective cover and/or the cellphone screen, front or back protective cover and/or the stylus and/or the other cellphone add-on and/or any combination thereof is substantially not affected by the DRD detection system, thereby diminishing the ability, need and/or reducing a chance of removing the DRD detection system from the cellphone and/or the cellphone protective cover and/or the cellphone screen, front or back protective cover and/or the stylus and/or other cellphone add-on and/or any combination thereof, so as to allow instant use of the DRD detection system whenever required.

In some embodiments, the DRD detection system is physically associated with the cellphone.

In some embodiments, the DRD detection system is physically associated with the cellphone protective cover.

In some embodiments, the DRD detection system is physically associated with the cellphone screen, front or back protective cover or cellphone stylus or other cellphone add-on.

In some embodiments, the DRD detection system is physically associated:
  (a) in part with the cellphone and in part with the cellphone protective cover;
  (b) in part with the cellphone and in part the cellphone screen, front or back protective cover;
  (c) in part with the cellphone protective cover and in part the cellphone screen, front or back protective cover;
  (d) in part with the cellphone and in part the cellphone protective cover and in part the cellphone screen, front or back protective cover;
  (e) in part with the cellphone and in part the cellphone stylus; and/or
  (f) in part with the cellphone and in part with the other cellphone add-on.

In some embodiments, the DRD detection system is designed to detect a chemical property of the at least one DRD.

In some embodiments, DRD detection system is designed to detect a physical property of the at least one DRD.

In some embodiments, DRD detection system is designed to detect an electrochemical property of the at least one DRD.

In some embodiments, DRD detection system includes a spectra meter.

In some embodiments, the spectra meter is designed to identify spectra characterizing the at least one DRD.

In some embodiments, the DRD detection system includes an electrochemical sensor for detecting the at least one DRD.

In some embodiments, the DRD detection system includes at least one chemical reagent designed for generating a colorimetric effect and/or an electrochemical effect upon contacting with the at least one DRD, at least one chemical of the at least one chemicals is attached to and/or embedded within a solid support.

In some embodiments, the solid support is selected from the group consisting of the cellphone, the cellphone protective cover, the cellphone screen, front or back protective cover, the cellphone stylus, the other cellphone add-on and any combination thereof, a sticker adhered to any of the cellphone, the cellphone protective cover, the cellphone screen, front or back protective cover, the cellphone stylus, the other cellphone add-on and the any combination thereof, and a layer applied any of the cellphone, the cellphone protective cover, the cellphone screen, front or back protective cover, the cellphone stylus, the other cellphone add-on and the any combination thereof.

In some embodiments, the DRD detection system requires a source of energy to operate.

In some embodiments, the source of energy is a battery.

In some embodiments, the battery is inherent to the cellphone.

In some embodiments, the DRD detection system does not require a source of energy to operate.

In some embodiments, the DRD detection system is designed for repeated uses at least for negative results.

In some embodiments, the DRD detection system is designed for repeated uses for negative results.

In some embodiments, the DRD detection system is washable after use.

In some embodiments, the DRD is selected from the group consisting of gamma-hydroxybutyrate (γ-hydroxybutyrate; GHB), gamma-butyrolactone (γ-butyrolactone; GBL), flunitrazepam (Rohypnol), ketamine (Ketalar), methoxetamine (MXE), MDMA (Ecstasy), carisoprodol (Soma), a benzodiazepine, Diazepam, Alprazolam, Clonazepam, Lorazepam, Temazepam, Valium, Xanax, Klonopin, Ativan, Restoril, Normison, Temaze, Zolpidem, Zopiclone, a barbiturate, Phenobarbital, Secobarbital, Pentobarbital, Luminal, Seconal, Nembutal, phenobarbital, scopolamine, Hyoscine, morphine, heroin, fentanyl chloral hydrate, Aquachloral, Noctec, clonidine, Catapres, Kapvay, diphenhydramine, Benadryl, Nytol, and methamphetamine.

In some embodiments, the DRD detection system is capable of communicating with the cellphone.

In some embodiments, the cellphone has an integral sensor and a dedicated software communicating with the sensor for detecting the at least one DRD.

In some embodiments, the cellphone protective cover has an integral sensor and the cellphone has a dedicated software communicating with the sensor for detecting the at least one DRD.

In some embodiments, the cellphone stylus has an integral sensor and the cellphone has a dedicated software communicating with the sensor for detecting the at least one DRD.

In some embodiments, the cellphone other add-on has an integral sensor and the cellphone has a dedicated software communicating with the sensor for detecting the at least one DRD.

In some embodiments, the sensor and the software are designed to detect more than a single at least one DRD, to alert a user of the cellphone of a presence or absence of the at least one DRD and its chemical, common and/or street name or abbreviation.

In some embodiments, the dedicated software is housed in part in the cellphone and in part in a remote location.

In some embodiments, the software includes an AI software pre-trained to identify a spectra of the at least one DRD in the beverage.

In some embodiments, the software includes a data library of physical and/or electrochemical properties of the at least one DRD.

According to another aspect of some embodiments of the present invention, there is provided a method for detecting the presence or the absence of at least one DRD in a beverage, which is effected by contacting the DRD detection system for detecting the at least one DRD, which forms a part of the device as provided herein, with the beverage or a sample thereof, and based on the performance of the DRD detection system detecting and determining the presence or the absence of at least one DRD is the beverage.

According to yet another aspect of some embodiments of the present invention, there is provided a sticker for detecting at least one DRD, the sticker includes:
 (a) a solid matrix having a front side and a back side;
 (b) a chemically active component which includes at least one chemical reagent designed for generating a detectable effect when contacting the at least one DRD applied on or in the matrix, the chemically active component being accessible for at least one DRD detection from the front side; and
 (c) an adhesive layer on the back side, the adhesive layer being adherable to a cellphone and/or a cellphone protective cover and/or a cellphone screen, front or back protective cover and/or a cellphone stylus and/or other cellphone add-on and/or any combination thereof.

In some embodiments, the sticker further includes at least one of:
 (d) a front single use or reusable liner applied onto the front side to protect the at least one chemical when the sticker is stored and/or not in use; and
 (e) a back protective liner applied onto the adhesive layer to protect the adhesive layer when the sticker is stored before use.

In some embodiments, the sticker provided herein is adhered to the cellphone and/or the cellphone protective cover and/or the cellphone screen, front or back protective cover and/or cellphone stylus and/or other cellphone add-on and/or any combination thereof.

According to yet another aspect of some embodiments of the present invention, there is provided a device that includes a cellphone or cellphone protective cover having a stylus acceptor and a cellphone stylus acceptable is the stylus acceptor, wherein the cellphone stylus includes chemical reagents capable of a detecting at least one DRD.

According to yet another aspect of some embodiments of the present invention, there is provided a DRD detection system that includes a cellphone stylus and at least one chemical reagent physically associated therewith capable of detecting at least one DRD.

According to yet another aspect of some embodiments of the present invention, there is provided a DRD detection device that includes a cellphone and/or cellphone protective cover having a dedicated acceptor for accepting and physically securing therein a dedicated DRD detection system and a dedicated DRD detection system physically acceptable by and securable to the acceptor.

According to yet another aspect of some embodiments of the present invention, there is provided a DRD detection device that includes:
 (a) a cellphone;
 (b) a beverage sampler, having a sampling cavity for collecting a beverage sample at its distal end;
 (c) a DRD detection system which includes a spectra meter connected to and functionally communicating with the cellphone; and
 (d) a first sampler acceptor in the DRD detection system for positioning the sample inside the DRD detection system for allowing sample readout by the spectra meter.

In some embodiments, the DRD detection device further includes:
 (e) a cellphone and DRD detection system in a communal protective cover designed for protecting, securing and holding together the cellphone and the DRD detection system and for maintaining a form-factor of the cellphone.

In some embodiments, the DRD detection system is physically and functionally connected to the cellphone via a port of the cellphone.

In some embodiments, the communal protective cover is formed with a replacement port for replacing the port of the cellphone.

In some embodiments, the communal protective cover includes a second sampler acceptor for holding the sampler when not in use.

In some embodiments, the first sampler acceptor serves also for holding the sampler when not in use.

In some embodiments, the sampler also serves as a cellphone stylus.

According to yet another aspect of some embodiments of the present invention, there is provided a DRD detection device that includes a cellphone and/or a cellphone protective cover, the cellphone and/or the cellphone protective cover includes a dedicated cartridge for housing a plurality of releasable DRD detection systems.

According to yet another aspect of some embodiments of the present invention, there is provided a DRD detection device that includes a cellphone and/or a cellphone protective cover, the cellphone and/or the cellphone protective cover includes a dedicated holder for holding a dedicated releasable cartridge, the dedicated releasable cartridge for housing a plurality of releasable DRD detection systems.

In some embodiments, the dedicated releasable cartridge is an elongated member.

In some embodiments, the elongated member also serves as a cellphone stylus.

In some embodiments, each of the plurality of releasable DRD detection systems is shaped as a spheroid, a polyhedron, a toroid, a cylinder, a cone or a disk.

In some embodiments, each of the plurality of releasable DRD detection systems includes a chemistry suitable for detecting the presence of at least one DRD in a beverage.

In some embodiments, each of the plurality of releasable DRD detection systems has a specific weight allowing floating on a surface of a beverage or sinking to a bottom of a container containing the beverage.

BRIEF DESCRIPTION OF THE FIGURES

Some embodiments of the invention are herein described, by way of example only, with reference to the accompanying figures. With specific reference now to the figures in detail, it is stressed that the particulars shown are by way of example and for purposes of illustrative discussion of embodiments of the invention. In this regard, the description taken with the figures makes apparent to those skilled in the art how embodiments of the invention may be practiced.

In the figures:

FIG. 2 presents a non-limiting example of a DRD detection device 20, that includes cellphone 11 having various ports 11a, and unified DRD detection system 21, implemented as add-on 22 that physically connects to cellphone 11 and having various replacement ports 22a, or implemented in cellphone protective cover 23 in the form of case 24 having various replacement ports 22a;

DESCRIPTION OF EMBODIMENTS OF THE INVENTION

Figure 1:
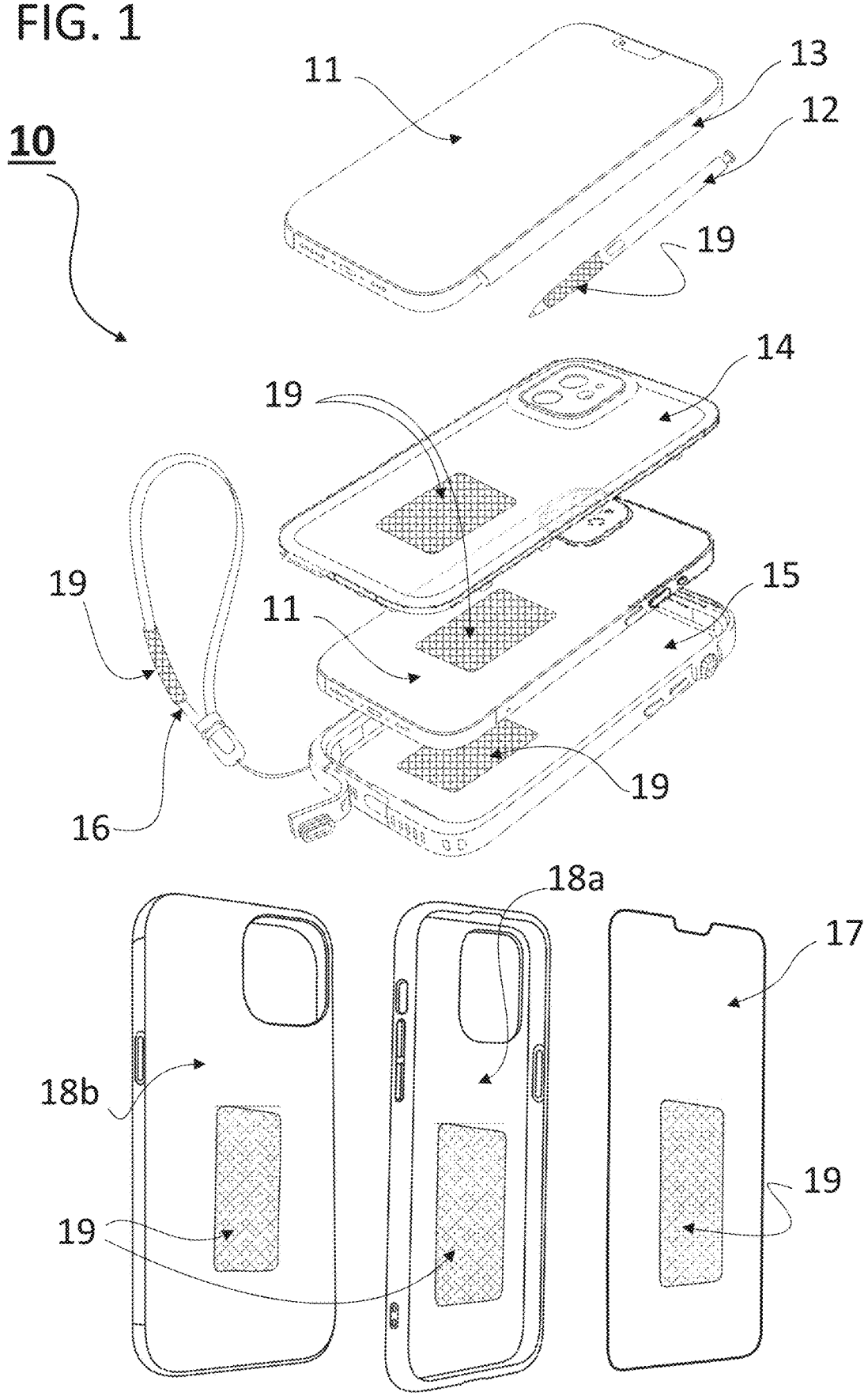
FIG. 1 presents various embodiments of DRD detection device 10, according to the present invention, showing non-limiting examples of cellphone 11, stylus 12, stylus acceptor 13, cellphone back protective cover 14, cellphone front protective cover 15, cellphone string add-on 16, cellphone screen protective cover 17, cellphone protective cover (inside view of the case) 18a, cellphone protective cover (outside view of the case) 18b, and DRD detection system 19, represented by a "Criss Cross" patterned area, physically associated with each.

The present invention, in some embodiments thereof, relates to a portable drug-facilitated sexual assault (DFSA) drugs detection device, and more particularly, but not exclusively, to a date rape drug (DRD) detection device comprising a cellphone and/or a cellphone protective cover and/or a cellphone screen, front or back protective cover and/or a cellphone stylus and/or other cellphone add-on and/or any combination thereof and a DRD detection system associate therewith for detecting at least one or more DRD(s).

Before explaining at least one embodiment of the invention in detail, it is to be understood that the invention is not necessarily limited in its application to the details of construction and the arrangement of the components and/or methods set forth in the following description and/or illustrated in the drawings and/or the examples or otherwise exemplified herein. The disclosure is meant to encompass other embodiments or of being practiced or carried out in various ways.

While conceiving the present invention, the present inventor realized that the state-of-the-art solutions provided so far for on site, self-detection of DRD by a layman, fail to overcome some practical, commercial and/or legal obstacles en route to a truly useful and dependable device that can be used by a layman while consuming a beverage at a public establishment. The most common problems include availability and responsibility, namely the user has to remember to carry a specialized device when planning to go out to a public establishment for a drink, or rely on the establishment to provide the device, while the establishment may be in a position that puts its reputation and liability at risk and expose it to lawsuits if/when a device that was provided by the establishment was misused or found faulty. Both limitations render all the state-of-the-art solutions impractical. Indeed, in the past ten years the number of technologies and product for detection of DRD increased exponentially, surprisingly, the use of DRD for date raping also substantially increased, showcasing that all the currently developed DRD detectors are not sufficiently practical to reduce DRD associated date rapes.

While further conceiving the present invention, the present inventor contemplated a detection system that can form a part of an object that a person is unlikely to forget to bring with, an object that is most likely to be with the person at all times, at least when going out, regardless of a prior location (home, work, friends, park, etc.) or a particular prior plan, such as a cellphone, and objects that come with the cellphone, such as the cellphone cover or the cellphone screen, front or back protective cover the cellphone stylus and/or a combination thereof. Accordingly, the detection device will most likely be with the user at all times including in places where the user spends time in a date rape susceptible locations such as a bar or pub or any other social event venue, and be owned by the user, thereby relieving the establishment from the burden of providing the device to the user, which may be associated with problematic public relations and/or legal consequences.

While reducing the present invention to practice, the present inventor has contemplated a device capable of detecting the presence of at least one DRD. The device for detecting the at least one DRD according to some embodiments of the invention comprises a cellphone and/or a cellphone protective cover and/or a cellphone screen, front or back protective cover and/or a cellphone stylus and/or other cellphone add-on and/or any combination thereof. The device for detecting the at least one DRD further comprises a detection system for detecting the at least one DRD. The DRD detection system is operable by a laymen for DRD detection. The DRD detection system is physically associated (as this term is further defined below) with the cellphone and/or the cellphone protective cover and/or the cellphone screen, front or back protective cover and/or cellphone stylus and/or other cellphone add-on and/or any combination thereof, such that the day-to-day use and/or operation of any function of the cellphone and/or cellphone protective cover and/or cellphone screen, front or back protective cover and/or cellphone stylus and/or other cellphone add-on and/or any combination thereof is substantially not affected by the DRD detection system, thereby diminishing the ability, need and/or reducing the chance of removing the DRD detection system from the cellphone and/or the cellphone protective cover and/or the cellphone screen, front or back protective cover and/or the cellphone stylus and/or other cellphone add-on and/or any combination thereof, so as to allow instant use of the DRD detection system whenever required.

As used herein the phrase "DRD detection device (is, being) operable by a laymen" refers to a device that can be easily operated to detect DRD by an ordinary person (laymen) without specialized knowledge, expertise skills or training in the field of DRD detection. It implies that the invention is user-friendly, intuitive, and does not require extensive expertise or skill to operate. In context of the present invention, as will be understood from the below, the "laymen" user of the invention needs no special knowledge or skills in chemistry, physics, electrochemistry, data analysis and/or artificial intelligence, etc. The laymen according to the invention will know how to operate the DRD detection device by reading simple instructions and/or operating a simple to operate application installed on the user's cellphone.

As used herein the phrase "physically associated" may two have alternative or cumulative meanings, as will be briefly described and exemplified hereinbelow:

1. "Integrally formed with." When the DRD detection system is integrally formed with the cellphone and/or cellphone protective cover and/or the cellphone screen, front or back protective cover and/or cellphone stylus and/or other cellphone add-on and/or any combination thereof, the ability of removing the DRD detection system from the cellphone and/or the cellphone protective cover and/or the cellphone screen, front or back protective cover and/or cellphone stylus and/or other cellphone add-on and/or any combination thereof by a layman or even a professional is totally or substantially diminished. However, the integrally formed DRD detection system is so designed such that day-to-day use and/or operation of any function of the cellphone by its user/owner is not affected by the integral formation of the DRD detection system within the DRD detection device. For example, a spectra meter or an electrochemical detector (numerous additional electronic detectors suitable for implementation with the DRD detection device of the present invention are described in detail herein below) integrally formed within a cellphone body or integrally formed within a cellphone protective cover body, whereby, (a) the spectra meter or electrochemical detector is energized by the cellphone power source or its own power source which is charged concomitantly with the charging of the cellphone; (b) the spectra meter or electrochemical detector are designed such that day-to-day use and/or operation of any function of the cellphone and/or cellphone protective cover is not affected by the integral formation of the of the spectra meter or electrochemical detector; and (c) the spectra meter or electrochemical detector, the cellphone or both have software suitable for detecting and of reporting of the presence or absence of at least one DRD in a tested beverage. In another not limiting example, a combination of chemical reagents capable of detecting the presence or absence of at least one DRD which are permanently applied directly onto a surface of the cellphone and/or the cellphone protective cover and/or the cellphone screen, front or back protective cover and/or cellphone stylus and/or other cellphone add-on and/or any combination thereof are inherently so designed such that day-to-day use and/or operation of any function of the cellphone is not affected by the integral formation of the DRD detection system. The functions of the cellphone which are not affected by the integral formation of the cellphone and/or the cellphone protective cover and/or the cellphone screen, front or back protective cover and/or cellphone stylus and/or other cellphone add-on and/or any combination thereof with the DRD detection system may include, inter alia, charging, camera operation, sound display, recording, communication and visual display operations. The functions of the additional add-ons listed herein and which are maintained albeit the association with the DRD detection system are further elaborated hereinbelow.

2. "Connected to" or "connectable to." When the DRD detection system is connected to or connectable to the cellphone and/or the cellphone protective cover and/or the cellphone screen, front or back protective cover and/or cellphone stylus and/or other cellphone add-on and/or any combination thereof, while the ability of removing the DRD detection system from the cellphone and/or the cellphone protective cover and/or the cellphone screen, front or back protective cover and/or cellphone stylus and/or other cellphone add-on and/or any combination thereof by a layman is not totally diminished but is obviated because the DRD detection system is so designed such that day-to-day use and/or operation of any function of the cellphone is not affected by the connection between the cellphone and/or the cellphone protective cover and/or the cellphone screen, front or back protective cover and/or cellphone stylus and/or other cellphone add-on and/or any combination thereof to the DRD detection system, and in the case any of the functions is disabled by the connection, a substantially identical replacement function is provided with the DRD detection system. For example, a spectra meter or an electrochemical detector (as mentioned above, numerous additional electronic detectors suitable for implementation with the DRD detection device of the present invention are described in detail herein below) are connected to or connectable to a cellphone or a cellphone protective cover, whereby, (a) the spectra meter or electrochemical detector is energized by the cellphone battery or its own battery which is charged concomitantly with the changing of the cellphone; and (b) the spectra meter or electrochemical detector are designed such that day-to-day use and/or operation of any function of the cellphone or cellphone cover is not affected by the physical connection of the of the spectra meter or electrochemical detector; and (c) the spectra meter or electrochemical detector, the cellphone or both have software suitable for detecting and reporting of the presence or absence of at least one DRD in a tested beverage. In another not limiting example, a combination of chemical reagents capable of detecting the presence or absence of at least one DRD which are applied directly onto a surface of sticker which is adhered or adherable (i.e., connected or connectable) to a surface of the cellphone and/or the cellphone protective cover and/or the cellphone screen, front or back protective cover and/or cellphone stylus and/or other cellphone add-on and/or any combination thereof are inherently so designed such that day-to-day use and/or operation of any function of the cellphone and/or any of its additional add-ons described herein, is not affected by the connection therewith of the DRD detection system. Similarly, the functions of the cellphone which are not affected by the integral formation of the cellphone and/or the cellphone protective cover and/or the cellphone screen, front or back protective cover and/or cellphone stylus and/or other cellphone add-on and/or any combination thereof with the DRD detection system may include, inter alia, charging, camera operation, sound display, recording, communication and visual display operations. The functions of the additional add-ons listed herein and which are maintained albeit the association with the DRD detection system are further elaborated hereinbelow.

Is it to be understood that according to some embodiments of the present invention certain components of the DRD detection device may be integral (e.g., spectra meter which is integral to the cellphone or cellphone protective cover) and other components such as a combination of chemical reagents capable of colorimetrically reacting in the presence of at least one DRD which reagents are applied via a sticker onto a surface of the cellphone and/or the cellphone protective cover and/or the cellphone screen, front or back protective cover and/or cellphone stylus and/or other cellphone add-on and/or any combination thereof and the reaction analyzed with the spectra meter do determine the presence or absence of the at least one DRD in a tested beverage.

A DRD Detection Device:

Thus, according to an aspect of some embodiments of the present invention, there is provided a device for detecting at least one date rape drug (DRD), the device comprises a cellphone and/or a cellphone protective cover and/or a cellphone screen, front or back protective cover and/or a cellphone stylus and/or other cellphone add-on and/or any combination thereof and a DRD detection system for detecting the at least one DRD, the DRD detection system being physically associated with the cellphone and/or the cellphone protective cover and/or the cellphone screen, front or back protective cover and/or cellphone stylus and/or other cellphone add-on and/or any combination thereof, such that day-to-day use and/or operation of any function of the cellphone and/or the cellphone protective cover and/or the cellphone screen, front or back protective cover and/or the cellphone stylus, and or any other cellphone add-on and/or a combination thereof is substantially not affected by the DRD detection system, thereby diminishing the ability, need and/or reducing a chance of removing the DRD detection system from the cellphone and/or the cellphone protective cover and/or the cellphone screen, front or back protective cover and/or the cellphone stylus, and or any other cellphone add-on and/or a combination thereof, so as to allow instant use of the detection device whenever required.

FIG. 1 presents various embodiments of device 10, according to the present invention, showing non-limiting examples of cellphone 11, stylus 12, stylus acceptor 13, cellphone back protective cover 14, cellphone front protective cover 15, cellphone string add-on 16, cellphone screen protective cover 17, cellphone protective cover (inside view of the case) 18a, cellphone protective cover (outside view of the case) 18b, and DRD detection system 19, represented by a "Criss Cross" patterned area, physically associated with each.

In context of the drawings, features that are inherent to a cellphone, a cellphone protective cover, a cellphone screen, front or back protective cover, a cellphone stylus, and any other cellphone add-on, which are not specifically addressed, are shown partially or not shown.

As one of the objectives of the present invention is to provide an ordinary person, a laymen, namely a person having no particular experience in chemistry or other technological aspect of DRD detection, a self-served capability to protect oneself from DFSA, and further to facilitate this provision by association of the necessary detection system to an object that would most likely be with the person or less likely to be forgotten or misplaced, namely a cellphone and to the extent used, its associated covers and other add-ons, the DRD detection system provided herein is both physically associated and to the extent needed, functionally associated, as defined and exemplified herein, with the cellphone and/or the cellphone protective cover and/or the cellphone screen, front or back protective cover and/or cellphone stylus and/or other cellphone add-on and/or any combination thereof.

As used herein the term "cellphone" is used to refer to any communication device that is carried by a person, such as a smartphone, a mobile phone, a cellular cellphone and a satellite phone. A cellphone in the context of a smartphone, is a mobile electronic device that combines the functionalities of a mobile phone with those of a handheld computer. It typically features a touchscreen display interface, for visual display and for allowing users to interact with the device through taps and swipes, with their finger(s) and/or a dedicated cellphone stylus and/or a camera interface allowing uses to interact therewith with facial recognition or body or hand gestures and/or audio interface allowing uses to interact therewith with voice commands. Smartphones are equipped with various communication features, including voice calls, text messaging, internet connectivity through Wi-Fi or cellular data networks and Bluetooth connectivity to nearby devices. Additionally, they offer a wide range of applications and services, such as web browsing, email, social media, navigation, multimedia playback, and access to app stores for downloading and installing additional software and content, including, inter alia, games, guides, etc. Smartphones have become an essential part of modern life, providing users with the ability to stay connected, access information, enjoy content and perform numerous tasks on the go.

As used herein the term "cellphone protective cover" refers to a flexible case and/or a hard case dedicated for harboring the cellphone and for protecting the cellphone e.g., in case it is dropped, from physical damage. The cellphone protective cover typically allows the use of the cellphone functions once covered, including, inter alia, charging, use of audio, use of cameras, display/screen view and input, and the various communications afforded by a cellphone, including, inter alia, cellular communication, satellite communication (GPS), Wi-Fi communication and Bluetooth communication. Some cellphone protective covers comprise additional features, such as, for example, extra power source for powering the cellphone with additional power, also known as "battery case" (see, for example U.S. Pat. No. 10,170,738), mechanism for allowing wireless charging of the cellphone while being protected by its cover, credit card or identification card or business card or money internal or external pocket, money clip, belt clip, embedded pepper spray container and discharge mechanism, shocker electrodes, their associated power supply or connecting mechanism to the integral power supply of the cellphone, and/or epinephrine container and its discharge mechanism to list a few.

A cellphone screen protective cover is typically a cellphone dedicated transparent film adherable to the screen of the cellphone for protection the screen from physical damage, such as scratching or breaking, while allowing the use of the screen for viewing and inputting touch commands by a user.

A cellphone back or front protective cover is typically a cellphone dedicated transparent or none transparent film adherable to the back face of a cellphone for protecting the back face of the cellphone from physical damage such as scratching. In most cases a cellphone back protective cover is used to protect the back of the cellphone to some extent, while avoiding the use of a cellphone protective cover which is visually pronounced and therefore dislikable by some cellphone users.

A cellphone stylus is a dedicated elongated member having a distal and proximal end. The proximal end is designed to be held by a user operating the stylus. The distal end is typically pointed and/or rounded and is used as an input device for inputting user commands via the telephone screen. A cellphone or cellphone protective cover equipped with a cellphone stylus has a cellphone stylus acceptor for accepting and securely holding the cellphone stylus when not in use.

Other "cellphone add-on" refers to any device and accessory designed dedicatedly to be used with a cellphone in context of the day-to-day use of the cellphone, such as, but not limited to, a dedicated cellphone carry bag, a dedicated cellphone carry strap, a dedicated cellphone grip, a dedicated cellphone stylus pen, a dedicated cellphone belt-clip, a dedicated cellphone pocket, a dedicated cellphone holster, etc., which, if owned by a cellphone owner, will likely be used in conjunction with the day-to-day use of the cellphone.

The cellphone and/or the cellphone protective cover and/or the cellphone screen, front or back protective cover and/or the cellphone stylus and/or other cellphone add-on and/or any combination thereof, operate in concert to provide a cellphone owner with the day-to-day ability to carry, protect and use the cellphone in a manner best suited to its owner. According to the gist of the present invention, this day-to-day ability to carry, protect and use the cellphone in a manner best suited to its owner must be substantially unchanged by the addition of the DRD detection system, rendering the cellphone and/or the cellphone protective cover and/or the cellphone screen, front or back protective cover and/or the cellphone stylus and/or other cellphone add-on and/or any combination thereof a DRD detection device.

As discussed hereinabove, one of the primary objectives of the present invention is to offer a practical solution for detecting DRDs by introducing a device that can seamlessly replace a regular cellphone in daily activities, whereas this substitution is intended to minimize the likelihood of the device being left behind when it's required for DRD detection. To achieve this objective, in some embodiments the device is preferably designed to resemble, at least to some degree, the conventional form-factor of a regular cellphone. In other words, the device's physical appearance and size are structured to be familiar and consistent with that of an ordinary cellphone. This approach ensures that users are more likely to carry the device consistently and without any extra effort or attention, as they would with their regular cellphone. This design choice not only enhances the device's accessibility but also increases the likelihood of its effectiveness in real-world situations where quick and inconspicuous DRD detection is paramount. By emulating the form-factor of a common cellphone, the invention aligns its functionality with the convenience and ubiquity of day-to-day mobile devices, thereby increasing its potential for widespread and effective use.

The term "form-factor", as used in the context of the device provided herein, refers to the physical size, shape, weight, dimensions, and overall appearance of the device. It encompasses the external design and layout of the device, including its visual aesthetics, proportions, and how it physically fits and interacts with the user and its environment.

Since one of the objectives of the present invention is to provide a device for DRD detection that in practice replaces an ordinary cellphone for ordinary day-to-day usage, so as to lower the chance of it not being on person when needed, the device is configured to exhibit a form-factor of an ordinary cellphone, at least to some extent. For example, for any given cellphone in the device, the device is said to have a form-factor of the cellphone if:

the overall thickness of the device is less than 150% of the thickness of the cellphone, or less than 140%, less than 130%, less than 120%, or less than 110% of the thickness of the cellphone; and/or the overall width of the device is less than 150% of the width of the cellphone, or less than 140%, less than 130%, less than 120%, or less than 110% of the width of the cellphone; and/or the overall length of the device is less than 150% of the length of the cellphone, or less than 140%, less than 130%, less than 120%, or less than 110% of the length of the cellphone; and/or the overall weight of the device is less than 150% of the weight of the cellphone, or less than 140%, less than 130%, less than 120%, or less than 110% of the weight of the cellphone;

and any combination thereof.

In some embodiments of the present invention, a DRD detecting system, or any major part thereof, would typically be sufficiently small, so that it can be easily be physically associated with the cellphone and/or the cellphone protective cover and/or the cellphone screen, front or back protective cover and/or the cellphone stylus and/or other cellphone add-on and/or any combination thereof, without substantially increasing the overall dimensions or weight or substantially distorting the shape of the cellphone the cellphone protective cover, the cellphone screen, front or back protective cover, the cellphone stylus and/or other cellphone add-on and/or any combination thereof.

As used herein the phrase "without substantially increasing the overall dimensions" means less than 50%, 40%, 30%, 20% or less than 10% increase in any one or more dimension.

As used herein the phrase "without substantially increasing the overall weight" means less than 50%, 40%, 30%, 20% or less than 10% increase in weight.

As used herein the phrase "without substantially distorting the shape" means that the overall shape remains similar to the human eye, albeit optionally enlarged in one or more dimensions.

Other than physical dimensions, the device may also be designed to preserve the visual, pragmatic, functional and aesthetic design features of a cellphone, such as the color, material, roundness, shininess etc., without compromising functionality of the cellphone or the DRD detection system. In the context of a DRD detection system that is housed integrally or modularly in a cellphone protective cover or a cellphone add-on, constituting a physical addition to the cellphone's physical size, it is possible to engineer the design in a way that maintains the cellphone's overall visual appeal, practicality, functionality, and aesthetic aspects. This includes aspects like color, choice of materials, smooth contours, and surface finish. Importantly, this design adaptation should not negatively impact either the cellphone's regular functions or the effectiveness of the DRD detection system integrated within it.

This would make it convenient for users to carry the DRD detection device at all times; and use the DRD detection device by employing the DRD detection system therewith when so required, such as in a variety of social event settings or venues, including bars, clubs, friend gatherings and parties.

In some embodiments of the present invention, the DRD detection system would optionally use the cellphone's built-in sensors, display, energy power, processing (computing) power, connectivity (e.g., to connect to a remote server, e.g., a cloud, or to data connect to the DRD device itself suing, e.g., Wi-Fi or Bluetooth communication protocols) and memory to detect DRDs. This would reduce the cost of associating a DRD detection system with the cellphone, cellphone protective cover, the cellphone screen, front or back protective cover and/or cellphone stylus and/or other cellphone add-on and/or any combination thereof, either during production or purchase. As suggested above, the DRD detection system can employ the inherent accessibility of the cellphone to remote databases, network servers, and cloud service providers. These remote sources of digital data and data processing capabilities can be used to run software, draw input data, analyze results and identify the DRD using database search prompts. Irrespective if the software is stored and executed by the cellphone's CPU or remotely, as further delineated in greater details below, the software may comprise elements related to machine learning and bid data, such as artificial intelligence (AI) that was designed and specifically trained to assist in DRD detection and identification. The software, either local and/or remote, may include a library of chemical, physical and/or electrochemical properties of common or all known DRDs, which can be used to detect and identify the DRD in a tested beverage sample, if present or detect its absence. For example, the DRD detection device described herein may use its integrated detection system to generate spectra or electrochemical signal, which is compared to signals stored on a remote server using a trained AI based software stored and run on the cellphones CPU and/or the remote server or both, all as is further delineated in greater details herein below.

According to some embodiments, the cellphone, or the cellphone protective cover, or the stylus, or any other cellphone add-on, has an integral sensor and a dedicated software communicating with the sensor for detecting the at least one DRD. The device provided herein may incorporate a cellphone, or a cellphone protective cover, or a stylus, or any other cellphone add-on, equipped with an integrated sensor specifically designed for detecting at least DRD, which is seamlessly linked to dedicated software that facilitates communication with the sensor. A dedicated software may include a data library of physical and/or electrochemical properties of the at least one DRD. This integrated setup enables the accurate detection of DRDs, enhancing the device's functionality and effectiveness. The integral sensor and the dedicated software integration is engineered to identify one or multiple distinct DRDs, ensuring a comprehensive approach to detection. This advanced DRD detection system is configured to promptly notify the cellphone user regarding the presence or absence of any of the targeted DRDs. Furthermore, the system is designed to provide detailed information, including the specific chemical composition, common name, and potential street name abbreviations of the detected DRD. This comprehensive alert mechanism equips users with essential knowledge for making informed decisions about their safety and well-being.

The integration of an integral sensor and dedicated software, with components both on the cellphone or associated device and in the cloud, creates a robust DRD detection system. This system ensures accurate, versatile, and informative detection, contributing to the safety and security of users when assessing the contents of their beverages. A dedicated software integrated into the device enhances its functionality for detecting DRDs. It may be a sophisticated mobile application designed to work seamlessly with the integral sensor, which is the component responsible for collecting spectral data from beverage samples. This software operates both within the cellphone or associated device and in a remote location, typically in a cloud-based infrastructure.

The dedicated software's primary function is to process the spectral data received from the sensor, employing advanced algorithms and data analysis techniques (e.g., artificial intelligence). It handles large datasets efficiently, enabling the identification of spectral signatures associated with DRDs within the samples. The integration with the remote server in the cloud allows for extensive data processing capabilities, ensuring accurate and rapid analysis. One of the software's key features may be its ability to identify not just one, but multiple distinct DRDs. This multi-target detection approach adds versatility to the device, making it effective in detecting a range of potentially harmful substances. Upon analysis, the software promptly generates alerts for the cellphone user. These alerts convey crucial information, indicating the presence or absence of the targeted DRDs in the beverage sample. Moreover, the software may go a step further by providing detailed information about the specific chemical composition of the detected DRD, its common name, and even potential street name abbreviations. This comprehensive alert mechanism empowers users with vital knowledge, enabling them to make informed decisions about their safety and well-being.

In some embodiments of the present invention, the DRD detection system would be connected to the cellphone's data and/or voice connectivity. This would allow the device to access up-to-date information on DRDs, and to share test results with others, as well as the capacity for reaching out for help or to notify authorities via autodial and/or textual functions.

The device for detecting a DRD in a beverage or a sample thereof as provided herein, can have several possible configurations that include a cellphone and/or a cellphone protective cover and/or a cellphone screen, front or back protective cover and/or a cellphone stylus and/or a cellphone add-on and/or any combination thereof; and a detection system for detecting the DRD. The DRD detection system is physically associated with the cellphone and/or the cellphone protective cover and/or the cellphone screen, front or back protective cover and/or the cellphone stylus and/or the cellphone add-on and/or any combination thereof. The DRD detection system may be unified or decentralized, with parts in the cellphone and/or the cellphone protective cover and/or the cellphone screen, front or back protective cover and/or the cellphone stylus and/or the cellphone add-on and/or any combination thereof, as long as all its components are associated with the cellphone and/or protective cover without interfering with the normal operation of any of the functions of the cellphone and/or the cellphone protective cover and/or the cellphone screen, front or back protective cover and/or the cellphone stylus and/or the cellphone add-on and/or any combination thereof, hence preventing the ability or obviating and diminishing the need to disconnect the DRD detection system from the DRD detection device.

As can be seen in FIG. 1, DRD detection system 19, represented by a Criss Cross patterned area, is the area on which components, ingredients, or chemical reagents associated with the DRD detection assay and designed for generating a detectable effect when contacting at least one DRD are disposed.

In some embodiments of the present invention, the DRD detection system is designed for repeated uses, at least for negative results, optionally also for positive results. In some embodiments, the DRD detection system is designed for repeated uses only for negative results. In such embodiments, the DRD detection system does not require replacement of any of its parts at least if, or only if, after using the DRD detection system, the sample is found free of DRD. More specifically, the DRD detection system can be reused at least if or only if none of its components, ingredients, or chemical reagents were consumed, reacted, or otherwise became irreversibly spent as a result of encountering at least one DRD in the tested sample.

A Unified DRD Detection System:

A unified DRD detection system is a configuration where the DRD detection system for detecting the DRD, or a major part thereof, is a single, integrated unit that is physically associated with the cellphone and/or the cellphone protective cover and/or the cellphone screen, front or back protective cover and/or the cellphone stylus and/or the cellphone add-on and/or any combination thereof. A unified DRD detection system typically contains all or most of the necessary components for detecting the DRD, including sensors, signal processing circuitry, and display. In some embodiments, the DRD detection system is a unified DRD detection system, namely the DRD detection system for detecting the DRD is unified and housed within or on the cellphone and/or the cellphone protective cover and/or the cellphone screen, front or back protective cover and/or the cellphone stylus and/or the cellphone add-on and/or any combination thereof. Other than being physically associated with the cellphone and/or the cellphone protective cover and/or the cellphone screen, front or back protective cover and/or the cellphone stylus and/or the cellphone add-on and/or any combination thereof, the DRD detection system may also be in data communication with the cellphone via wire or wireless (e.g., Wi-Fi, Bluetooth, GSM) communication.

Figure 2:
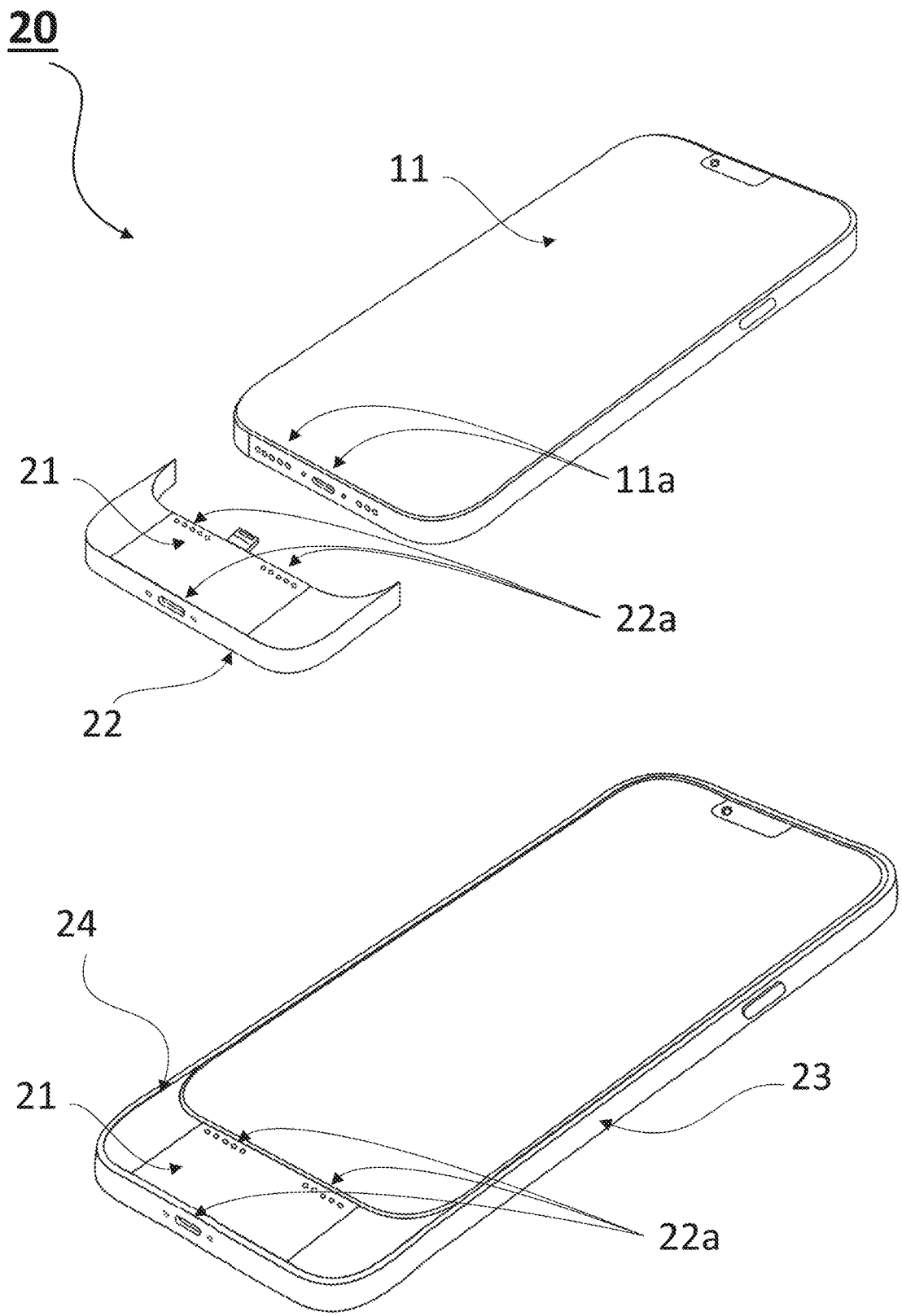

FIG. 2 presents a non-limiting example of a DRD detection device 20, that includes cellphone 11 having various ports 11a, and unified DRD detection system 21, implemented as add-on 22 that physically connects to cellphone 11 and having various replacement ports 22a, or implemented in cellphone protective cover 23 in the form of case 24 having various replacement ports 22a.

A Decentralized DRD Detection System:

A decentralized DRD detection system for detecting the DRD is divided into more than one component that are associated or inherent to the cellphone and/or cellphone protective cover and/or the cellphone screen, front or back protective cover and/or cellphone stylus and/or other cellphone add-on and/or any combination thereof. This configuration allows for more flexibility in the design of the DRD detection system, as different components can be optimized for different tasks. For example, one component could be responsible for collecting samples of beverage suspected as optionally tempered with a DRD, while another component could be responsible for analyzing the samples and yet still another component could be responsible for providing a readout, other functions are not omitted. In some embodiments, the DRD detection system is a decentralized detection system, namely the DRD detection system for detecting the DRD is designed to have some components thereof in the cellphone and parts in any of the covers, whereas some components can communicate with the cellphone via wire or wireless communication.

In some embodiments of the present invention, a decentralized detection system includes a module that contain some of the components of the DRD detection system, while other components of the DRD detection system are located elsewhere or are integral components of the cellphone. For example, the decentralized detection system may include an analytical tool that is associated with the back side of the cellphone protective cover, and that measures various chemical/physical/electrochemical properties associated with at least one DRD in a sample of a tested beverage, and further includes a power source in the form of the inherent power source of the cellphone, a display unit in the form of the inherent screen of the cellphone, and data communication inherent to the cellphone.

Replacement Components:

According to some embodiments of the present invention, in the case where the DRD detection system prevents the day-to-day original use of any of the functions of the cellphone and/or the cellphone protective cover and/or the cellphone screen, front or back protective cover and/or the cellphone stylus and/or other cellphone add-on and/or any combination thereof, a replacement component for replacing the lost function will be provided. For example, if the DRD detection system is physically connected to the cellphone via a data and/or power port, the DRD detection system will include a replacement data and/or power port replacing the original port, so as to preserve and allow the day-to-day original use of any of the functions of the cellphone, thereby obviating or diminishing the need to physically disassociate the DRD detection system for exercising day-to-day use of the cellphone. Similarly, if the DRD detection system is associated with the cellphone protective cover, is will retain the original functions of the cover, namely, covering and protecting the cellphone from physical damage, and optionally, additional preferred functions of the cover, such as but not limited to, inter alia, extra power source for powering the cellphone with additional power, mechanism for allowing wireless charging of the cellphone while being protected by its cover, credit card or identification card or business card or money internal or external pocket, embedded pepper spray container and discharge mechanism, shocker electrodes, their associated power supply or connecting mechanism to the integral power supply of the cellphone, a paper clip, a belt clip and/or epinephrine container and its discharge mechanism. Still similarly, the DRD detection system will not permanently block the flash, back or front camera lenses, functioning physical buttons of the cellphone and/or touch screen sensitivity or clarity, among other. A DRD detection system applied onto the cellphone screen or cellphone screen protective cover will not interfere, when not in use, with screen brightest, tactile feeling and tactile sensitivity. A DRD detection system applied onto the cellphone back protective cover shall not impair its physical rigidity. A DRD detection system applied onto the cellphone stylus shall not impair its physical rigidity, its tactile feel and/or stylus activity. A DRD detection system physically associated to any other cellphone add-on will retain the add-on day-to-day functionality.

As can be seen in FIG. 2, cellphone 11 exhibits various ports 11a, while add-on 22, housing unified DRD detection system 21, and/or cellphone protective cover 23 of case 24 that physically connects to cellphone 11, correspondingly exhibit various replacement ports 22a.

In some embodiments, the DRD detection system includes at least one component that is an inherent component of a cellphone, such as a power source, light source and sensors and processors and/or communications means that are built into most modern cellphones.

In another example of some embodiments of the invention, the cellphone's computing system and its corresponding memory and/or screen can be employed to conduct at least part of the process for detecting the DRD, identifying the DRD and executing post-detection steps, such as notifying the user, a pre-designated person or authority.

According to some embodiments of the invention the DRD detection system may include elements which are inherent to the cellphone, in some embodiments all the hardware elements and optionally some general-purpose software elements of the DRD detection system are inherent to or integrated in the cellphone, provided that at least one element of the hardware and/or software used to detect the DRD are not inherent to a regular cellphone devoid of DRD layman detection capabilities. For example, a DRD detection dedicated purchasable and/or downloadable application from an application store such as the Apple® or the Galaxy® store that allows in combination with the other components described herein detection of a DRD may be the sole addition to an existing cellphone, which application is designed to operate general purpose hardware and software components of the cellphone, which are used in the day-to-day operation of the cellphone to render the cellphone capable of detecting DRDs and reporting of their presence or absence. Importantly, in this exemplary embodiment no objects or chemicals are not physically associated with the cellphone and/or the cellphone protective cover and/or the cellphone screen, front or back protective cover and/or the cellphone stylus and/or the cellphone add-on and/or any combination thereof are to be used, unless readily available in any social venue in which beverages are available, such as a straw or beverage mixer which can be used as beverage sampling devices, or white napkin, which can be used as white back screen or absorbing pad for enhancing the visual detection of e.g., a colorimetric reaction formed when a DRD is present in tested beverage sample, as this would be counterproductive to the overall gist of the present invention.

For example, in embodiments wherein the DRD detection assay, executed by using the DRD detection system, is based on a colorant release (e.g., bleeding) into a beverage or a sample thereof, a napkin can be used as a blank bright background for facilitating the determination of a color change/bleed, as well as to wipe at least parts of the DRD detection system for readying it for another assay.

In some embodiments, the DRD detection system is physically associated with the cellphone and the cellphone protective cover.

In some embodiments, the DRD detection system is physically associated with the cellphone and the cellphone screen, front or back protective cover and/or the cellphone stylus and/or the cellphone add-on and/or any combination thereof.

In some embodiments, the DRD detection system is physically associated with the cellphone protective cover and the cellphone screen, front or back protective cover.

According to some embodiments of the present invention, the DRD detection device includes a DRD detection system that is physically associated:
(a) in part with the cellphone and in part with the cellphone protective cover;
(b) in part with the cellphone and in part the cellphone screen, front or back protective cover;
(c) in part with the cellphone protective cover and in part the cellphone screen, front or back protective cover;
(d) in part with the cellphone and in part the cellphone protective cover and in part the cellphone screen, front or back protective cover;
(e) in part with the cellphone and in part the cellphone stylus; and/or
(f) in part with the cellphone and in part with the other cellphone add-on.

Thus, according to some embodiments of the invention, the DRD detection device disclosed herein may be provided in several alternative configurations that include, without limitation:

i. A device in which the DRD detection system is physically associated with a cellphone. For example, a spectra meter or electrochemical sensor/detector or any other suitable electronic detector capable of detecting a DRD either inherent to the cellphone or connected thereto in a connection that allows the day-to-day use of the cellphone without disassociating the DRD detection system.

ii. A device in which the DRD detection system is associated with a cellphone protective cover. For example, a spectra meter or electrochemical detector or any other suitable electronic detector capable of detecting a DRD either inherent to the cellphone protective cover or connected thereto in a connection that allows day-to-day use of the cover and cell phone disassociating the DRD detection system therefrom.

iii. A device in which the DRD detection system is associated with a cellphone, cellphone protective cover, a cellphone screen, front or back protective cover, a cellphone stylus or cellphone add-on, for example, by applying directly or indirectly (e.g., via a sticker) chemical reagents thereon or therein, suitable for detection of at least one DRD.

iv. A device in which the DRD detection system is decentralized over the cellphone and the cellphone protective cover(s). For example, the DRD detection system includes a spectra meter in the cellphone protective cover and a spectra data analysis software suitable for detecting a DRD and general hardware in the cellphone.

v. A device in which the DRD detection system is physically associated with a cellphone, cellphone protective cover, a cellphone screen, front or back protective cover, cellphone stylus and/or other cellphone add-on, for example, by applying directly or indirectly (e.g., via a sticker) chemical reagents suitable for detection of at least one DRD via a bleeding colorimetric reaction on either one or more of the covers, stylus and or add-on and a spectrophotometer and software suitable for detecting a DRD by a layman on the cellphone and/or the cellphone protective cover.

vi. A device in which the DRD detection system is decentralized over the cellphone and the cellphone screen, front or back protective cover. For example, the DRD detection system includes an inherent spectra meter within the cellphone (e.g., involving light emanating from the cellphone's screen) as well as spectra data analysis software, and the cellphone screen or the cellphone screen, front or back protective cover is covered with transparent solid phase chemistry substrate layer that produces a signal when illuminated in the presence of the DRD, ensuring the substrate layer does not interfere with the cellphone screen or screen cover day-to-day functionalities (e.g., light emission, touch sensitivity and tactile feeling).

vii. A device in which the detection DRD system is decentralized over the cellphone protective cover and the cellphone screen, front or back protective cover. For example, the DRD detection system includes two types of colorimetric assays which are not compatible and require physical separation, therefore the cellphone screen, front or back protective cover includes chemistry of one type of assay, and/or for detecting some types of DRDs, and the cellphone screen, front or back protective cover includes chemistry for other types of assays, and/or for detecting other types of DRDs, wherein the respective chemical reagents can form a part of a printed layer or an adhesive sticker.

viii. A device in which the DRD detection system is decentralized over the cellphone, the cellphone protective cover and the cellphone screen, front or back protective cover. For example, the cellphone includes an inherent spectra meter, software and connectivity, and the covers each includes different chemical reagents for different DRD detection assays, wherein the chemical reagents can form a part of a printed layer or an adhesive sticker, whereby a colorant release (e.g., bleeding) in any of the assays in the presence of a respective DRD into a drop of a tested beverage can be detected, if present, using the spectra meter.

Figure 4:
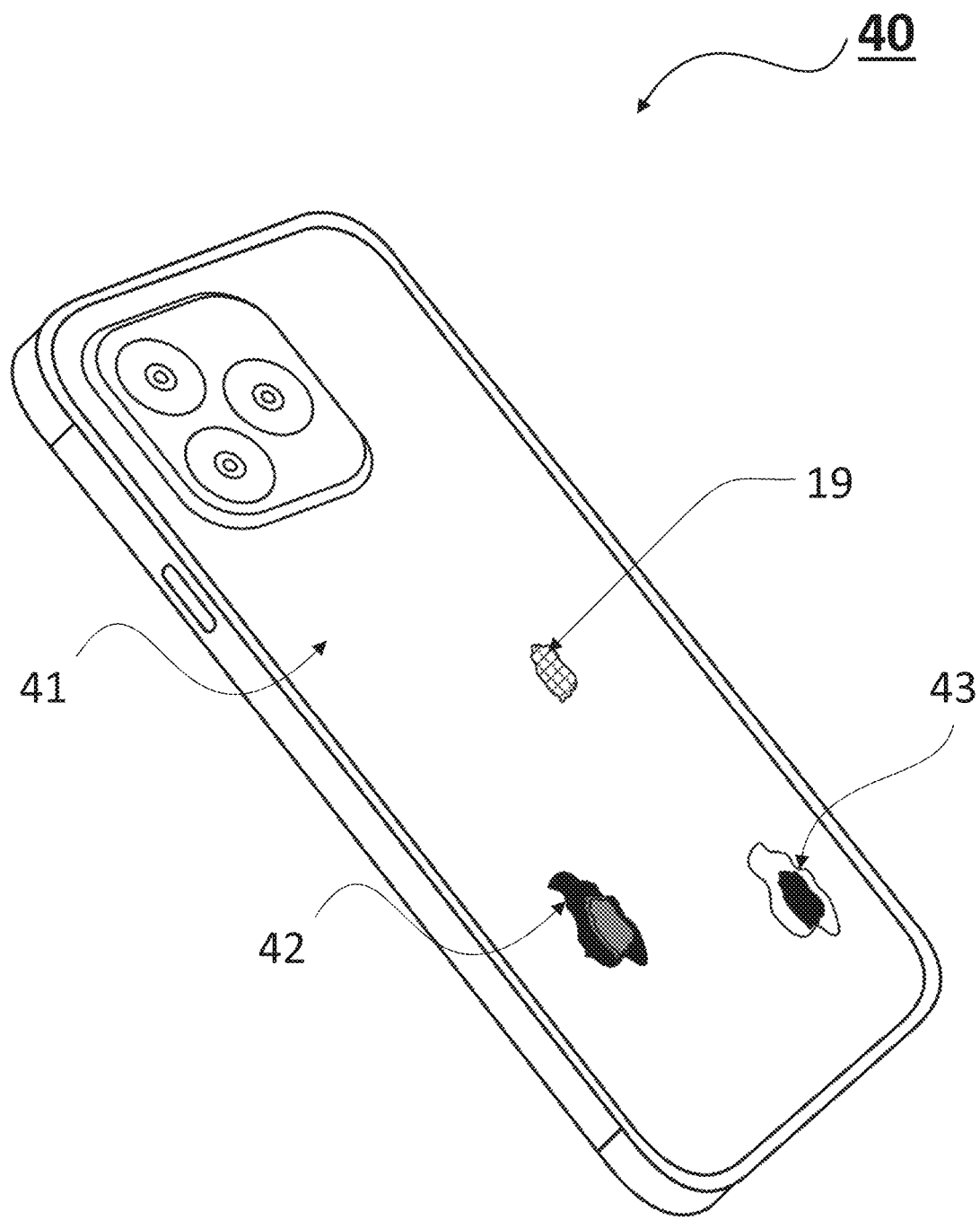
FIG. 4 presents a non-limiting embodiment of DRD detection device 40, as provided herein, implemented as cellphone back cover 41 physically associated with a cellphone and exhibiting DRD detection system 19 (as in FIG. 1) that is physically associated with a cellphone (obscured in the figure by cellphone back cover 41), wherein DRD detection system 19 is directly applied on cellphone back cover 41 and exhibits chemical reagents suitable for detection of at least one DRD via bleeding colorimetric reaction 42, and/or color change colorimetric reaction 43.

FIG. 4 presents a non-limiting embodiment of DRD detection device 40, as provided herein, implemented as cellphone back cover 41 exhibiting DRD detection system 19 (as in FIG. 1) that is physically associated with a cellphone (obscured in the figure by cellphone back cover 41), wherein DRD detection system 19 is directly applied on cellphone back cover 41 and exhibits chemical reagents suitable for detection of at least one DRD via bleeding colorimetric reaction 42, and/or color change colorimetric reaction 43.

Spectra Meter:

As used herein, the term "spectra" refers to plural form of the term "spectrum." As used herein a spectrum refers to the distribution of electromagnetic radiation or particles or molecules according to their wavelengths, energies, size or any other physical or chemical property or physical and chemical property, which provides a unique distribution pattern providing a characterizing physical and/or chemical signature presentable in a graph, to a chemical or mixture of chemicals for which a spectrum is determined. Thus, a spectrum is a representation of the different components, properties or frequencies present in a complex signal. Spectra can be observed in various scientific fields, such as optics, spectroscopy, mass spectrometry, chromatography and other, where they provide valuable information about the properties and composition of substances or phenomena. Hence the term "spectra meter" is used herein to describe a device which can detect spectra.

A very useful spectra meter is a spectrophotometer which is an instrument used to measure the intensity of light at different wavelengths in a given electromagnetic spectrum. It is commonly used to analyze the spectral composition of light emitted, transmitted, or reflected by a tested sample. Pertinent to some embodiments of the present invention, a spectrophotometer works by dispersing light into its component wavelengths, typically using a diffraction grating or a prism, or by using narrow wavelength light sources (typically LEDs). The dispersed light is then measured by a detector, such as a CCD (as in a digital camera) an active pixel sensor (CMOS), photodiode array or a photomultiplier tube, to generate a light spectral data. Light spectral data provides information about the distribution of light intensities at different wavelengths, which can be correlated to the unique spectral characteristics (a unique physical property) of substances such as DRDs in the sample being analyzed.

In some embodiments of the invention, the DRD detection system may include or use elements that are inherently present in contemporary cellphones and smartphones, as well as elements that are unique to the intended use of the DRD detection system. For example, cellphones typically comprise an integrated electric power source (a battery), an integrated light source (e.g., a screen, a camera flash light, etc.), and an integrated light sensor (e.g., a camera, an ambient light sensor), an integrated display for presenting information, an integrated sound producing element for sounding an alarm, an integrated motor for generating vibration as another form of alarm, an integrated computing system, integrated non-transient and transient memory, integrated data storage capacity and various integrated communication systems, all of which can be seen as part of the DRD detection system, and/or may be used for carrying out the detection of a DRD in a sample of a beverage and/or communicate the result to a user, and therefore can be seen as part of the DRD detection system, as long as at least one software and/or hardware component is specifically designed to detect the DRD and further as long as all components required for the detection of the DRD are dedicated and so designed for DRD detection by a laymen and are associated with the cellphone and/or a cellphone protective cover and/or a cellphone screen, front or back protective cover and/or cellphone stylus and/or other cellphone add-on and/or any combination thereof, or that are readily available is a beverage serving avenue (e.g., napkin, straw and/or beverage mixer).

In another example, a combination of chemical reagents capable of detecting the presence or absence of at least one DRD colorimetrically, are physically associated with the cellphone and/or the cellphone protective cover and/or the cellphone screen, front or back protective cover and/or cellphone stylus and/or other cellphone add-on and/or any combination thereof, wherein a chemical reaction that generates a colorimetric response in the presence of the DRD or not in its absence, is tested with a spectral meter which is physically associated with the cellphone or cellphone protective cover. In this example, the spectra meter can be the actual camera feature of the cellphone as different colorimetric reactions have visible light properties detectable quantitatively or qualitatively be the cellphone camera, with or without the use of the flash light of the telephone depending on ambient lighting.

In all the embodiments described hereinabove and below the gist of the present invention is strictly maintained, namely, none of the components of the DRD detection system interferes with the day-to-day use of the cellphone and/or the cellphone protective cover and/or the cellphone screen, front or back protective cover and/or cellphone stylus and/or other cellphone add-on and/or any combination thereof.

In some embodiments of the invention which require elements that are not typically found in cellphones, such as a sample containing member, a spectra meter, an electrochemical or other detector useful in DRD detection, a light source of a specific range of wavelengths (e.g., UV or IR), such elements may be added to a cellphone or a cellphone protective cover during the manufacturing thereof, or post-production as an appendage thereof, provided that the day-to-day original use of any of the functions of the of the cellphone and/or the cellphone protective cover and/or the cellphone screen, front or back protective cover and/or cellphone stylus and/or other cellphone add-on and/or any combination thereof, with which the DRD detection system or any of its components is physically associated with will be either retained or alternatively replaced by similar components and/or functions provided with the DRD detection system.

The DRD detection system for detecting a DRD may require a source of energy to operate. Such a source of energy may be a battery. In some embodiments, the battery is embedded in the cellphone and used for cellphone operation as well as for the operation of the DRD detection system. In some embodiments, the DRD detection system uses a battery designated solely for its operation. The designated battery may be coupled to a charging mechanism of the cellphone and/or a wireless charging mechanism and/or an independent charging mechanism that operates concomitantly which the charging mechanism of the cellphone or a cellphone protective cover that carries an extra external battery. The DRD detection system may require a source of energy to execute one or more of the steps in a DRD detection assay. For example, a source of energy is needed to heat a sample, to illuminate a sample, to sense and record radiation (e.g., light, particles) emitted during the DRD detection assay, and/or to run software, diagnostics, communications etc. needed to complete the assay, analyze and display its results.

In some embodiments, the DRD detection system for detecting a DRD may operate without a source of energy altogether. For example, the DRD detection system configured to execute a DRD detection assay that is based on a chemical reaction that changes a color of an indicator in an element of the DRD detection system, whereas no source of energy is needed to drive the chemical reaction or to identify the change in color, analogue to the operation of litmus, which is a water-soluble mixture of different dyes absorbed onto filter paper to produce one of the oldest forms of pH indicator, used to test materials for acidity. This DRD detection system which is chemical in nature may be applied directly or indirectly onto the cellphone screen, front or back, alternatively, to the cellphone protective cover, and/or to the cellphone screen, front or back protective cover, the cellphone stylus and/or the other cellphone add-on while not interfering with their day-to-day use and functions.

In some embodiments, the DRD detection system includes various cellphone elements and systems that are present in any typical cellphone, as well as elements that can be added to the cellphone and/or the cellphone protective cover and/or the cellphone screen, front or back protective cover and/or the cellphone stylus and/or other cellphone add-on and/or any combination thereof.

One of the advantages of the DRD detection device provided herein, is the fact that it forms a part of the cellphone and/or the cellphone protective cover and/or the cellphone screen, front or back protective cover and/or cellphone stylus and/or other cellphone add-on and/or any combination thereof, which is or substantially permanently engaged with a communication device. According to the invention, the entire device including all its components and/or reagents, are present in or on a cellphone and/or a cellphone protective cover and/or a cell phone screen, front or back protective cover and/or a cellphone stylus and/or other cellphone add-on and/or any combination thereof, wherein the device is fully operable both as a cellphone and as a device for detecting DRD while all the DRD detection system are physically associated therewith.

In some embodiments which require the use of a light filter for selecting specific wavelength(s), or a background object exhibiting a specific background color (e.g., white and/or reflective), such as often needed in certain spectroscopic assays, the filter and/or background object are/is stored on the cellphone or the protective cover held by a designated mount or a holder (e.g., a n adherable or magnetic pad) and/or placed in a pocket or receptacle attached to the cellphone and/or the cellphone protective cover and/or the cellphone screen, front or back protective cover and/or cellphone stylus and/or other cellphone add-on and/or any combination thereof. In some embodiments for generating a white background a user can use a white napkin typically providable in bar or pub venues as well in other social events in which beverages are served. In addition, other instruments found in social events in which beverages are served such as straws and beverage mixer sticks can be used for sampling a beverage to be detected for DRD(s) by the DRD detection system used in context of the present invention.

The DRD detection system of the DRD detection device provided herein may be configured to execute, and report the results of the DRD detection assay completely independently from the inherent capabilities of the cellphone, namely the DRD detection system is independent and does not rely on any provisions from the cellphone, other than being physically associated with the cellphone and/or is various protective covers, while allowing their day-to-day use as well. In some embodiment, the DRD detection system is configured to have communication with the cellphone and/or to operate in communication with the cellphone. Under communication with the cellphone, the DRD detection system may be configured to send commands to the cellphone via an application or directly via the cellphone system. The communication with the cellphone may include downloading data from the internet or other remote servers that is pertinent to the DRD detection, and/or upload the results of an assay conducted and obtained by the DRD detection system for analysis elsewhere, and/or send the results to a third party.

By "communicating" in this context it is meant that the DRD detection system may use the cellphone's communication capabilities to execute an action by the cellphone, such as, without limitation, displaying information pertaining to a detection of the DRD, sounding an audible or vibrational alarm pertaining to a detection of the DRD, place a cellphone call and/or text message to a designated receiver, such as police, authorities and/or parents, for notifying the designated receiver to a detection of the DRD.

In some optional embodiments, the DRD detection device provided herein may also be designed and configured to comply with, or overcome challenges and complications that can optionally be considered when contemplating a small, portable device for detecting DRDs in a beverage, such as a cocktail drink, under the settings of a public establishment, such as a pub or bar. These optional properties include:

Small size: The DRD detection device should be small enough to be carried on a person or in a carrying bag/purse that a person typically takes to such establishments.

High sensitivity: The DRD detection device must be sensitive enough to detect the presence of drugs at low concentrations. Drugs can be added to drinks in very small amounts, so the DRD detection device must be able to detect them even if they are diluted. Moreover, the beverage typically contains many other substances that may affect sensitivity and specificity.

Substance specificity: The DRD deletion device must be specific to the drugs that it is designed to detect. It should not give false positives for other substances, such as food coloring or other chemicals that may be present in drinks.

Speed: The DRD deletion device must be able to provide results quickly. People who have been drugged may not have much time to react, so the device must be able to detect the drugs and provide results in a matter of minutes.

Cost: The device must be affordable and accessible to people who may need to use it.

Durability: The DRD detection device must be durable enough to withstand the rigors of day-to-day use. It should be able to be carried around in a pocket or purse without being damaged.

Ease of use: The DRD deletion device must be easy to use, even for people who are not familiar with technology. It should have a simple interface that is easy to understand.

Privacy: The device should not be used to violate people's privacy.

Additional aspects that have been considered by the present inventor include:

The presence of other ingredients in the sample: beverages, such as cocktail drinks, typically contain a variety of ingredients, including alcohol, mixers, and flavorings. These ingredients can interfere with the detection of drugs, so the device must be able to account for them.

The concentration of drugs with respect to other ingredients: The concentration of DRDs in a drink can vary depending on the type of DRD, the amount of DRD that is added, and the time that the DRD has been in the drink. The device must be able to detect DRDs at a variety of concentrations, particularly low concentrations.

The temperature of the drink: The temperature of the drink can also affect the detection of DRDs that are more soluble in warm liquids than in cold liquids. The device must be able to detect drugs in drinks that are at a variety of temperatures, or be configured to set the temperature therein during the assay.

The turbidity of the drink: The turbidity of the drink refers to how cloudy or clear it is. Many popular beverages contain solid pieces of fruits, emulsions (e.g., milk) suspension of small particles (e.g., spices). Turbid drinks can make it difficult to detect drugs. The device must be able to detect drugs in drinks that are both clear and cloudy. The detection of a small molecule (a molecular weight of less than about 1,000 Daltons) at a relatively low concentration (0.2 to 2.0 μg/mL) found in a beverage that contains many other molecules, is challenging: some of the common ingredients of beverages may be found at a much higher concentration than the DRD, some with the capacity to alter the chemical behavior of a DRD in terms or via pH, solubility, and reactivity; some of the common ingredients of beverages are solids (e.g., fruit pulp) and gases (CO2).

The forgoing provide ample examples that overcome the above limitations and provide for the above properties.

A DRD Detection System

The phrase "detecting a DRD", as used herein, refers to providing the ability to infer if one or more DRDs are present or absent. More specifically, the phrase "detecting a DRD" refers to an assay designed and executed in order to determine the presence or absence of DRDs in a sample. The various DRD detection systems described herein are designed for detecting DRD, namely to infer the presence or absence of DRDs in a sample. The DRD detection system may use a variety of methods to detect DRDs, such as light spectroscopy, mass-spectroscopy, liquid and/or gas chromatography, or electrochemical detection. A method for detecting date rape drugs (DRDs) is a procedure that is designed to determine the presence or absence of DRDs in a sample. The method is effected by the DRD detection system provided herein, and may use a variety of techniques, such as light spectroscopy, mass spectroscopy, chromatography, or electrochemical detection.

The detection of DRDs involves various analytical methods and techniques to identify and quantify the drugs in samples, such as blood, urine, or beverages. These detection methods may include measuring or detecting physical phenomena, measuring or detecting chemical phenomena and measuring or detecting physio-chemical phenomena. The detection methods may be based on chromatographic techniques (e.g., gas chromatography, liquid chromatography), mass spectrometry, immunoassays, solid phase colorimetric assays, bleeding colorimetric assays, electrochemical sensors and detectors, or other specialized devices and assays.

The DRD detection system can be in the form of an area that is at least part of the surface of the cellphone and/or the cellphone protective cover and/or the cellphone screen, front or back protective cover and/or cellphone stylus and/or other cellphone add-on and/or any combination thereof, on which DRD detection chemical reagents have been applied directly or indirectly (e.g., via a sticker). The area of the surface can be in the form of a layer comprising a matrix substance, such as a polymer, and said chemical reagents disposed therein or thereon. The layer can be affixed to the surface by being formed thereon or formed elsewhere and affixed thereof. The layer can be formed, for a non-limiting example, by printing, e.g., digital printing, dipping, spraying, brushing, etc. The layer can be affixed to the surface, for a non-limiting example, as a sticker. The area can be designed to detect DRD by a color change, wherein contacting a sample of the beverage suspected in containing a DRD effects a visible change in the color of the contacted area and/or the sample (i.e., a colorant is disengaged or bleeds from the area upon contacting the DRD). The area can be designed to detect one or more DRDs. In embodiments that the chemical reagents for detecting different DRDs are compatible, such chemical reagents can be placed in the same area and detect more than one DRD by changing the color of the area or the sample—in some embodiments each DRD is detected by a different color change, and in some embodiments more than one DRD is detected by the same color change, in which case physical separation will also allow DRD identification.

As can be seen in FIG. 1, DRD detection system 19, represented by a Criss Cross patterned area, is the area that is at least part of a surface of each of the objects shown in the figure, that is physically associated therewith.

Detecting the presence of DRD in a beverage typically involves using analytical methods and reagents that can identify and optionally quantify the drugs present. Analytical methods in use today for the trace detection of small organic molecules, such as DRDs, are designed to follow one or more properties of the DRD, such as a chemical property (e.g., charge, acidity, receptor binding, etc.) or a physical property (e.g., mass, color, spectral emission/absorption, fluorescence, etc.). In some instances, the property of the DRD can be seen as both chemical and physical, or a subset of one, as in the case of an electrochemical property. In some embodiments of the present invention, the DRD detection system is designed to detect a chemical property of at least one DRD. In some embodiments of the present invention, the DRD detection system is designed to detect a physical property of at least one DRD. In some embodiments of the present invention, the DRD detection system is designed to detect an electrochemical property of at least one DRD. All these detection methods can be direct or indirect.

Chemical substance detection methods are based on electrochemistry, ion-mobility spectrometry, gas chromatography, HPLC, photoluminescence, surface acoustic-wave devices, microcantilevers, fluorescent polymers, surface plasmon resonance, quartz crystal microbalance, immunosensors and other methods. Some analytical methods and reagents commonly used for their detection include:

Immunoassays: Enzyme-linked immunosorbent assays (ELISA) and lateral flow immunoassays are rapid and sensitive methods that use specific antibodies to detect and quantify the presence of date rape drugs in a beverage;

Gas Chromatography-Mass Spectrometry (GC-MS): GC-MS is a powerful technique that separates and analyzes individual components in a sample. It can identify and quantify DRD based on their unique mass spectra. Gas chromatography is a more sensitive method than immunoassay, but it is not as specific, whereas gas chromatography is also more time-consuming than immunoassay;

Liquid Chromatography-Mass Spectrometry (LC-MS): LC-MS is similar to GC-MS but is used for compounds that are thermally labile or have limited volatility. It is also commonly used for DRD detection;

UV-Vis Spectroscopy: UV-Vis spectroscopy can be used to analyze the absorbance of date rape drugs in a beverage at specific wavelengths, allowing for qualitative and quantitative analysis; Fourier transform infrared-attenuated total reflectance (FTIR-ATR) is another type of spectroscopy that is currently used to detect DRDs; and Colorimetric Reagents: Some reagents can produce a color change when they come into contact with specific date rape drugs. These color changes can be visually detected, providing a quick screening method.

While some DRD detection methods are more accurate than others, some are only qualitative and some require elaborate facilities and expertise, some of the most effective DRD detection methodologies are currently:

Solid-phase assays, including immunoassay, constitute a rapid and relatively inexpensive family of methods that can be used to screen for the presence of drugs in beverages. Solid-phase chemistry (SPC) can be used to extract and concentrate target analytes from complex media. In the case of DRDs, SPC can be used to extract the DRD from fluids, such as a beverage, and the extracted DRD can then be analyzed by other methods, as discussed herein.

Electrochemical assays, including cyclic voltammetry (CV) assays, using an electrochemical sensor that is designed to specifically recognize and interact with a DRD of interest, producing characteristic electrochemical signals. Cyclic voltammetry is a technique that measures the current response of an electroactive DRD as a function of the applied voltage.

Some spectrophotometric assays measure the amount of light absorbed by a solution over a range of wavelengths. This allows for the identification and quantification of multiple substances in a single sample. Spectrophotometric assays are more complex than colorimetric assays per se, but they offer greater sensitivity and accuracy.

A Spectrophotometric Device:

Spectrophotometry is a branch of electromagnetic spectroscopy concerned with the quantitative measurement of the reflection or transmission properties of a material as a function of wavelength. Spectrophotometry uses photometers, known as spectrophotometers that can measure the intensity of a light beam at different wavelengths. Although spectrophotometry is most commonly applied to ultraviolet, visible, and infrared radiation, modern spectrophotometers can interrogate wide swaths of the electromagnetic spectrum, including x-ray, ultraviolet, visible, infrared, and/or microwave wavelengths.

Spectrophotometry is an analytical tool that is suitable for use in the DRD detection system, according to some embodiments of the present invention, as it relies on qualitative and/or quantitative analysis of molecules based on the amount of light absorbed by colored compounds in a sample. Spectrophotometry is commonly used to measure transmittance and/or reflectance of solutions, transparent or opaque solids, and gases. The key features of spectral meters include spectral bandwidth, which determines the range of colors the instrument can transmit through the sample, and the percentage of sample-transmission. Additionally, the logarithmic range of sample absorption and sometimes a percentage of reflectance measurement are important aspects.

One of the features of spectrophotometry that make it suitable for use in the DRD detection system for detecting DRDs is its versatility in analyzing both colored and colorless DRDs. While some DRDs are colored and can be directly measured using colorimetric procedures, some colorless DRDs can be converted to colored compounds suitable for chromogenic color-forming reactions, enabling colorimetric analysis. Spectral meters are designed to cover various spectral ranges, typically spanning from 200 to 2500 nm, and they require specific calibrations and controls depending on the photometric determination wavelength.

In the context of a DRD detection system for detecting DRDs, as provided herein, spectrophotometry is highly suitable since some of the essential components needed to construct a spectral meter are simple, small, cheap, and some are even found in any contemporary smartphone. There are two main types of spectrophotometers: single-beam and double-beam, and both types can be implemented in the device provided herein, according to some embodiments of the present invention. Single-beam spectrophotometers measure the light intensity before and after a sample is inserted. Double-beam spectrophotometers compare the light intensity between two light paths, one path containing a reference sample and the other the test sample. Double-beam spectrophotometers are more accurate and stable than single-beam spectrophotometers, but they are also more intricate and complex.

The DRD detection device provided herein may be based on a spectrophotometer that uses a monochromator to produce a spectrum of light. The monochromator can either be movable or fixed. If a single detector is used, the grating can be scanned stepwise so that the detector can measure the light intensity at each wavelength. Arrays of detectors can also be used; in which case the grating is fixed and the intensity of each wavelength of light is measured by a different detector in the array. In some embodiments where the device is making transmission measurements, the spectrophotometer quantitatively compares the fraction of light that passes through a reference solution and a test solution. For reflectance measurements, the spectrophotometer quantitatively compares the fraction of light that reflects from the reference and test samples.

In some embodiments, the device includes a light source, either specifically designed for the purpose of detecting a DRD, or based on the inherent light sources found in a typical smartphone. The light source is shone into a monochromator, which diffracts the light into a "rainbow" of wavelengths. The light is then split into two beams, one for the reference sample and one for the test sample. The beams are then passed through the samples and the detector measures the amount of light that is transmitted or reflected. The transmittance or reflectance value for each wavelength of the test sample is then compared with the transmittance or reflectance values from the reference sample. Most instruments will apply a logarithmic function to the linear transmittance ratio to calculate the 'absorbency' of the sample, a value which is proportional to the 'concentration' of the chemical being measured.

Spectroscopic Assays:

Spectroscopy is the field of study that measures and interprets the electromagnetic spectra that result from the interaction between electromagnetic radiation (e.g., light) and matter as a function of the wavelength or frequency of the radiation. Spectrophotometry is a branch of electromagnetic spectroscopy concerned with the quantitative measurement of the reflection or transmission properties of a material as a function of wavelength. Spectrophotometry uses spectral meters, known as spectrophotometers that can measure the intensity of a light beam at different wavelengths. Spectrophotometers can interrogate wide swaths of the electromagnetic spectrum, including gamma rays (10 µm to 10 nm), x-ray (10 nm to 100 pm), ultraviolet (100 pm to 400 nm), visible (400 nm to 700 nm), near infrared (NIR; 700 nm to 1 mm), short-wave infrared (SWIR; 1 mm to 2.5 mm), mid-wave infrared (MWIR; 2.5 mm to 25 mm), long-wave infrared (LWIR; 25 mm to 1 mm), terahertz (1 mm to 10 mm), and/or microwave radiation (1 mm to 30 cm).

Colorimetric assays, including fluorescence-based assays and other spectroscopy-related assays, measure the amount of light absorbed by a solution (the sample) at a specific wavelength, and rely on color changes to detect the presence of specific substances such as DRDs or a colorimetric response effected thereby in the sample. The wavelength of light that is absorbed is determined by the chemical properties of the substance being measured.

Fluorescence-based assays rely on the fact that some DRDs can fluoresce when is excited by light. The intensity of the fluorescence can be used to determine the presence and even the concentration of a DRD in the sample.

Absorption-based assays rely on the capacity of a DRD to absorb light at certain wavelengths. The amount of light absorbed by the DRD can be used to determine the presence and even the concentration of a DRD in the sample.

Colorimetric assays are often used to measure the concentration of compounds that have a characteristic color, such as the dye methylene blue. Colorimetric assays are relatively simple and easy to use, and can be used as a method for detecting DRDs in beverages according to some embodiments of the present invention. In the context of detecting DRD in a beverage, colorimetric tests can be used to identify the presence of certain drugs, including, without limitation, GHB, flunitrazepam, and ketamine.

A non-limiting example of a colorimetric sensor has been developed by Argente-Garcia, A. et al. ["*A passive solid sensor for in-situ colorimetric estimation of the presence of ketamine in illicit drug samples*", Sensors and Actuators B: Chemical, 2017, 253, pp. 1137-1144; incorporated herein by reference in its entirety] for the presumptive detection of ketamine in illicit drug samples. The sensor has been prepared by immobilized the reagent $Co(SCN)_2$ into polydimethylsiloxane (PDMS). When exposed to solutions of ketamine at a basic pH, the sensor color changes from brown to blue-purple due to the diffusion of the analyte molecules to the polymeric matrix and subsequent interaction with the reagent particles. The sensor enables the visual identification of amounts of drug as low as 30 μg in a few minutes. Quantification of ketamine is also possible through the measurement of the absorbance in diffuse reflectance mode. Under the proposed conditions, linear response was obtained up to concentrations of the ketamine of 1000 μg/mL (4.21 mM) with satisfactory precision (relative standard deviations, RDSs <10%). The reliability of the developed sensors has been tested by analyzing illicit drug samples.

A non-limiting example of nanobiosensors for detecting small amounts of drugs in a liquid sample, such as a beverage, or a biological fluid are described in a review by Razlansari, M. et al. ["*Nanobiosensors for detection of opioids: A review of latest advancements*", European Journal of Pharmaceutics and Biopharmaceutics, 2022, 179, pp. 79-94; incorporated herein by reference in its entirety]. In the context of some embodiments of the present invention, nanomaterial-based biosensors are useful tools to determine the presence of a drug at very small sample volumes, and can therefore be used in the DRD detection system for detecting a DRD. Nanobiosensors generally comprise a signal transducer nanostructure in which a recognition molecule, biological or otherwise, is immobilized onto its surface. Nanobiosensors have been extensively utilized for the molecular detection of opioids, and that usage of novel nanomaterials in biosensing has led to developing biosensors for other drugs of interest, such as DRD. Nanomaterials with sufficient surface area have been used to develop nanobiosensors with shorter reaction times and higher sensitivity than conventional biosensors.

Colorimetric and fluorescence sensing methods are two kinds of optical sensor systems based on nanomaterials. Noble metal nanoparticles (NPs), such as silver and gold, are the most frequently applied nanomaterials in colorimetric techniques, owing to their unique optical feature of surface plasmon resonance.

According to some embodiments of the present invention, some assays involve the use of chemical reagents that react with or are displaced by the DRD to produce a distinct signal, e.g., color change, whereas the color change indicates the presence of a DRD in the beverage or in a sample thereof. These reagents are referred to herein as colorimetric reagents.

Thus, in some embodiments, the DRD detection system for detecting a DRD is configured to operate as a colorimetric or a spectrophotometric assay detection system, whereas both methods require at least a light source which may include an optional wavelength filter, a light sensor acting as a detector configured to receive the light emitted by the light source after it passes through a sample, and a sample containing member for holding and illuminating a sample of the beverage. The detection includes having light emitted by the light source interact with the sample in the sample containing member, and read by the light sensor.

The DRD detection system may further include data storage (memory) and a processing system (software and hardware), for storing and processing spectral information pertaining to the DRD that links the result of the assay to a particular DRD.

As a small organic molecule, a DRD exhibits characteristic spectral signature pertaining to the interaction of its atomic structure with light of a certain wavelength or a range of wavelengths. The spectral data, that may be stored in the DRD detection system or remotely (e.g., cloud), includes spectral information pertaining to the spectral signature of any DRD, and the detection process includes comparison of the spectral signature obtained from the sample to the spectral information stored in the DRD detection system. The availability of spectral data pertaining to many other solutes and solvents, which are expected or known to be present in the beverage and potentially obscure the spectral signature of the DRD, permits using these data to improve the sensitivity of the DRD detection system to the DRD, by leveraging these data to enhance the sensitivity of the detection mechanism towards the DRD even when present in minute quantities within a beverage containing other major solutes and solvents. Spectral data of non-DRD solutes and solvents can be used in a designated spectral data processing software to lower the level of noise and/or to normalize the measured signal to deduct background noise and signals from non-DRD factors in the sample.

Figure 3A:
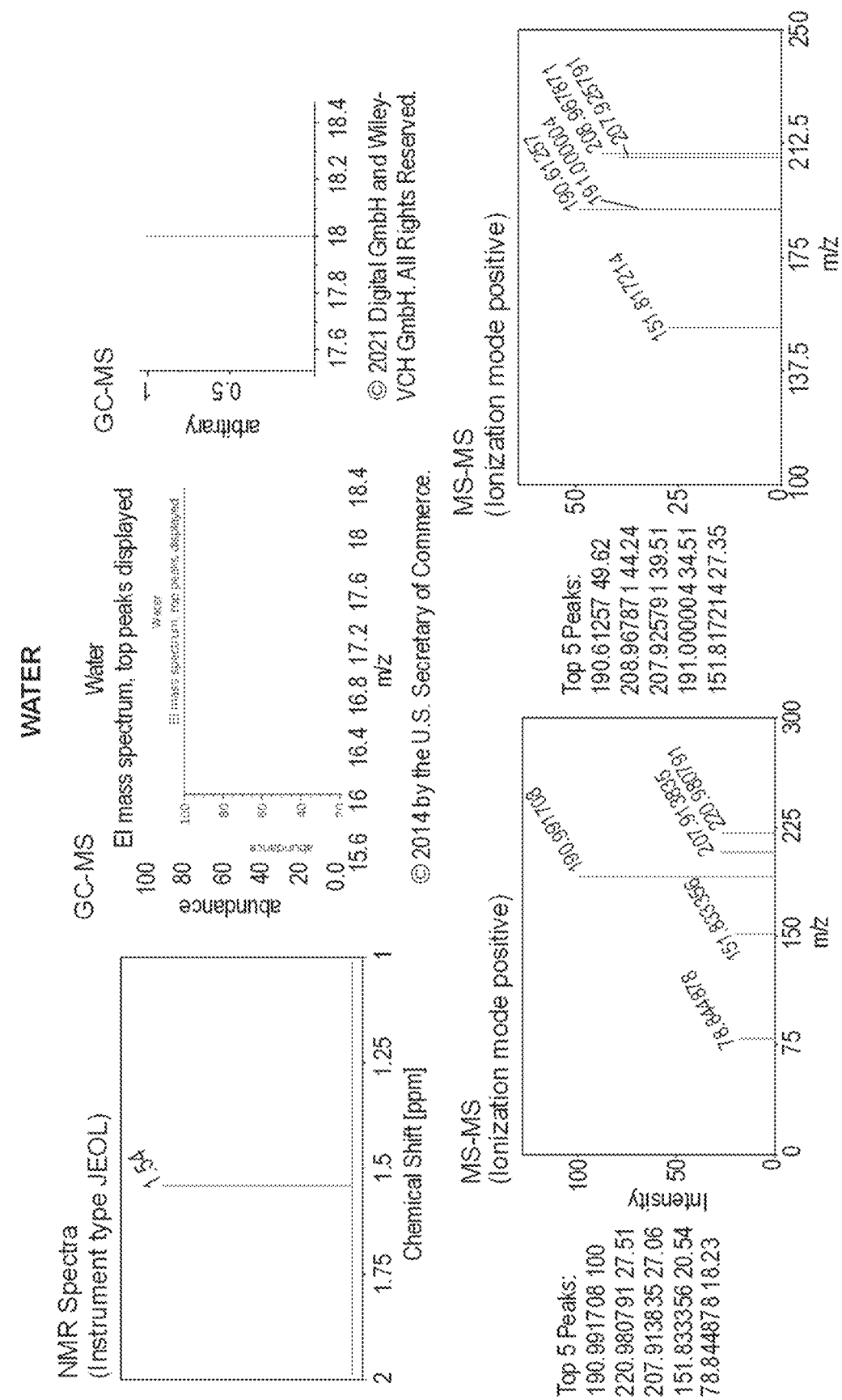
FIGS. 3A-J present spectral data of two major non-DRD solvents (water in FIG. 3A and ethanol in FIG. 3B) and spectral data pertaining to several DRDs (GHB in FIG. 3C, GBL in FIG. 3D, flunitrazepam (Rohypnol) in FIG. 3E, ketamine in FIG. 3F, methoxetamine (MXE) in FIG. 3G, MDMA in FIG. 3H, carisoprodol (Soma) in FIG. 3I, and diazepam in FIG. 3J), obtained from the publicly accessible source PubChem National Center for Biotechnology Information, U.S. National Library of Medicine [website: pubchem(dot)ncbi(dot)nlm(dot)nih(dot)gov]
Figure 3B:
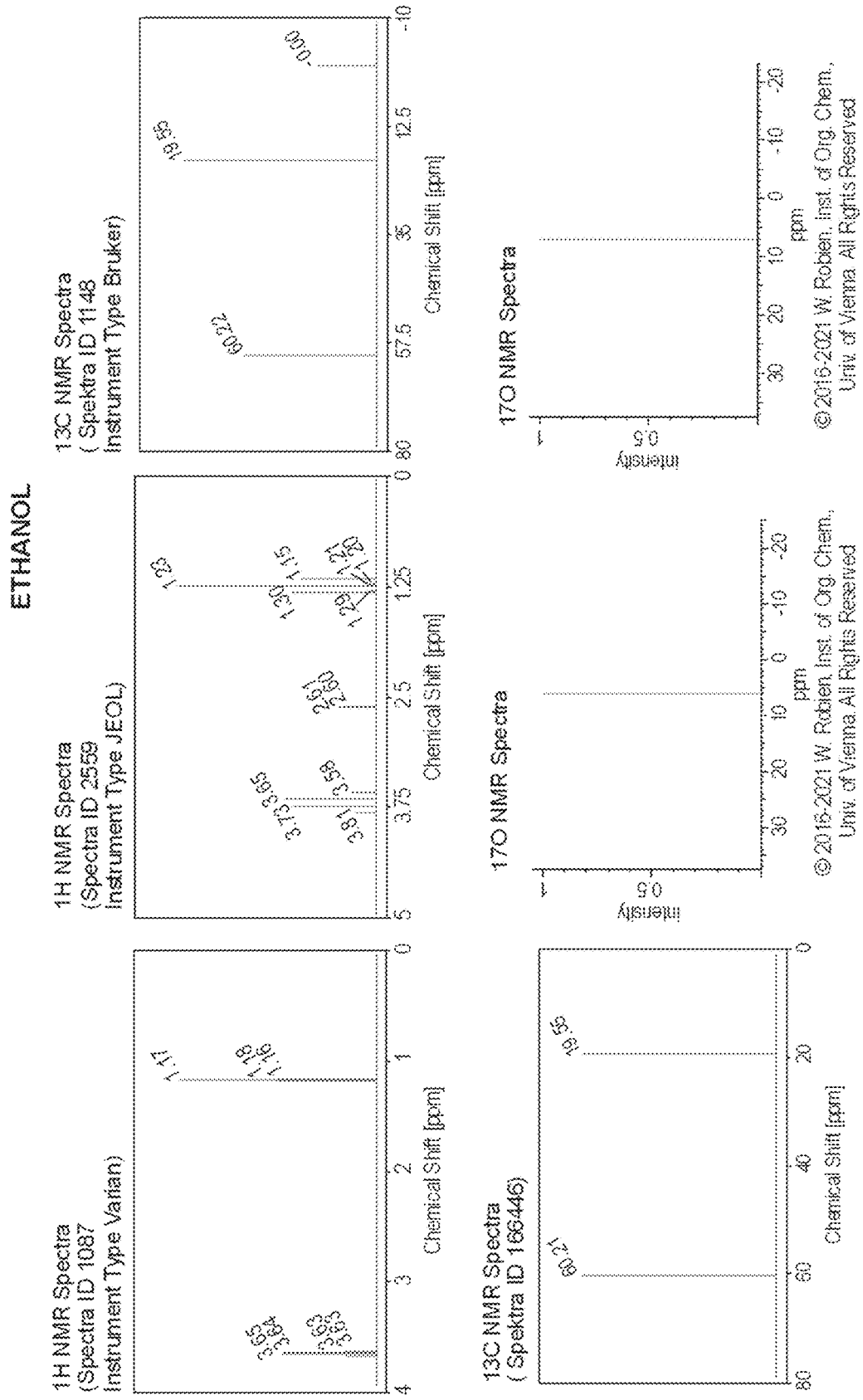
Figure 3C:
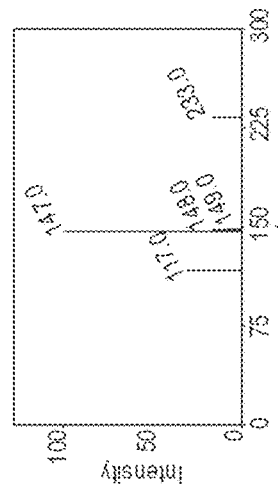
Figure 3C:
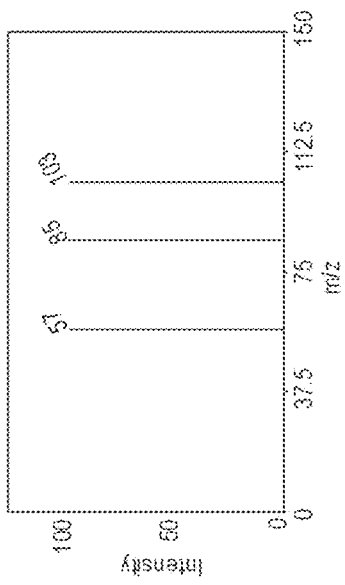
Figure 3C:
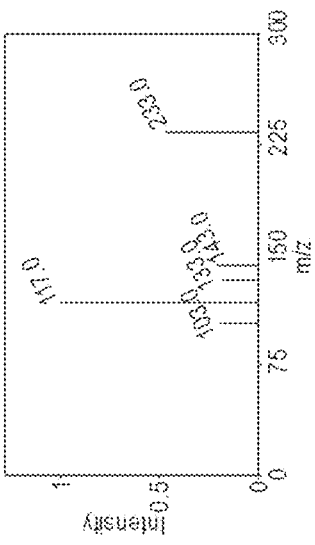
Figure 3C:
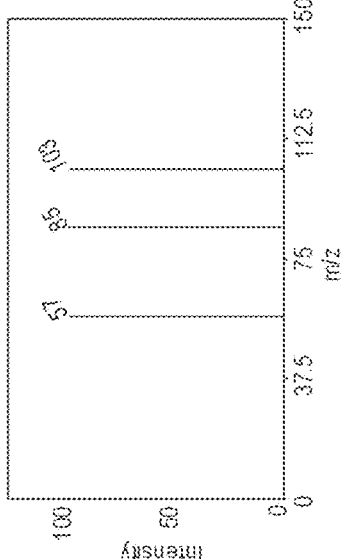
Figure 3C:
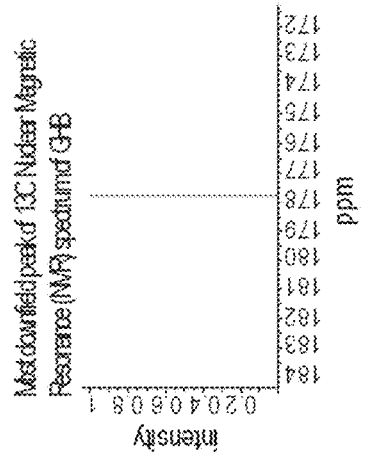
Figure 3C:
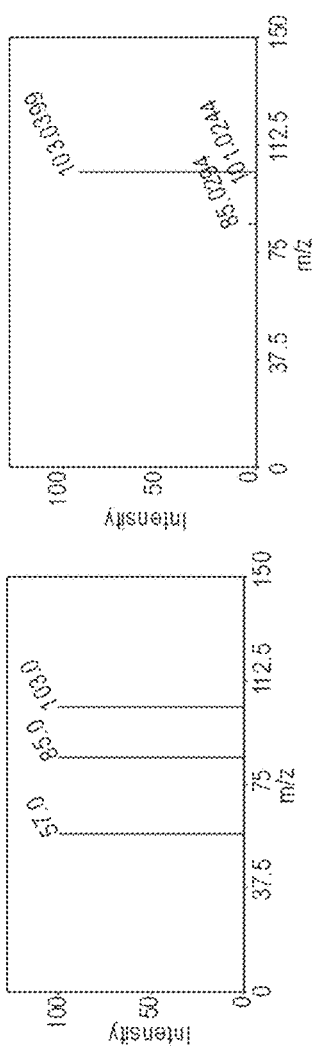
Figure 3D:
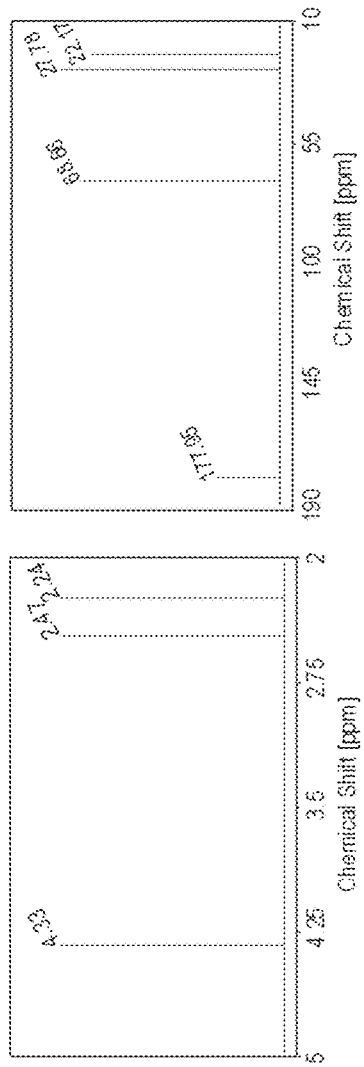
Figure 3D:
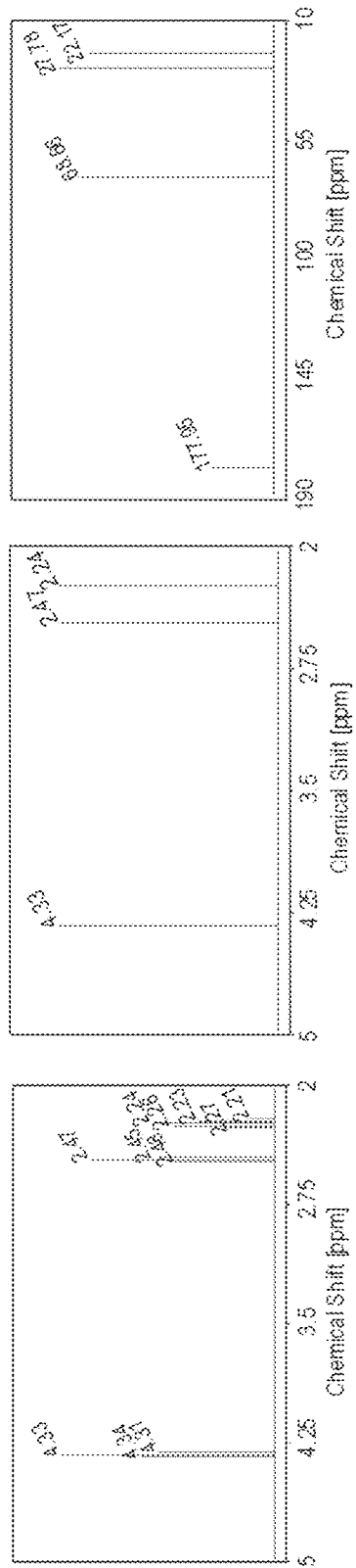
Figure 3D:
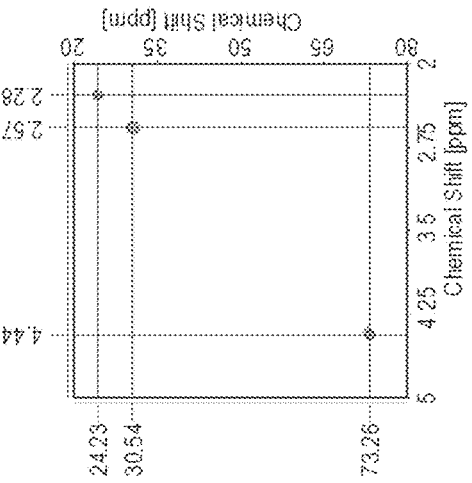
Figure 3D:
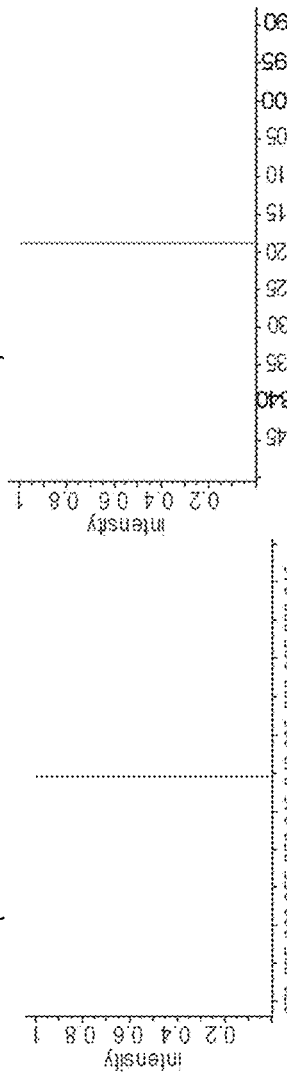
Figure 3E:
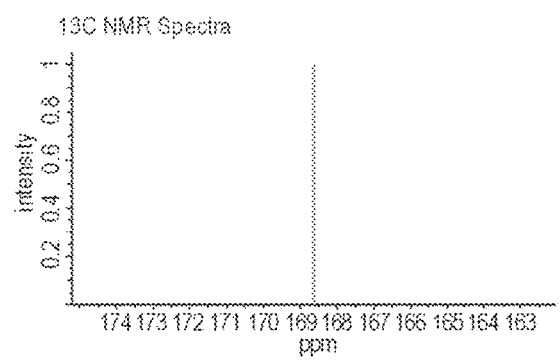
Figure 3E:
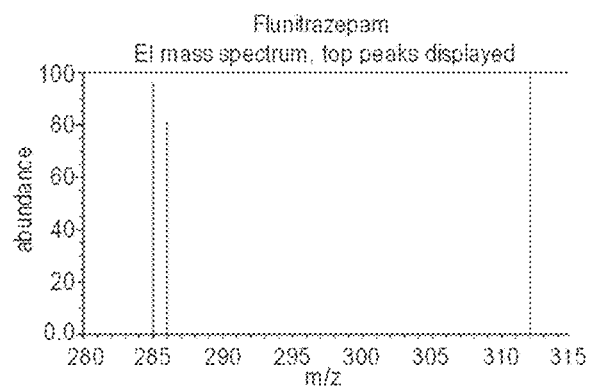
Figure 3E:
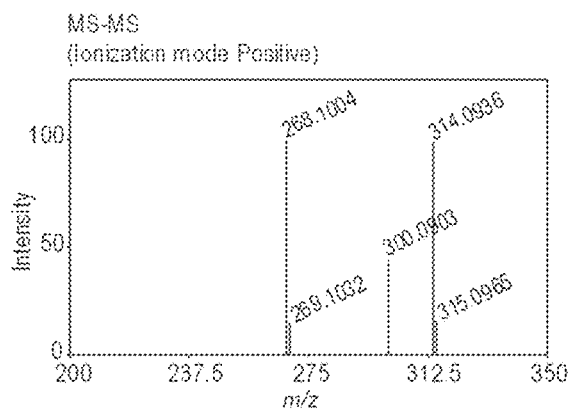
Figure 3E:
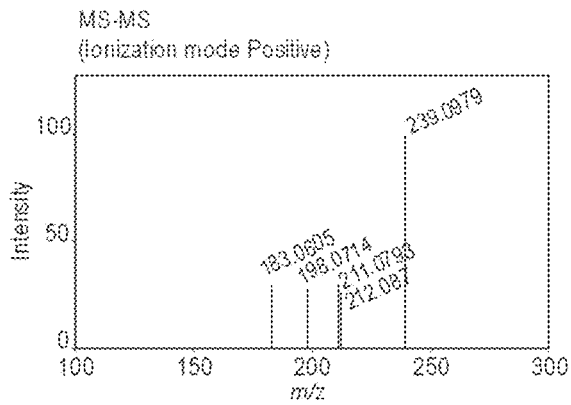
Figure 3E:
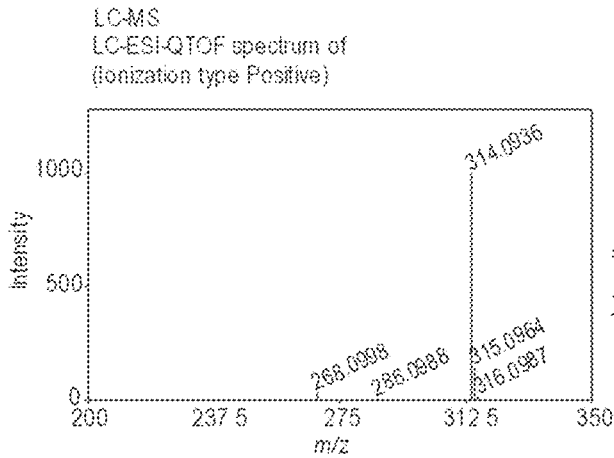
Figure 3E:
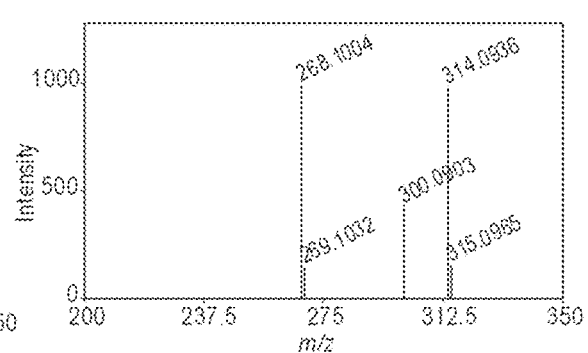
Figure 3F:
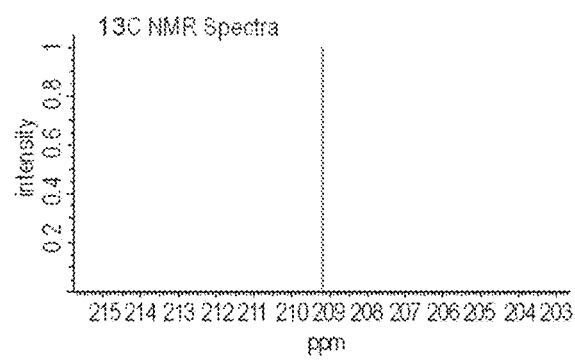
Figure 3F:
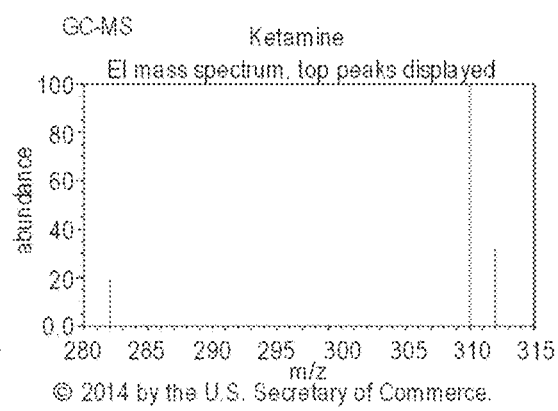
Figure 3F:
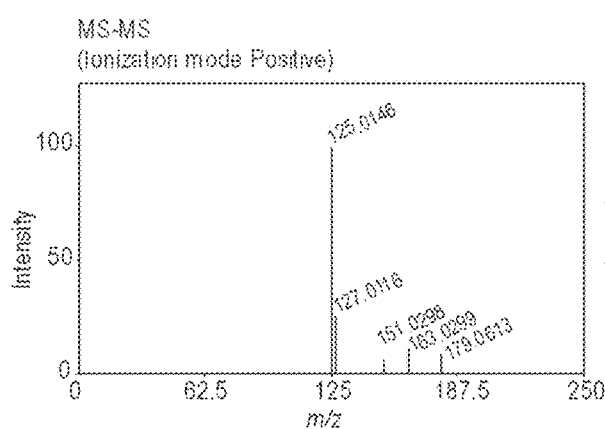
Figure 3F:
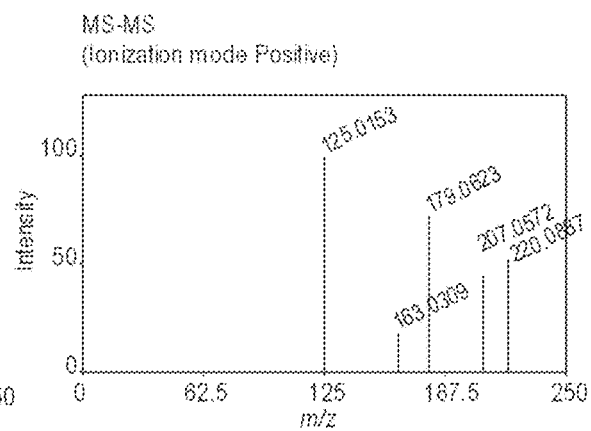
Figure 3F:
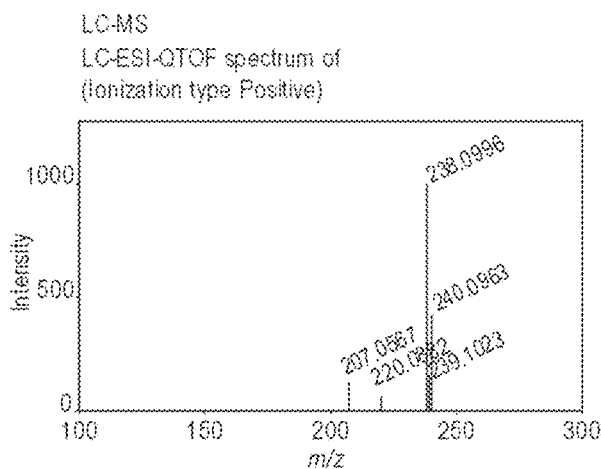
Figure 3F:
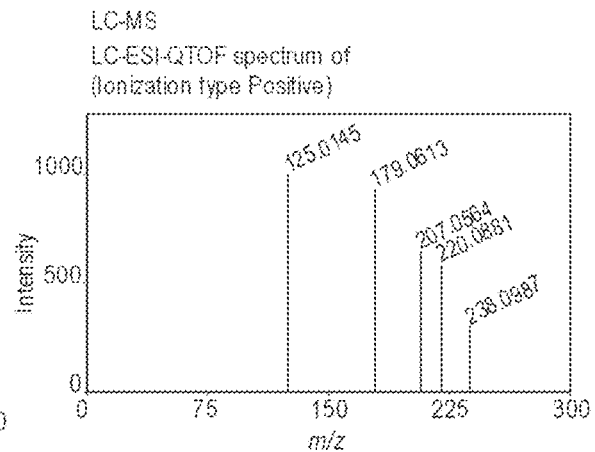
Figure 3G:
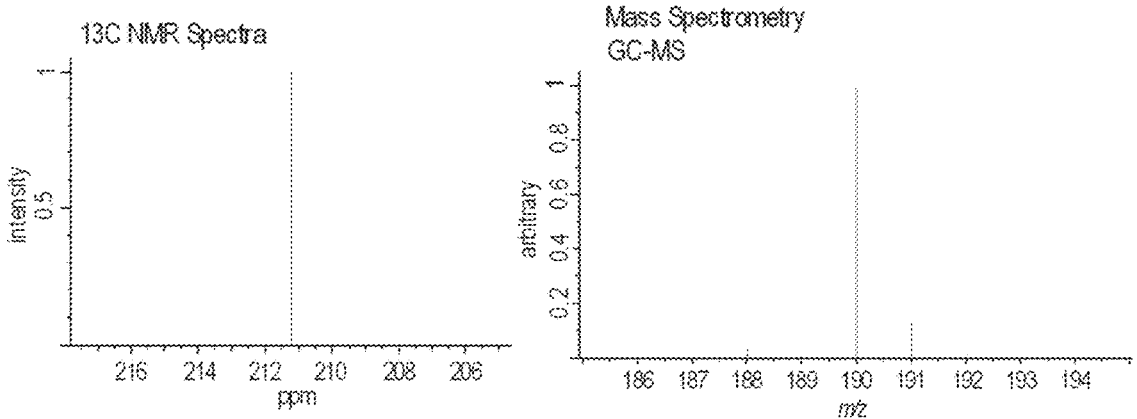
Figure 3G:
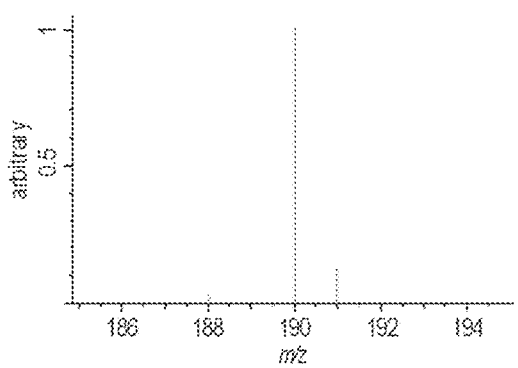
Figure 3G:
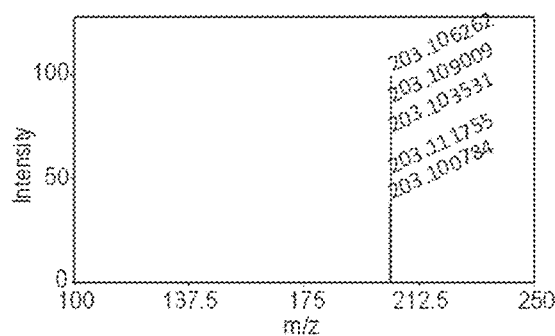
Figure 3G:
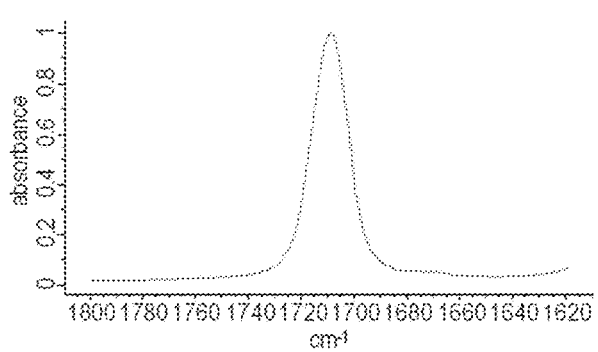
Figure 3H:
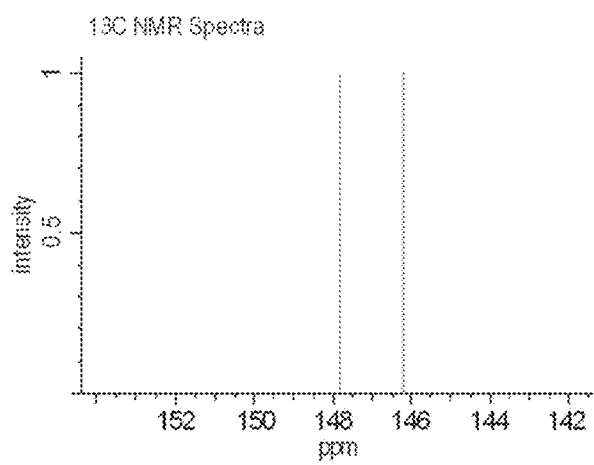
Figure 3H:
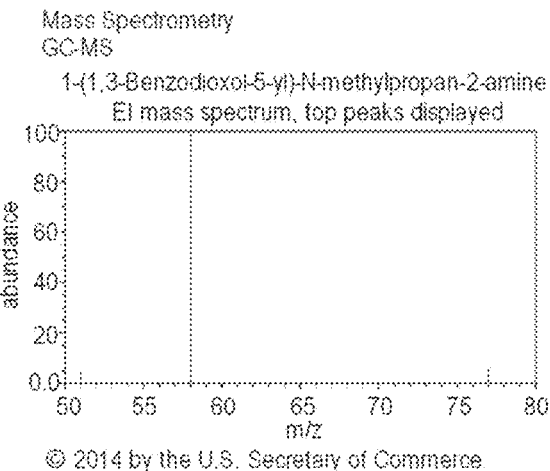
Figure 3H:
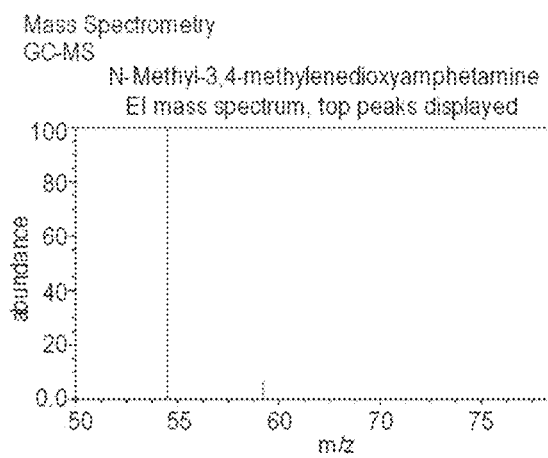
Figure 3H:
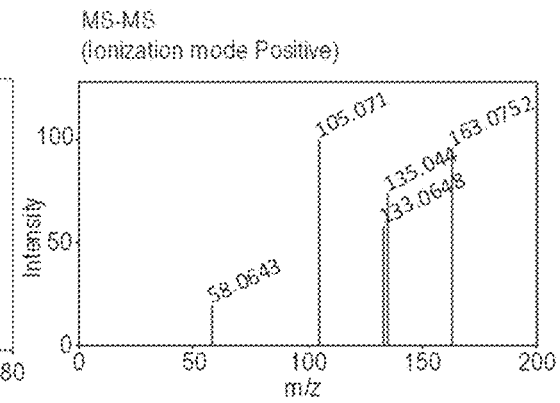
Figure 3H:
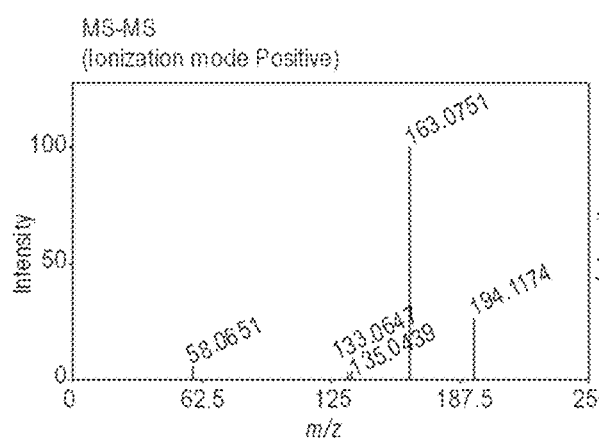
Figure 3H:
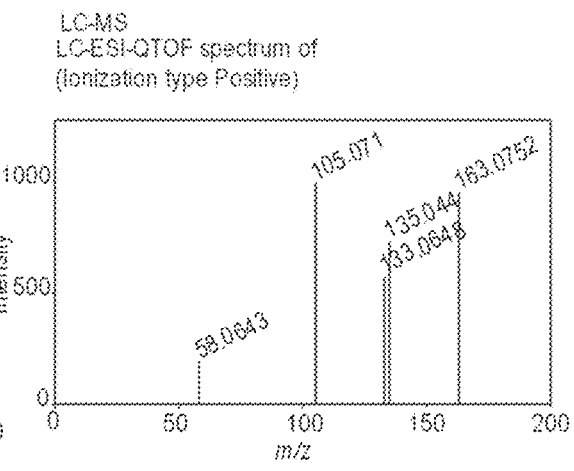
Figure 3I:
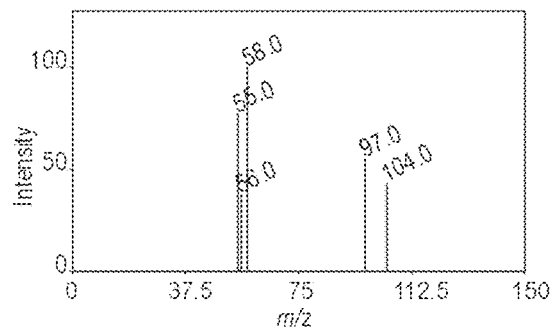
Figure 3I:
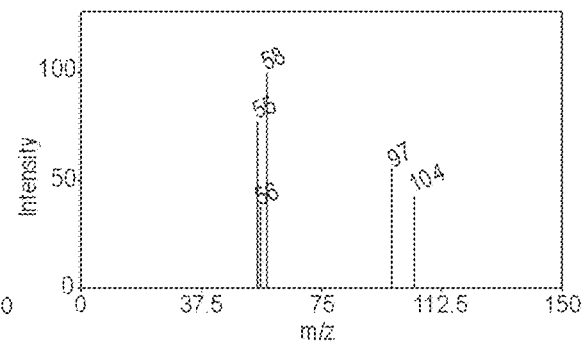
Figure 3I:
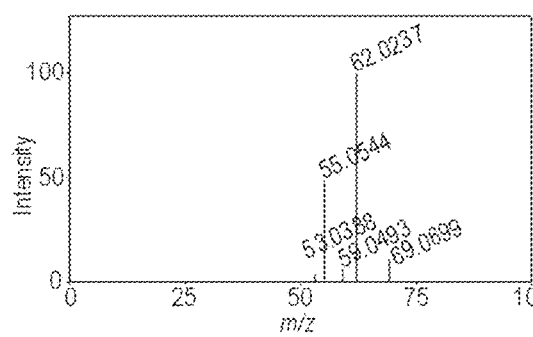
Figure 3I:
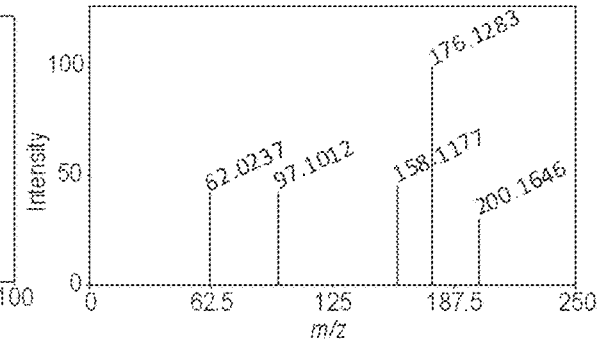
Figure 3I:
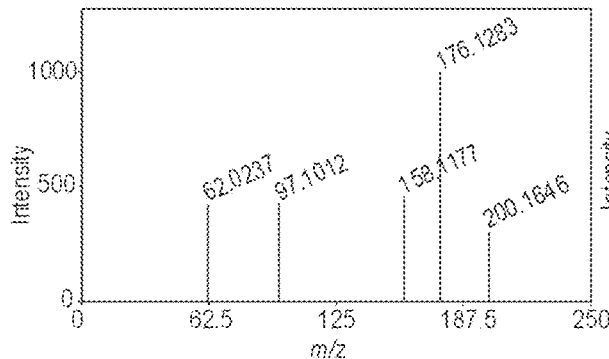
Figure 3I:
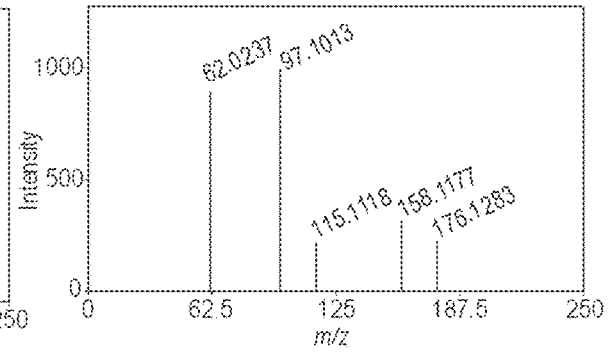
Figure 3J:
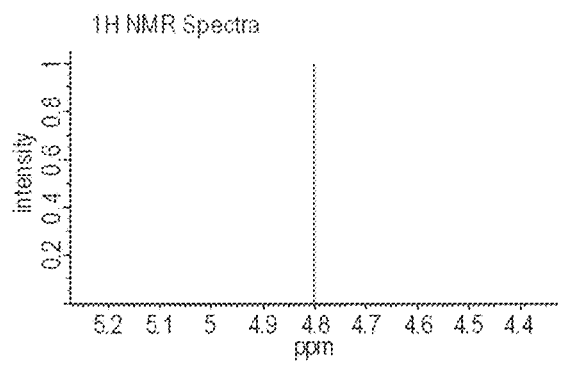
Figure 3J:
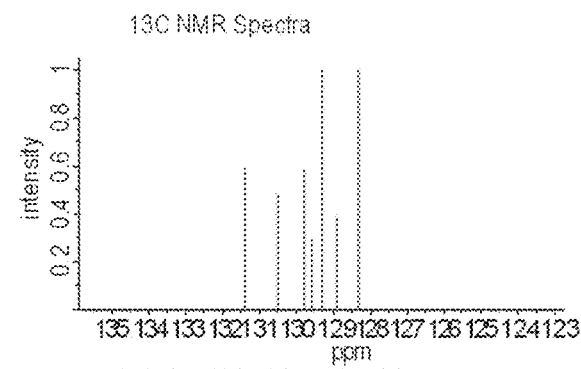
Figure 3J:
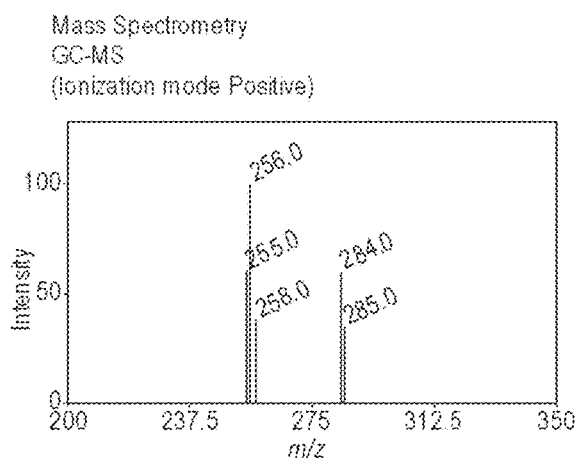
Figure 3J:
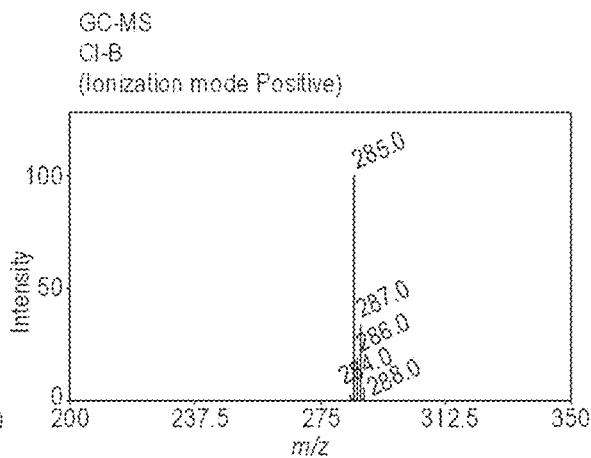
Figure 3J:
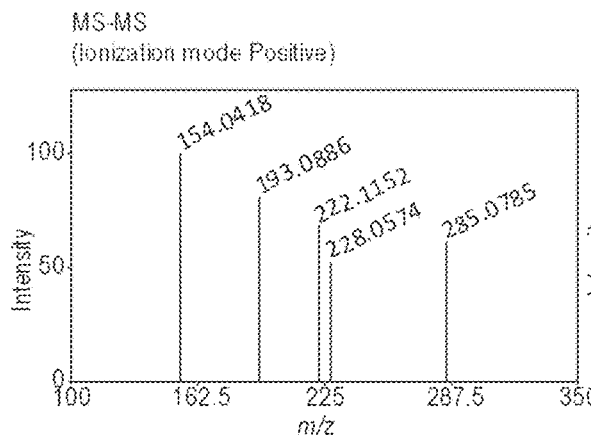
Figure 3J:
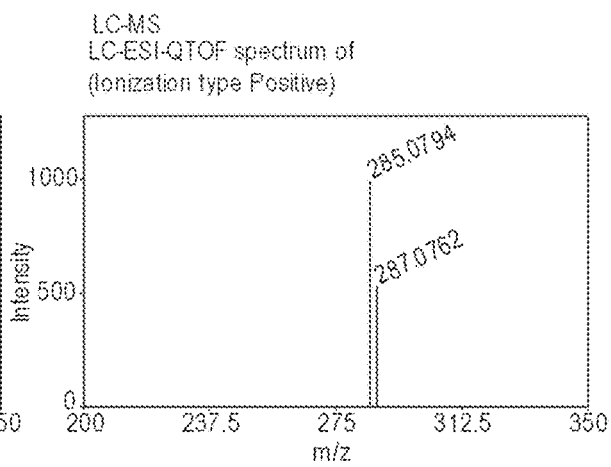

FIGS. 3A-J present spectral data of two major non-DRD solvents (water in FIG. 3A and ethanol in FIG. 3B) and spectral data pertaining to several DRDs (GHB in FIG. 3C, GBL in FIG. 3D, flunitrazepam (Rohypnol) in FIG. 3E, ketamine in FIG. 3F, methoxetamine (MXE) in FIG. 3G, MDMA in FIG. 3H, carisoprodol (Soma) in FIG. 3I, and diazepam in FIG. 3J), obtained from the publicly accessible source PubChem National Center for Biotechnology Information, U.S. National Library of Medicine [website: pubchem(dot)ncbi(dot)nlm(dot)nih(dot)gov].

The spectral data associated with non-DRD solutes and solvents can be applied within a designated spectral data processing software which aims to reduce noise levels and/or standardize the measured signal, facilitating the deduction of background noise and signals arising from non-DRD components within the sample. The spectral data provided in the figures were copied from PubChem, and it is possible that in this procedure of copying some mistakes were incorporated to the data presented or some data is missing. Hence, the relevant contents found in the figures and which pertains to the information for DRSs therein, as well as information pertaining to any other DRD, either identified in the specification or not, is hereby incorporated by reference.

For example, the spectral signature of flunitrazepam (Rohypnol) includes a characteristic absorption spectrum in the UV range, with a maximum absorption at 254 nm due to the presence of a carbonyl group in the molecule. Flunitrazepam also has a characteristic absorption spectrum in the IR range, with a number of peaks at around 1600 $cm^{-1}$, 1700 $cm^{-1}$, and 3000 $cm^{-1}$ due to the stretching and bending of bonds in the molecule.

In the context of some embodiments of the present invention, a spectral signature of a DRD includes the spectral information pertaining to a reagent that interacts selectively or more intensely with the DRD in the sample. In such embodiments, the sample containing member of the DRD detection system includes one or more reagents for generating a spectral signature indicative of a DRD upon exposure to light emitted from the light source.

Some spectroscopic assays suitable for detecting a DRD fall under the definition of colorimetric assays that use chemical reagents that undergo a measurable color change or displaced (and bleed) in the presence of the DRD. Colorimetric reagents are widely used in biochemistry to test for the presence of enzymes, specific compounds, antibodies, hormones and many more analytes. Colorimetric reagents are chemical compounds that change color when they react with or displaced by other substances. This property makes them useful for detecting and quantifying small organic compounds, such as DRDs. One type of colorimetric reagent that is commonly used for detecting DRDs is Mandelin reagent, which is a solution of 4-amino-3-hydroxybenzaldehyde in hydrochloric acid. When a DRD reacts with Mandelin reagent, it produces a blue color. The intensity of the blue color is proportional to the concentration of the DRD in the sample. Another type of colorimetric reagent that is commonly used for detecting DRDs is Folin-Ciocalteu reagent, which is a solution of phosphomolybdic acid and phosphotungstic acid in sulfuric acid. When a DRD reacts with Folin-Ciocalteu reagent, it produces a blue-purple color, and the intensity of the blue-purple color is proportional to the concentration of the DRD in the sample.

According to some embodiments of the present invention, the DRD detection system includes at least one reagent for generating a colorimetric effect upon contacting the DRD, and the colorimetric effect is detectable by the spectrophotometer in the DRD detection system. For example, DNPH (2,4-Dinitrophenylhydrazine) is a colorimetric reagent for the detection of microgram amounts of prednisone Additional non-limiting examples of colorimetric reagents that can be used to detect DRDs include ninhydrin (produces a purple color when it reacts with amino acids, Tollens' reagent (produces a silver mirror when it reacts with aldehydes), and Benedict's reagent (produces a red color when it reacts with reducing sugars). The choice of colorimetric reagent will depend on the specific DRD that is being detected.

Colorimetric assays for the identification of γ-hydroxybutyrate (GHB) typically involve the use of specific reagents that produce a visible color change or formation of a colored complex when reacted with the drug. Some commonly used reagents for colorimetric identification of GHB include:

Marquis Reagent, which is a mixture of formaldehyde and sulfuric acid that may produce a yellow to orange-brown color when reacted with GHB;

Froehde Reagent, which is a mixture of molybdic acid and sulfuric acid that may produce a green color when reacted with GHB;

Simon's Reagent, which is a combination of sodium nitroprusside, acetaldehyde, and hydrochloric acid that may produce a blue color when reacted with GHB;

Mandelin Reagent, which is a mixture of ammonium metavanadate and sulfuric acid that may produce a blue or green color when reacted with GHB; and Scott's Reagent, which is a combination of cobalt(II) thiocyanate and hydrochloric acid that may produce a blue color when reacted with GHB.

Infrared Spectrometry:

Infrared (IR) spectroscopy is another highly discriminatory method and is based on the measurement of the amount of IR radiation which is absorbed or emitted by a sample as a function of wavelength. A spectrum is obtained by passing infrared radiation through a sample and determining the amount of the incident radiation (radiation that actually hits the molecule rather than passing through) that is absorbed at each IR frequency. Interpretation of the spectra allows for determination of molecular functional groups. The IR spectrum of a pure molecular compound provides a distinctive fingerprint or signature which can be easily differentiated from the IR absorption pattern of other compounds, including compounds with the same chemical formula, but a different arrangement of atoms in the molecule (known as isomers). An advantage of IR techniques is that virtually, all compounds have IR active vibrational modes and can therefore be investigated both qualitatively and quantitatively. Recent advances in IR technology have allowed for the development of portable IR devices, such as the DRD detection system provided herein.

When reference spectra are available, most compounds can be unambiguously identified based on their IR spectra. In the context of the present invention, DRDs can be identified through a searchable database (such as webbook.nist(dot)gov). According to the Scientific Working Group for the Analysis of Seized Drugs (SWGDRUG), IR can produce structural information that will provide sufficient selectivity that generates the highest discriminating capability. IR can discriminate between diastereomers (such as pseudoephedrine and ephedrine) and free base/acid and salt forms. Free base/acid and salt forms refer to differences in physical properties that can alter the application of the substance. Free base is usually more volatile and normally has a lower boiling point, allowing the substance to be smoked. The salt form is usually more stable and tends to be crystalline and dissolvable in water, allowing for ingestion, insufflation (inhaling through the nose), or injection. A common example is crack cocaine (free base) and cocaine (salt); they are in fact the same drug (cocaine), and the actual effect on the body is the same, but due to different absorption and dosages based on method of use, it is possible to observe a spectrum of differing responses to each of the drugs. One of the notable benefits of IR spectroscopy is that it does not destroy the sample provided—an important consideration when working with drugs and the people who use them. As well, it requires only a very small sample size in the range of milligrams or less. Additionally, samples can be studied in virtually any physical state (primarily solid or liquid). Interference is very common and causes difficulty in identification.

Solid-Phase Assays:

Solid-phase matrices can be designed to specifically bind small amounts of a DRD in a liquid sample, and can be used to detect such presence when incorporated into chemical sensors. These matrices are often referred to as solid-phase extraction (SPE) or solid-phase microextraction (SPME) devices. They are widely used in analytical chemistry and biochemistry for the extraction and concentration of target compounds, including drugs, from complex liquid samples. Solid-phase sensors typically consist of a solid material (matrix) that acts as a stationary phase to selectively bind the target drug molecules from the liquid sample. In the context of some embodiments of the present invention, a solid-phase matrix can be functionalized with specific receptors, antibodies, or ligands that have a high affinity for a DRD of interest. As the liquid sample passes through or contacts the solid-phase matrix, the target DRD molecules selectively bind to the immobilized receptors. In some devices, according to some embodiments of the present invention, after specific or at least enhanced binding occurs, the solid-phase matrix is separated from the liquid sample, and the bound drug molecules can be eluted or released from the solid-phase for further analysis in another component of the sensor. Alternatively, the occupied receptor becomes a binding target of another molecular entity that accumulated only at locations where a DRD has bound to a receptor, thereby generating a detectable signal, such as a visual (color stain) signal, or an electrochemical signal.

A non-limiting example of a sensor for detecting a DRD based on solid-phase chemistry can be implemented as an electronic "nanonose" that includes a substrate and a plurality of nanostructures deposited onto said substrate, wherein at least a portion of the nanostructures includes nanostructures having attached thereto a functional moiety and at least another portion of the nanostructures includes nanostructures having attached thereto another functional moiety such that these functional moieties being different and being such that upon contacting a sample that contains a DRD, the nanostructures exhibit a detectable change in an electrical property that is indicative of the presence and/or amount of the DRD in the sample. The skilled artisan would appreciate the guidance and detailed description provided in documents, such as WO2011154939A1, for employing nanostructures in the design of solid-phase sensors specific for any given DRD.

A simple solid-phase assay can be implemented in the device provided herein, which is based on releasing a colored substance upon binding of a DRD to a receptor immobilized on a substrate, wherein the receptor releases a coloring agent into the sample containing the DRD upon contacting the solid-phase substrate. The present invention relates to DRD detection systems and methods for detecting the presence of a DRD in a beverage, wherein the DRD detection system for test the DRD includes a testing material based on a molecularly imprinted polymeric substrate with molecular receptors that complement a molecule associated with the DRD. The receptors are loaded with colored molecules which bind non-covalently to a binding site in the receptor with certain affinity, whereas the DRD has a similar or greater affinity thereto, and can therefore compete with the colored molecule on the binding site. When the molecule associated with the substance in the beverage replaces the colored molecule, the colored molecule bleeds out into the analyzed (assayed, tested) sample, changing its appearance and indicating the presence of the DRD. In some embodiments, the colored molecule can be a DRD-derivative having a coloring moiety attached thereto, while the DRD-derivative has been checked and found harmless and safe for consumption, unlike the free DRD compound. The molecularly imprinted polymeric substrate can be incorporated into various parts of the DRD detection system, such as a cellphone stylus, or various appendages of a cellphone protective covers.

According to some embodiments of the present invention a non-modified cellphone stylus according to the present invention can be used as a collector device for collecting a sample of a beverage for testing for the presence or absence of a DRD in the beverage by any of the DRD detection systems described herein. It will be appreciated that collecting a sample of a beverage can also be effected e.g., inter alia by a finger of the user, a straw or a beverage mixer, typical providable in a bar or pub venues.

Solid-phase assays are based of several types of chemistries, some of which are categorized as electrochemical, immuno-, and colorimetric assays, among other names.

Electrochemical Assays and Immunoassays:

Electrochemistry can be utilized to detect various DRDs by employing techniques such as voltammetry or electrochemical sensors. These methods rely on the analysis of the electrochemical behavior of the target compounds. Electrochemical assays offer several advantages for drug detection, including simplicity, sensitivity, specificity, and the potential for rapid analysis. DRDs can be detected using assays based on electrochemistry, using cellphone components as well as additional components that form the DRD detection system. In the case of detecting DRDs, an electrochemical sensor provides the solid phase component that includes one or more molecular appendages that specifically recognize and interact with the DRD of interest, producing characteristic electrochemical signals. The sensor's surface is usually functionalized with specific molecular receptors (e.g., antibodies or certain molecular recognition domains thereof) that selectively bind to the target drug molecules. When the DRD bind to the sensor's surface, it causes a change in the electron transfer characteristics, leading to distinctive electrochemical responses or signals.

For example, in the case of detecting drugs like GHB or flunitrazepam, electrochemical sensors can be designed to selectively detect and quantify these substances in beverages. The presence of the DRD in a sample of the beverage will lead to measurable changes in the current response, which give a qualitative signal, and/or may be correlated to the DRD's concentration.

Ion Mobility Spectrometry:

Ion mobility spectrometry (IMS) is a technique used to separate and identify ions based on their mobility in a gas. IMS has been used for a variety of applications, including the detection of explosives, identification of drugs, and analysis of food and beverages. In the context of drug and illicit substance identification, and some embodiments of the present invention, IMS can be used to separate and identify different types of drugs by their unique ion mobility. The principles behind IMS in the context of a detection system for detecting a DRD, can be implemented in a device that includes a cellphone and/or a cellphone protective cover.

IMS can be implemented in a handheld device, such as a cellphone. According to some embodiments of the present invention, a device for detecting a DRD, comprising a cellphone and/or any of its covers and a detection system for detecting the DRD based on IMS, can typically identify drugs and illicit substances in a matter of seconds. IMS is a non-destructive technique, which means that the sample can be analyzed without being destroyed.

An IMS detection assay is effected as follows: The sample is first ionized, typically by electron impact ionization. This process creates ions with a charge of +1 or +2. The ions are then introduced into a drift tube, which is filled with a neutral gas, such as helium or nitrogen. An electric field is applied to the drift tube, which causes the ions to move towards a detector. The ions travel through the drift tube at different speeds, depending on their size, shape, and charge. The ions are detected at the end of the drift tube, and their arrival time is used to determine their mobility. The mobility of an ion is affected by its size, shape, and charge. Drugs and other illicit substances have different sizes, shapes, and charges, which means that they will have different mobilities. This allows IMS to be used to separate and identify different types of drugs and illicit substances.

Miniaturized Detection System:

The DRD detection system that forms a part of the DRD detection device provided herein may include a miniaturized module of an analytical instrument, including, but not limited to, a module for measuring the interaction of at least one DRD with electromagnetic radiation (light), such as a miniaturized spectra meter for UV-Vis, infrared (IR; NIR), Raman, fluorescence, atomic absorption, X-ray (XRF, XRD), a module for measuring at least one physical property of at least one DRD, such as mass and charge chromatography (MS, GC-MS, LC-MS), ion chromatograph (IC), ion mobility (IMS), a module for measuring the affinity and specific interactions of at least one DRD, such as enzyme-linked immunosorbent assay (ELISA), surface plasmon resonance (SPR), quartz crystal microbalance (QCM), isothermal titration calorimetry (ITC), and affinity chromatography, a module for measuring the structure of at least one DRD, such as nuclear magnetic resonance (NMR), and circular dichroism (CD), a module for measuring conductivity of at least one DRD, such as a potentiostat/galvanostat for electrochemical analysis, a module for measuring mass and volume, such as high-performance liquid chromatography (HPLC), ion chromatography (IC) and liquid chromatography-mass spectrometry (LC-MS).

For any one of the above measuring instruments there may be a miniaturized implementation thereof that can be tethered to a cellphone to complete the DRD detection system and add DRD detection capabilities. For example, a company by the name VeriFood LTD, Israel, developed food product analyzers that communicate with a cellphone, which use technologies that may be suitable for a DRD detection system, as provided herein. Miniaturized measuring instruments that can be implemented in the DRD detection system include, without limitation, a microfluidic chip for capillary electrophoresis (CE). Such a module is used for separation and analysis of charged molecules based on their electrophoretic mobility. A detection system, according to such embodiments of the present invention, includes a microfluidic chip for capillary electrophoresis (CE) that is a miniaturized device that performs separation, detection, and analysis of charged molecules using microchannels and applied electric fields.

The field of "Lab on a Chip" encompasses all aspects of chip-based principles, techniques and devices for substance analysis, which are relevant in the context of a DRD detection system. The main tasks that can be carried out by a miniaturized module such as a lab-on-a chip include separation and analysis of drug molecules in a sample. An exemplary review article by Yongjian Ai et al. ["*Recent progress in lab-on-a-chip for pharmaceutical analysis and pharmacological/toxicological test*", *TrAC Trends in Analytical Chemistry*, 2019, 117, pp. 215-230], which is incorporated by reference herein, provides additional information pertaining to such miniaturized measuring instruments.

A DRD detection system may include one or more microfluidic diatomite analytical devices (µDADs), which consist of highly porous photonic crystal biosilica channels, as a lab-on-a-chip platform to detect illicit drugs. An exemplary review article by Xianming Kong et al. ["*Microfluidic diatomite analytical devices for illicit drug sensing with ppb-Level sensitivity Microfluidic diatomite analytical devices for illicit drug sensing with ppb-Level sensitivity*", *Sensors and Actuators B: Chemical*, 2018, 259, pp. 587-595], which is incorporated by reference herein, provides additional information pertaining to such miniaturized measuring instruments.

On-chip spectra meters, which are relevant in the context of a DRD detection system, have been reported in other publications that are available to any skilled artisan seeking to implement these tools in a device according to some embodiments of the present invention, such as the article by Li, A. and Fainman, Y. ["*On-chip spectrometers using stratified waveguide filters*", *Nat Commun*, 2021, 12, p. 2704; incorporated herein by reference], which present an ultra-compact single-shot spectrometer on silicon platform for sparse spectrum reconstruction. This miniaturized spectrophotometer consists of 32 stratified waveguide filters (SWFs) with diverse transmission spectra for sampling the unknown spectrum of the input signal and a specially designed ultra-compact structure for splitting the incident signal into those 32 filters with low power imbalance. Each SWF has a footprint less than 1 µm×30 µm, while the 1×32 splitter and 32 filters in total occupy an area of about 35 µm×260 µm, which is the smallest footprint spectrometer realized on silicon photonic platform. Experimental characteristics of the fabricated spectrometer demonstrate a broad operating bandwidth of 180 nm centered at 1550 nm and narrowband peaks with 0.45 nm Full-Width-Half-Maximum (FWHM) can be clearly resolved. This concept can also be implemented using other material platforms for operation in optical spectral bands of interest for various DRD detection spectra-based assays.

Greaves, E. D., and Manz ["*Toward on-chip X-ray analysis*", *Lab on a Chip*, 2005, 5(4), pp. 382-391; incorporated herein by reference] explored the possibility of performing chemical analysis and structure determinations with the use of X-rays in a microfluidic chip environment. Externally generated radiation, radioisotope irradiation and on-chip generated X-rays were considered as excitation means for the performance of sample analysis with the techniques of X-ray fluorescence and diffraction. The absorption properties of chip-building materials by different radiation sources are reviewed and data on absorption coefficients calculated, upon which recommendations for optimizations with the use of various X-ray sources may be made. The capabilities and limitations of on-chip X-ray analysis are placed in perspective by preliminary experimental results of diffraction, fluorescence and on-chip X-ray generation experiments.

A DRD detection system may include a miniaturized low-field nuclear magnetic resonance (NMR) module, which can be used to detect at least one DRD in a beverage sample. An exemplary review article by Jens Anders et al. ["*Progress in miniaturization and low field nuclear magnetic resonance*", *Journal of Magnetic Resonance*, 2021, 322, 106860], which is incorporated by reference herein, provides additional information pertaining to such miniaturized measuring instruments.

A DRD detection system may include a miniaturized mass spectrometer (MMS), which is a type of mass spectrometer (MS) that has small size and weight and can be attached to a cellphone, according to some embodiments of the present invention. MMS is designed to maintain sufficient resolutions, detection limits, accuracy, and especially the capability of automatic operation that are necessary for DRD detection. An exemplary review article by Zhengyi Ren et al. ["*A review of the development and application of space miniature mass spectrometers*", *Vacuum*, 2018, 155, pp. 108-117], and Mielczarek P, et al. ["*Miniaturization in Mass Spectrometry*", *Mass Spectrom Rev*, 2020, 39(5-6), pp. 453-470], which are incorporated by reference herein, provide additional information pertaining the development and application of several types of space miniature mass spectrometers including magnetic sector mass spectrometer, quadrupole mass spectrometer, ion trap mass spectrometer and time-of-flight mass spectrometer.

Without limiting the scope of the present invention, exemplary miniaturized spectrometers that can be implemented and/or configured for use in the device provided herein, for example on a chip, include the miniaturized spectrometers offered by Ocean Insight, Florida, USA [www(dot)oceaninsight(dot)com]. Among the many miniaturized spectrometers that are available from Ocean Insight, the following are representative products that can be useful in some embodiments of the present invention:

Ocean FX spectrometer: The Ocean FX spectrometer is a handheld spectrometer that is ideal for environmental monitoring, food analysis, and medical diagnostics. It has a spectral range of 200-1100 nm and a resolution of 1.2 nm. It can acquire spectra at a rate of up to 4500 scans per second.

Ocean ST spectrometer: The Ocean ST spectrometer is a compact spectrometer that is ideal for industrial process control and scientific research. It has a spectral range of 200-1100 nm and a resolution of 2.0 nm. It can acquire spectra at a rate of up to 1000 scans per second.

Ocean HR2 spectrometer: The Ocean HR2 spectrometer is a high-resolution spectrometer that is ideal for applications that require precise measurements of the UV-Vis spectrum. It has a spectral range of 200-1100 nm and a resolution of 0.5 nm. It can acquire spectra at a rate of up to 100 scans per second.

Ocean Mini USB spectrometer: The Ocean Mini USB spectrometer is a miniature spectrometer that is ideal for educational and research applications. It has a spectral range of 350-1000 nm and a resolution of 2.0 nm. It can acquire spectra at a rate of up to 100 scans per second.

Ocean MicroNIR spectrometer: The Ocean MicroNIR spectrometer is a miniature NIR spectrometer that is ideal for food analysis and agricultural research. It has a spectral range of 900-1700 nm and a resolution of 2.0 nm. It can acquire spectra at a rate of up to 100 scans per second.

MYBOUNCER LTD: A spectrophotometer identifying presence of a substance of interest using laser-based spectroscopy device transiently linked to a cellphone.

Raman spectroscopy is a technique of probing matter that requires little to no sample preparation. In a Raman spectrometer, a monochromatic light (near UV, visible, or near IR) illuminates a sample or analyte. Miniaturized Raman spectrometers that can be implemented and/or reconfigured for use in the device provided herein, for example on a chip, include the miniaturized Raman spectrometers offered by Hamamatsu Photonics, Hamamatsu, Japan [www(dot)Hamamatsu(dot)com]. Among several miniaturized spectrometers that are available from Hamamatsu Photonics, the following are representative products that can be useful in some embodiments of the present invention:

Mini-spectrometer TF series: The TF series is a polychromator provided in a compact, thin case that houses optical elements, image sensor, and driver circuit. It is a portable Raman spectrometer with a spectral range of 200-1700 nm and a resolution of 2.0 nm. It can acquire spectra at a rate of up to 100 scans per second.

Mini-spectrometer TR series: The TR series is a Raman spectrometer with a spectral range of 200-2500 nm and a resolution of 2.0 nm. It is a portable Raman spectrometer that can be used for a variety of applications, including food analysis, medical diagnostics, and materials science.

Mini-spectrometer TA series: The TA series is a Raman spectrometer with a spectral range of 350-2500 nm and a resolution of 2.0 nm. It is a portable Raman spectrometer that is ideal for handheld or remote sensing applications.

Mini-spectrometer TS series: The TS series is a Raman spectrometer with a spectral range of 785-1700 nm and a resolution of 2.0 nm. It is a portable Raman spectrometer that is ideal for food analysis and agricultural research.

Mini-spectrometer TT series: The TT series is a Raman spectrometer with a spectral range of 785-1700 nm and a resolution of 0.5 nm. It is a portable Raman spectrometer that is ideal for applications that require high resolution, such as medical diagnostics and materials science.

Sifeng Mao et al. ["*Cell analysis on chip-mass spectrometry*", *TrAC Trends in Analytical Chemistry*, 2018, 107, pp. 43-59; incorporated herein by reference] describe microfluidic chip and mass spectrometry, chip-mass spectrometry (Chip-MS) implemented in a microfluidic chip that may be used in a DRD detection system, according to some embodiments of the present invention.

Xiangwei He et al. ["*Recent advances in microchip-mass spectrometry for biological analysis*", *TrAC Trends in Analytical Chemistry*, 2014, 53, pp. 84-97; incorporated herein by reference] describe microchip-mass spectrometry (chip-MS) devices and methods that may be used in a DRD detection system, according to some embodiments of the present invention.

Akbar, M. et al. ["*Chip-scale gas chromatography: From injection through detection*", *Microsyst Nanoeng*, 2015, 1, 15039; incorporated herein by reference] describe miniaturized gas chromatography (µGC) systems that may be used in a DRD detection system, according to some embodiments of the present invention.

Tsunoda M. ["*On-Chip Liquid Chromatography*", *Encyclopedia*. 2022; 2(1), pp. 617-624; incorporated herein by reference] describes an on-chip liquid chromatography (LC) technology that is miniaturized to fit on a microchip that may be used in a DRD detection system, according to some embodiments of the present invention.

John P Murrihy et al. ["*Ion chromatography on-chip*", *Journal of Chromatography A*, 2001, 924(1-2), pp. 233-238; incorporated herein by reference] describe a miniaturized ion-exchange chromatography system that may be used in a DRD detection system, according to some embodiments of the present invention.

Sebastian K. Piendl et al. ["2D in Seconds: Coupling of Chip-HPLC with Ion Mobility Spectrometry", Analytical Chemistry, 2019, 91(12), pp. 7613-7620; incorporated herein by reference] describe a chip-based high-performance liquid chromatography (chip-HPLC) with ion mobility spectrometry (IMS) via fully integrated electrospray emitters that may be used in a DRD detection system, according to some embodiments of the present invention.

Mei Chen et al. ["*A Dual-angle fiber dynamic light scattering system integrated with microfluidic chip for particle size measurement*", *Optics & Laser Technology*, 2022, 150, 107891; incorporated herein by reference] describe an integrated dual-angle DLS device which incorporates microfluidic chip and fiber optic probes that may be used in a DRD detection system, according to some embodiments of the present invention.

Il-Hoon Cho et al. ["*Chemiluminometric enzyme-linked immunosorbent assays (ELISA)-on-a-chip biosensor based on cross-flow chromatography*", *Analytica Chimica Acta*, 2009, 632(2), pp. 247-255; incorporated herein by reference] describe a chemiluminometric biosensor system for point-of-care testing using an immuno-chromatographic assay combined with an enzyme (e.g., horseradish peroxidase) tracer that produces a light signal measurable on a simple detector that may be used in a DRD detection system, according to some embodiments of the present invention.

Pakorn Preechaburana et al. ["*Surface Plasmon Resonance Chemical Sensing on Cell Phones*", *Angew Chem Int Ed Engl*, 2012, 51(46), pp. 11585-8; incorporated herein by reference] describe a miniaturized Surface Plasmon Resonance (SPR) device that may be used in a DRD detection system, according to some embodiments of the present invention.

Takashi Abe and Masayoshi Esashi ["*One-chip multichannel quartz crystal microbalance (QCM) fabricated by Deep RIE*", Sensors and Actuators A: Physical, 2000, 82(1-3), pp. 139-143; incorporated herein by reference] describe a one-chip multichannel quartz crystal microbalance (QCM) sensor that may be used in a DRD detection system, according to some embodiments of the present invention.

Jia Y et al. ["*Isothermal titration calorimetry in a 3D-printed microdevice*", Biomed Microdevices, 2019. 21(4), p. 96; incorporated herein by reference] describe a microdevice that combines 3D-printed microfluidic structures with a polymer-based MEMS thermoelectric sensor that may be used in a DRD detection system, according to some embodiments of the present invention.

Woo-Jae Chung et al. ["*Microaffinity purification of proteins based on photolytic elution: Toward an efficient microbead affinity chromatography on a chip*", Electrophoresis, 2005, 26(3), pp. 694-702; incorporated herein by reference] describe a bead affinity chromatography system based on the photolytic elution method and integrated into a glass-silicon microchip that may be used in a DRD detection system, according to some embodiments of the present invention.

Max Piffoux et al. ["*Potential of on-chip analysis and engineering techniques for extracellular vesicle bioproduction for therapeutics*", View, 2022, 3(1), 20200175; incorporated herein by reference] describe microfluidic technologies that may be used in a DRD detection system, according to some embodiments of the present invention.

Raluca M. Fratila and Aldrik H. Velders ["*Small-Volume Nuclear Magnetic Resonance Spectroscopy*", Annual Review of Analytical Chemistry, 4, pp. 227-249; incorporated herein by reference] describe miniaturized coils for NMR spectroscopy that may be used in a DRD detection system, according to some embodiments of the present invention.

Amr Shaltout, et al. ["*Photonic spin Hall effect in gap-plasmon metasurfaces for on-chip chiroptical spectroscopy*", Optica, 2015, 2(10), pp. 860-863; incorporated herein by reference] describe compact and power-efficient metasurface-based chiroptical spectroscopy solutions based on gap-plasmon metasurfaces (GPMSs) that may be used in a DRD detection system, according to some embodiments of the present invention.

Muñoz-Martínez, A. I. et al. ["*Electrochemical Instrumentation of an Embedded Potentiostat System (EPS) for a Programmable-System-On-a-Chip*". Sensors, 2018, 18, 4490; incorporated herein by reference] describe the development of a programmable Embedded Potentiostat System (EPS) capable of performing electrochemical sensing over system-on-a-chip platforms that may be used in a DRD detection system, according to some embodiments of the present invention.

Akbar, M. et al. ["*Chip-scale gas chromatography: From injection through detection*", Microsystems & Nanoengineering, 2015, 1, p. 15039; incorporated herein by reference] describe a miniaturized gas chromatography (µGC) systems that may be used in a DRD detection system, according to some embodiments of the present invention.

Gustavo Coelho Rezende et al. ["*Micro photoionization detectors*", Sensors and Actuators B: Chemical, 2019, 287, pp. 86-94; incorporated herein by reference] describe recent developments in photoionization detector miniaturization, where most of the devices are compatible with microfluidic arrangements that may be used in a DRD detection system, according to some embodiments of the present invention.

Li, X. et al. ["*Chip-based ion chromatography (chip-IC) with a sensitive five-electrode conductivity detector for the simultaneous detection of multiple ions in drinking water*", Microsystems & Nanoengineering, 2020, 6, Article number 66; incorporated herein by reference] describe a chip-based ion chromatography (chip-IC) system that may be used in a DRD detection system, according to some embodiments of the present invention.

A DRD Detection Case:

In various components of the device, such as the cellphone, and/or the cellphone protective cover and/or any cellphone add-on, the DRD detection system may be physically associated therewith integrally and/or by connection. When components are associated integrally, it means that they are designed, manufactured and/or assembled as an inseparable part of the same unit. These components are interconnected and function together as a single entity. They cannot be easily separated or replaced without significantly altering the overall structure or functionality of the component or the device. In other words, they are physically integrated into the device and cannot be used independently. When components are connected, it means that they are designed as separate components or units that can be easily interchanged or replaced without affecting the overall manufacturing process and functionality of the device. Each module performs a specific function and can be used independently or combined with other components to create a complete device, or be replaced with other components of different properties. This modular approach allows for flexibility in manufacturing and use, scalability, and more effective marketing, as components can be upgraded or replaced individually without the need to replace the entire device.

Since the cellphones market offers mobile devices in a wide range of form-factors, the DRD detection system of the DRD detection device provided herein can be manufactured as a generic one-size DRD detection system, designed to be integrated modularly within any model-specific cellphone cover, thereby simplifying the manufacturing of cellphone protective covers for a DRD detection device that fits any given cellphone. The DRD detection system can be integrated modularly in a cellphone protective cover, whereas the DRD detection system exhibits a form-factor that fits into a cellphone protective cover, and the cellphone protective cover is designed with a specific cellphone cavity that houses a specific cellphone model; i.e., in cellphone protective cover for small cellphone models the DRD detection system will take up less space within the cellphone protective cover compared to cellphone protective cover for larger cellphone models. A cellphone protective cover that houses (integrally or modularly) a DRD detection system, as described herein, is referred to herein as a DRD detection case.

According to some embodiments, provided herein is a DRD detection case that encases a cellphone and constitutes a device for detecting at least one DRD. In such embodiments, the device includes at least a cellphone and a cellphone protective cover, wherein the DRD detection system, or at least some major components thereof, such as a spectra meter, are integrated in the cellphone protective cover. In such embodiments, the cellphone protective cover that houses a DRD detection system (integrally or modularly) may define a cellphone housing cavity that conforms, at least partially, to the outer shape of the cellphone, and further define one or more access openings to permit access to integrated interfaces of the cellphone (e.g., charging port, power button, camera lens, audio jack, etc.), or exhibit replacement components (i.e., interfaces) for those obscured or blocked thereby, such that day-to-day use and/or operation of any function of the cellphone and/or the cellphone protective cover is substantially not affected by the DRD detection system.

In the context of the present invention, a DRD detection case exhibits all the replacement components discussed hereinabove, as well as a form-factor of a cellphone as defined hereinabove.

In some embodiments, the DRD detection system, or at least some major components thereof, may be housed within the thickness of cellphone protective cover and be physically associated therewith integrally and/or modularly. For example, a spectra meter may be housed within the thickness of a back plane of the cellphone protective cover. The cellphone protective cover may secure the cellphone within the cavity while at least one surface of the cellphone remains exposed (e.g., the screen). The cellphone protective cover may also include an internal interface and/or external interface. The internal interface may engage a corresponding interface on the cellphone to provide power from the one or more rechargeable power sources to the cellphone. The external interface may be electrically coupled to the internal interface in order to transmit signals from the cellphone to an external device (e.g., USB port). The external interface may further serve to recharge the one or more rechargeable power sources in the cellphone and/or in the cellphone protective cover. The cellphone protective cover may further comprise a recharging device integrated within the cellphone protective cover that wirelessly recharges the one or more rechargeable power cells in the cellphone and/or in the cellphone protective cover. This may include an inductive electrical recharging system that requires no direct contact or can recharge at a distance.

According to some embodiments, the cellphone protective cover may also include additional communication interfaces and/or processors which form parts of the DRD detection system. For instance, a plurality of communication interfaces may be coupled to the internal interface, wherein the cellphone can transmit and receive signals via the communication interfaces in the cellphone protective cover. Likewise, at least one processor within the cellphone protective cover may be coupled to the internal interface and adapted to pass information via one or more interfaces of the cellphone protective cover and provide the collected information to the cellphone. In one example, the at least one processor may be adapted to execute one or more instructions under the control of the cellphone, wherein the instructions may include one or more execution commands pertaining to a DRD detection assay.

The cellphone protective cover may also include a dedicated sample loading interface integrated into the cellphone protective cover, e.g., in the form of an opening, a slit, or a hole, allowing the user to contact an element of the DRD detection system with a sample to be tested.

The cellphone protective cover may also include a display interface integrated into the cellphone protective cover to display information to a user, such as DRD detection assay results. Such display interface may allow expanding the display from the cellphone to the display interface.

According to some embodiments, the thickness of the cellphone protective cover may be approximately or substantially the same as the thickness of the cellphone. For this purpose, the cellphone protective cover may be slim and/or have an ergonomic shape so that it does not significantly increase the thickness and/or size of the cellphone. Consequently, cellphone can be used within the cellphone protective cover for extended periods of time since the cellphone protective cover does not significantly increase the bulkiness of the cellphone, and does not interfere substantially with day-to-day use and/or operation of any function of the cellphone.

According to some embodiments, a cellphone protective cover for the device provided herein, comprises: a back plane, a first and second sides, a bottom side, and a DRD detection system housed within the thickness of the back plane. The back plane and first, second and bottom sides may define a cellphone housing cavity for mounting the cellphone. The DRD detection system may be used while a cellphone is mounted within the cavity. The cellphone protective cover may also include an internal interface that electrically couples the one or more battery cells to the cellphone.

Figure 5:
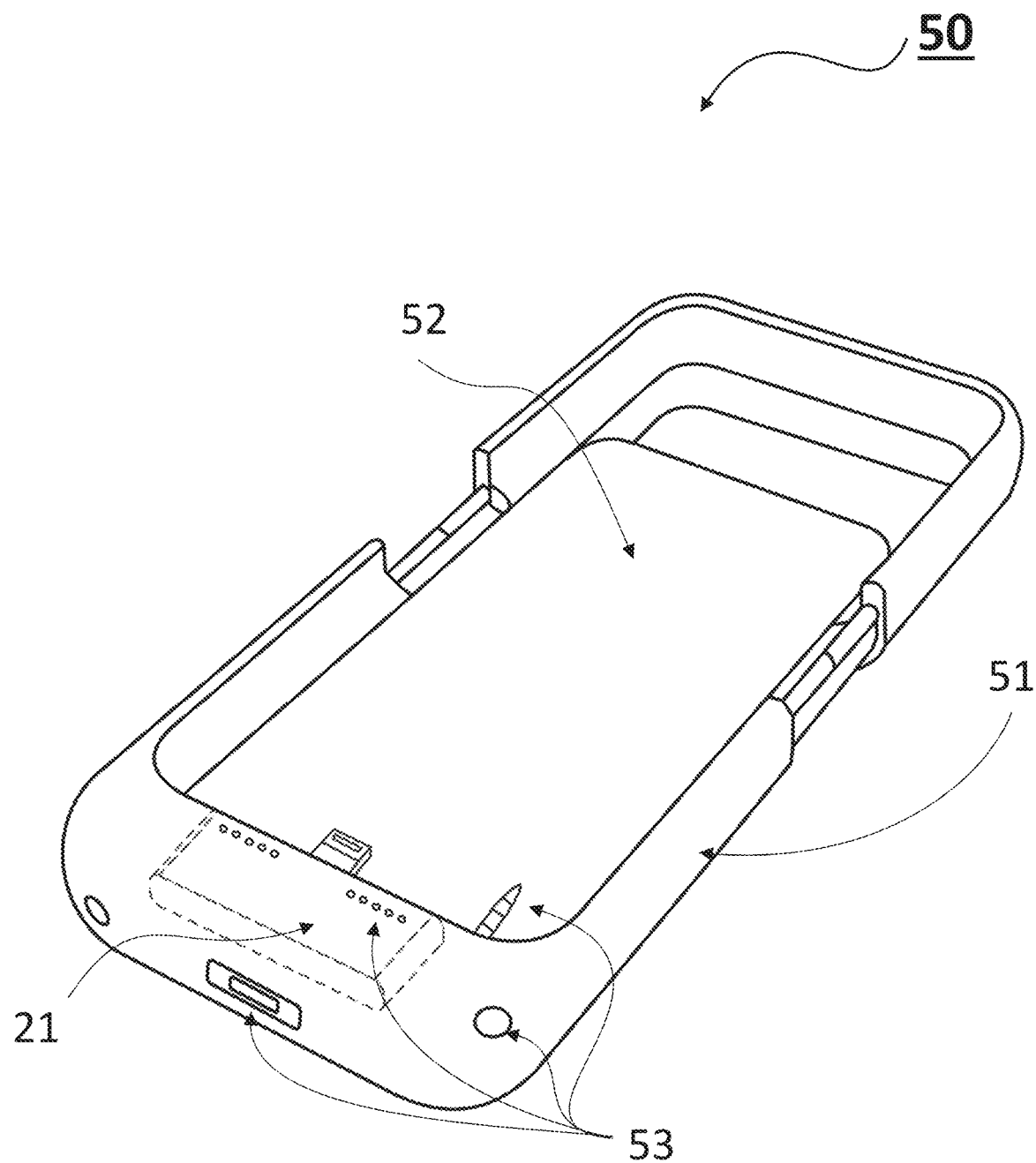
FIG. 5 presents DRD detection device 50 (cellphone not shown), according to some embodiments of the present invention, exhibiting cellphone protective cover in the form of case 51 comprising DRD detection system 21 housed within the thickness of case 51 that exhibits cellphone housing cavity 52 for mounting a cellphone and replacement ports 53.

FIG. 5 presents DRD detection device 50, according to some embodiments of the present invention, exhibiting cellphone protective cover in the form of case 51 comprising DRD detection system 21 housed within the thickness of case 51 that exhibits cellphone housing cavity 52 for mounting a cellphone and replacement ports 53, which may include, without limitation, speaker-vents, USB port, charging port, audio port, microphone hole, etc., as well as other ports for accessing the DRD detection system with a sample, and other functionalities thereof. As can be seen in FIG. 5, case 51 is designed with many mechanical features of a battery case, as these battery cases are known in the market.

According to some embodiments, provided herein is a device for detecting at least one DRD that includes at least a cellphone and a cellphone protective cover, wherein the DRD detection system, or at least some major components thereof, such as a spectra meter, are integrated in a cellphone protective cover that may define a cavity or a plane that partially conforms to or partially covers the outer shape of the cellphone, or in other words, covers partially at least one plane or at least one side of the cellphone. In some such embodiments the cellphone protective cover may cover completely or partially a back plane or a bottom side of the cellphone, without substantially interfering with day-to-day use and/or operation of any function of the cellphone.

As can be seen in FIG. 2 and FIG. 5, in some embodiments wherein unified DRD detection system 21 is integrated in a cellphone protective cover, the cellphone protective cover is configured to house DRD detection system 21 with excess space, allowing the cellphone protective cover component of the DRD detection device to be designed so as to fit almost any cellphone model.

A Sticker:

In some embodiments of the present invention, the DRD detection system includes one or more adhesive members (stickers) that can be affixed to any surface on the cellphone or any of its protective covers, stylus or add-ons via an adhesive layer. Hence, also provided herein is a device as defined herein, comprising a DRD detection system that is implemented and/or includes a sticker.

Thus, according to an aspect of some embodiments of the present invention, there is provided a sticker for detecting at least one DRD, which includes:

(a) a solid matrix having a front side and a back side;
  (b) a chemically active component which comprises at least one chemical reagent designed for generating a detectable effect when contacting at least one DRD applied on or in the matrix, chemically active component being suitable for at least one DRD detection from the front side; and (c) an adhesive layer on the back side that is adherable to a cellphone and/or a cellphone protective cover and/or a cellphone screen, front or back protective cover and/or a cellphone stylus and/or other cellphone add-on and/or any combination thereof.

In order to facilitate the use of the sticker, according to some embodiments of the present invention, the sticker further includes:

(d) a front liner applied onto the front side of the sticker in order to protect any chemically active component thereon when the sticker is stored and/or not in use; and (e) a back protective liner applied onto the adhesive layer to protect it when the sticker is stored.

The adhesive layer on the back side of the sticker provides the means to adhere the sticker to any component of the cellphone or any of it covers, namely in the context of the DRD detection system, the adhesive layer is adhered to the cellphone and/or the cellphone protective cover and/or the cellphone screen, front or back protective cover and/or cellphone stylus and/or other cellphone add-on and/or any combination thereof.

Figure 6:
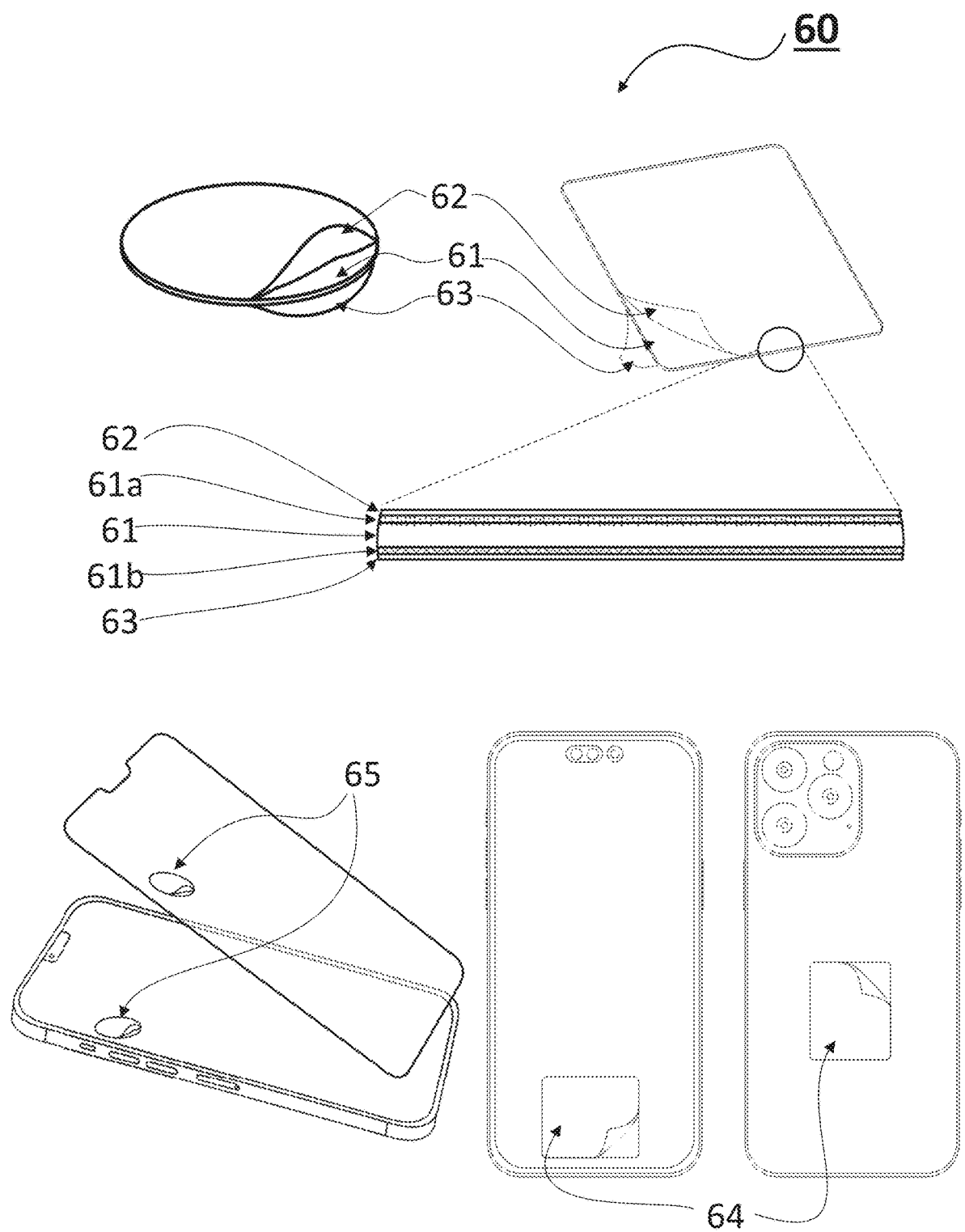
FIG. 6 shows exemplary sticker 60, exhibiting solid matrix 61 comprising chemically active components (not shown), front side 61a, back side 61b, front liner 62 protecting front side 61a, back liner 63 protecting back side 61b until applying the sticker, sticker 64 applied on a cellphone front or back protective cover, and sticker 65 applied on a cellphone screen protective cover.

FIG. 6 shows exemplary sticker 60, exhibiting solid matrix 61 comprising chemically active components (not shown), front side 61a, back side 61b, front liner 62 protecting front side 61a, back liner 63 protecting back side 61b until applying the sticker, sticker 64 applied on a cellphone front or back protective cover, and sticker 65 applied on a cellphone screen protective cover.

The sticker is designed to detect one or more DRDs based on chemically active components (chemical reagents) applied, immobilized or otherwise present on or in the solid matrix of the sticker. As shown in FIG. 6, the sticker may be provided with a protective liner on its back side, also known as backing or release film, which is removed prior to affixing the sticker to the cellphone or any of its protective covers, add-ons and/or stylus—the sticker is regarded physically associated once it has been affixed to any surface on the cellphone or any of its protective covers, add-ons and/or stylus. The sticker may be provided with an additional protective liner that covers its front side, protecting the chemical reagents while not in use, and removed either post installation and/or prior to use. The additional protective liner can be reusable, i.e., removed before the DRD detection system is used for detecting the presence or absence of a DRD in a beverage and applied back thereafter. The additional liner can serve also as a light filter for selecting specific wavelength(s) when needed, or a background object exhibiting a specific background color (e.g., white and/or reflective), such as often needed in certain spectroscopic assays.

The body of the sticker, referred to herein as a solid matrix, is flat and thin with respect to the area of the sticker, and typically made of a porous or absorbent substance. The substance may be a cellulosic material, a natural polymer, a synthetic polymer, or a combination thereof. The solid matrix is designed to contain at least one chemically active component and effect various DRD detection assays, and therefore may include free or immobilized chemical reagents, free and/or immobilized DRD receptors, solvents and other factors that are required to perform the DRD detection assay.

The area of the sticker, and practically the front side of the solid matrix, on which the DRD detection assay is carried out, is referred to as the active area; it is typically the active area that exhibits chemically active components and includes at least one chemical reagent designed for generating a detectable effect when contacting at least one DRD.

The active area can cover the entire front side of the sticker, a region thereof, several isolated regions thereof and/or several adjacent regions thereof. The regions correspond to DRD detection assays, wherein in some embodiments, wherein each region in the active area corresponds to a detection assay pertaining to one specific DRD, or alternatively, each region in the active area corresponds to a detection assay pertaining to a group of DRDs. In some embodiments, all or some of the regions are identical, allowing for repeated detection.

Figure 7:
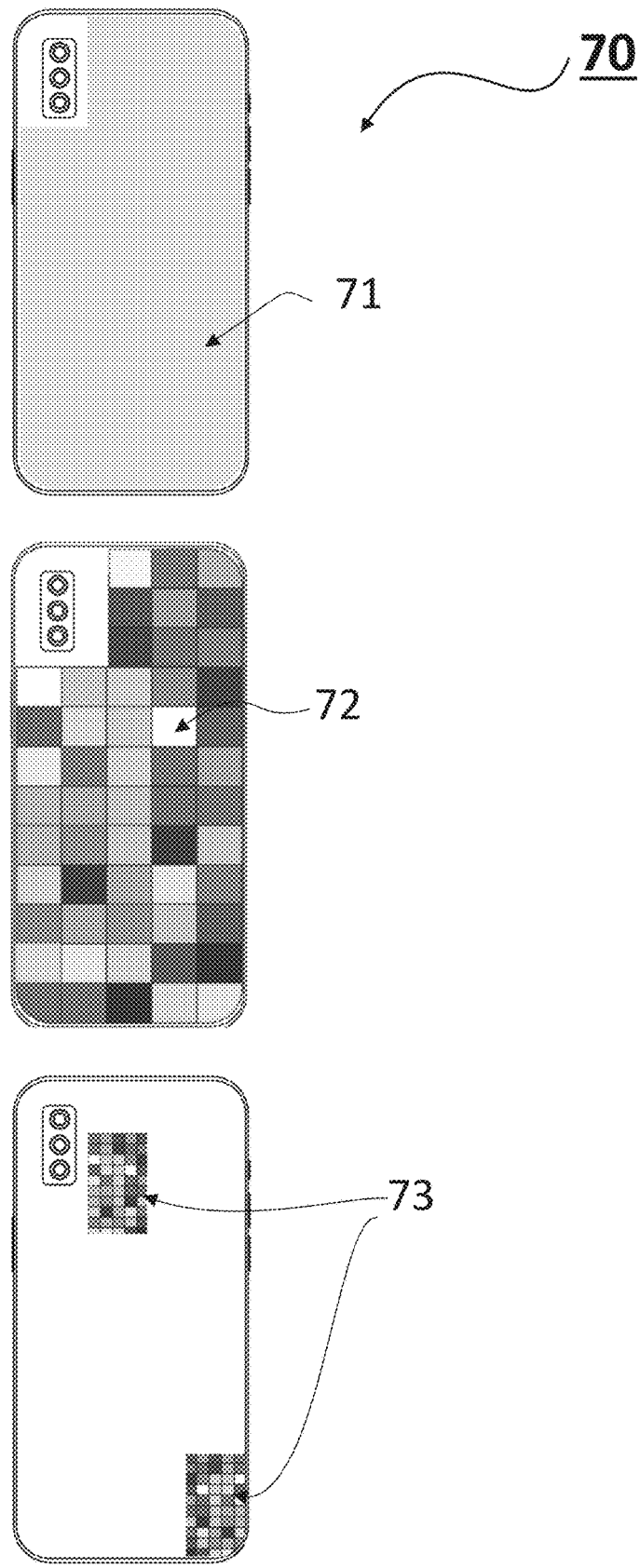
FIG. 7 shows a non-limiting embodiments of DRD detection system 70, according to the present invention, presenting sticker 71 that covers most of the area of the cellphone's back protective cover and exhibits a single active area (marked by a grey shade) on which chemically active components for detecting one or more DRDs (not shown) are applied, sticker 72, that covers most of the area of the cellphone's back protective cover and exhibits an array of several isolated regions (marked by various grey shaded rectangles) each region exhibiting chemically active components for detecting at least DRD, and sticker 73, which is similar to sticker 72 except for its size that covers a part of the cellphone's back protective cover.

FIG. 7 shows a non-limiting embodiments of DRD detection system 70, according to the present invention, presenting sticker 71 that covers most of the area of the cellphone's back protective cover and exhibits a single active area (marked by a grey shade) on which chemically active components for detecting one or more DRDs (not shown) are applied, sticker 72, that covers most of the area of the cellphone's back protective cover and exhibits an array of several isolated regions (marked by various grey shaded rectangles) each region exhibiting chemically active components for detecting at least DRD, and sticker 73, which is similar to sticker 72 except for its size that covers a part of the cellphone's back protective cover.

Referring to FIG. 7, it is noted herein that in sticker 71 the active area marked by grey exhibits chemical reagents suitable for detecting a single type of DRD, or a mixture of chemical reagents suitable for detecting more than one type of DRD. The user may contact a sample of the beverage by dotting the surface of sticker 71 or swipe over sticker 71, and if a DRD is present in the sample, the point of contacting the sample with the sticker will afford a detectable signal (e.g., color change).

Further referring to FIG. 7, it is noted herein that the plurality of isolated regions marked by various grey shaded rectangles, shown as an array in sticker 72, are not necessarily visible as isolated regions, whereas each grey shaded rectangle symbolizes an area exhibiting chemical reagents suitable for detecting one type of DRDs different that the DRD detectable in another grey shade area. The user may contact a sample of the beverage by dotting the surface of sticker 72 with the sample, or swiping over sticker 72 with the sample; if a DRD is present in the sample, the point(s) of contacting the sample with the sticker will afford a detectable signal (e.g., color change).

In some embodiments, the sticker is transparent and can serve as a cellphone screen, front or back protective cover.

The use of the sticker-type detection system is similar to any solid phase type assay.

A Stylus:

Also provided herein is a device as defined herein, comprising a DRD detection system that is implemented and/or includes a stylus. A stylus, often referred to as a digital pen, is a pen-shaped instrument used in conjunction with an electronic device such as a tablet, smartphone, or certain computer screens to enter information. It is used to assist in navigating or providing more precision when using touchscreens. Many smartphones from manufacturers such as Samsung, Google, Huawei, and Xiaomi include stylus capabilities in their phones. In some cases, the stylus slides into a slot built into the smartphone for that purpose. For cellphones that do not come with a stylus, one can purchase it separately.

In the context of the present invention, a "stylus" refers to a handheld tool designed for interaction with touchscreens and other digital interfaces, as well as a platform for a DRD detection system or parts thereof. A stylus typically features a fine-point tip, which allows users to tap, draw, write, or navigate on the screen with enhanced accuracy compared to using their fingers. According to some embodiments of the present invention, a stylus can be used to contact the beverage to be tested for DRD presence, or a sample thereof, whereas contacting can be by dipping or wetting, and can be effected for a short period of time, or continuously.

Examples of styluses for cellphone include, without limitation:

Capacitive Stylus: This type of stylus is compatible with capacitive touchscreens, which are commonly found on smartphones and tablets. It has a conductive tip that mimics the electrical properties of a human finger, enabling accurate touch input.

Active Stylus: An active stylus includes electronic components that interact with the device's touchscreen. It may offer features like pressure sensitivity and palm rejection, making it suitable for more advanced creative tasks.

Fine-tip Stylus: These styluses have a thin and fine tip that allows for detailed drawing and writing on the screen. They are often favored by artists and designers.

Universal Stylus: Some styluses are designed to work across various touchscreen devices, regardless of the brand or model. These styluses are compatible with a wide range of smartphones and tablets.

Bluetooth-enabled Stylus: These styluses connect to the device via Bluetooth and offer additional functionalities, such as shortcut buttons or customizable settings.

Multi-function Stylus: Some styluses come with dual functionality, combining a stylus tip with a regular pen or a digital brush. This allows users to switch between traditional writing and digital interaction.

Disc-tip Stylus: This type of stylus features a transparent, disc-shaped tip that provides better visibility while writing or drawing on the screen.

Magnetic Stylus: Some styluses have magnets that allow them to attach to the device's body or a magnetic case, ensuring they are easily accessible when needed.

According to an aspect of some embodiments of the present invention, there is provided a device comprising a cellphone or cellphone protective cover having a stylus acceptor (e.g., holder, slot or sheath) and a cellphone stylus acceptable is the stylus acceptor, wherein the cellphone stylus includes chemical reagents capable of a detecting at least one DRD. In such embodiments, the invention involves a device that combines the functionality of a cellphone or its protective cover with a specially designed stylus, manufactured or configured with chemical reagents for at least one DRD detection.

According to another aspect of some embodiments of the present invention, there is provided a DRD detection system that includes a cellphone stylus and at least one chemical reagent physically associated therewith capable of detecting at least one DRD.

According to yet another aspect of some embodiments of the present invention, there is provided a DRD detection device that includes a cellphone and/or cellphone protective cover having a dedicated acceptor for accepting and physically securing therein a dedicated DRD detection system and a dedicated DRD detection system physically acceptable by and securable to the acceptor.

The device may feature a designated component known as a "stylus acceptor," which essentially serves as a receptacle, holder, slot, or sheath intended to securely accommodate a specific accessory known as a "cellphone stylus." What makes this stylus unique is its integration of specialized chemical reagents with the primary function of detecting the presence of at least one DRD within a beverage sample. The stylus acceptor acts as a housing or compartment within the cellphone or protective cover, expressly designed to snugly fit the cellphone stylus. This stylus may fulfill conventional roles for touchscreen interaction, while being enhanced with the incorporation of chemical reagents; these chemical reagents are purposely selected and formulated to have the capability of detecting the presence of at least one DRD within a beverage or a sample thereof.

For example, considering a scenario where an individual is at a social gathering and wishes to ensure the safety of their beverage. They utilize the device described herein, which includes their cellphone and its protective cover equipped with the specialized stylus configured to detect at least one DRD, as described herein. When they have concerns about the drink they are about to consume, they dip the stylus, containing the specific DRD-detecting chemical reagents, into the beverage. The reagents react with any DRDs present, leading to a noticeable change in color, or another detectable alteration. This serves as an alert to the user, indicating the potential presence of a DRD in the beverage and prompting them to exercise caution or take appropriate action.

According to some embodiments of the present invention the stylus can be used as part of the DRD detection system in various configurations; for example:

Color-Changing Stylus: In this configuration, the stylus that forms a part of the DRD detection system is designed with an area that changes color when it comes into contact with a beverage or a sample containing a DRD. The stylus's surface area is coated with a specialized chemical reagent that reacts with the specific chemical properties of DRDs. When the stylus is dipped into the beverage or a sample thereof, the chemical interaction between the material and the DRD molecules triggers a color change in the area on the stylus. This color change is visually detectable and provides a clear indication of the presence of a DRD in the beverage. The color-changing stylus offers a simple and intuitive way for users to quickly assess the presence of DRDs in the beverage without the need for complex equipment.

Chemical-Reagent Stylus: In this configuration, the stylus of the DRD detection system is equipped with chemical reagents embedded within its structure. These chemical reagents are specifically designed to react with DRDs present in the beverage or sample. When the stylus is brought into contact with the beverage, the chemical reagents are released and mixed with the liquid. If a DRD is present, a chemical reaction occurs between the reagents and the DRD molecules, resulting in the release of a colored substance into the beverage. The color change is visually discernible, serving as an indicator of the presence of DRDs. This configuration provides a more controlled and controlled method of detecting DRDs, as the chemical reagents are designed to interact exclusively with the target molecules.

Continuous Monitoring Stylus: In this configuration, the stylus of the DRD detection system is designed for continuous monitoring of the beverage. The stylus is optionally equipped with elements of a DRD detection system, such as a spectra meter, a colorimeter, a pH meter, or an electrochemical sensor, is inserted into the beverage, and its active tip and it general mechanical structure allows it to remain submerged, optionally securely attached to the rim of the container. The stylus is equipped with sensors or indicators that can detect the presence of DRDs in the beverage over time. The sensors may be designed to detect changes in color, conductivity, or other relevant chemical and/or physical properties of at least one DRD. If a DRD is detected, the sensors trigger an alert or color change on the stylus itself.

Users can easily observe the change and take necessary actions. This configuration allows for real-time monitoring of the beverage's condition, making it particularly useful in scenarios where continuous surveillance is essential, such as parties or public events.

These configurations demonstrate, without limitation, different ways in which the stylus in a DRD detection system can be utilized to interact with beverages or samples to determine the presence of DRDs. Each configuration offers a unique approach to provide users with reliable and convenient information about the safety of the beverage.

Since a stylus is typically held by the user using one side thereof and while freeing the other side, the tip, for touching, in some embodiments, the region of the stylus that contacts the beverage and/or contains any chemical reagent, is near or at the contact tip of the stylus, or the distal side thereof, away from the side of the stylus that is held by the user.

In some embodiments, the stylus is used as a sample collecting tool (sampler) that can deliver a controllable amount of the beverage to a DRD detection system which is found in or on the cellphone or any of its protective covers. For example, a DRD detection assay involves placing a drop of the beverage on an area that contains chemical reagents that react with at least one DRD to produce a color change, and the drop is controllably taken and delivered by a dedicated stylus.

In some embodiments, the stylus is used as a beverage sampler. The beverage sampler features a sampling cavity, which may be a slanted hole passing through the elongated body of the beverage sampler at its distal end, allowing liquid to fill it while releasing air from the raised end of the hole. In some embodiments, the sampling cavity may be used as a chamber for examining the sample; in some non-limiting embodiments, the chamber may be used as a cuvette in a spectroscopic assay. In the context of some embodiments of the present invention, the sampling cavity is a transparent compartment near the distal end of the beverage sampler, that may be used for holding and analyzing samples in a spectra meter (e.g., spectrophotometer) or other spectroscopic devices. The sampling cavity may be formed from a transparent material, such as glass, quartz, or plastic, to allow light to pass through the sample for analysis.

According to some embodiments of the present invention, the DRD detection device includes:
(a) a cellphone;
(b) a beverage sampler, having a sampling cavity for collecting a beverage sample at its distal end;
(c) a DRD detection system which includes a spectra meter connected to and functionally communicating with the cellphone; and
(d) a first beverage sampler acceptor in the DRD detection system for positioning the sample inside the DRD detection system for allowing sample readout by the spectra meter (the first sampler acceptor may also serve for holding the sampler when not in use); and optionally
(e) a communal protective cover designed for protecting, securing and holding together the cellphone and the DRD detection system as well as an optional second beverage sampler acceptor, whereas the communal protective cover is a cellphone protective cover designed for maintaining a form-factor of the cellphone.

Figure 8:
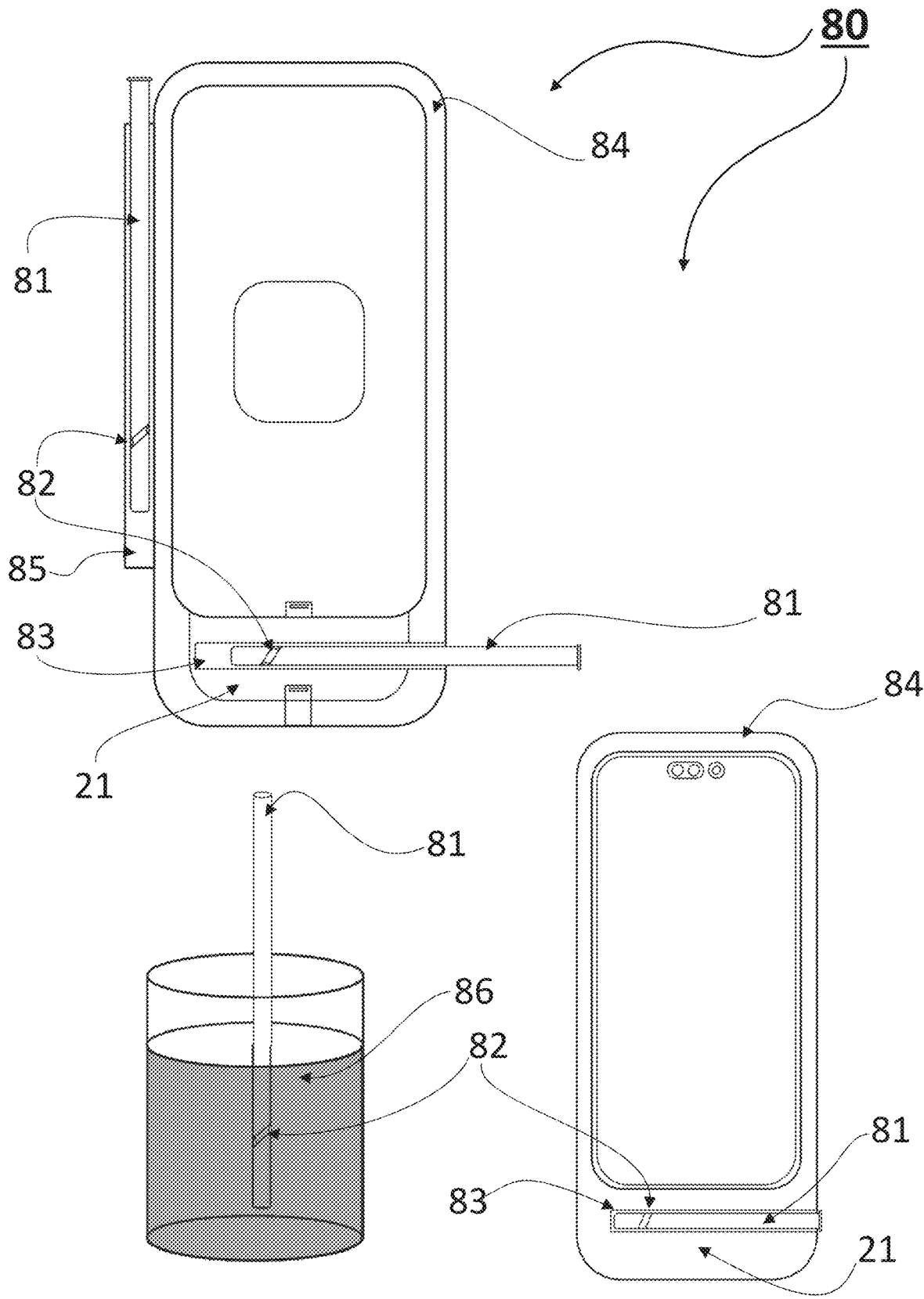
FIG. 8 presents a non-liming embodiment of DRD detection device 80 (cellphone not shown), comprising beverage sampler 81 that may be shaped and used as a cellphone stylus, exhibiting sampling cavity 82 configured to sample, hold, transfer and, in some embodiments, serve for spectroscopic measurement inside first beverage sampler acceptor 83, which places sampling cavity 82 in corresponding readout position in DRD detection system 21 used to detect at least one DRD in beverage 86, wherein DRD detection system 21 is integrated into communal protective cover 84 that may exhibit second beverage sampler acceptor 85, designed to securely house beverage sampler 81 when not in use.

FIG. 8 presents a non-liming embodiment of DRD detection device 80 (cellphone not shown), comprising beverage sampler 81 that may be shaped and used as a cellphone stylus, exhibiting sampling cavity 82 configured to sample, hold, transfer and, in some embodiments, serve for spectroscopic measurement inside first beverage sampler acceptor 83, which places sampling cavity 82 in corresponding readout position in DRD detection system 21 used to detect at least one DRD in beverage 86, wherein DRD detection system 21 is integrated into communal protective cover 84 that may exhibit second beverage sampler acceptor 85, designed to securely house beverage sampler 81 when not in use.

Further referring to FIG. 8, in some embodiments, stylus-shaped beverage sampler 81, that exhibit sampling cavity 82 as a transparent section near its distal end, may be filled with a sample of beverage 86 to be assayed spectroscopically. In such embodiments, sampling cavity 82 functions as a sampler and analyzer and serves as a convenient and portable alternative for on-the-go spectra meter measurements in DRD detection system 21. First, sampling cavity 82 is filled with a sample of beverage 86 to by dipping the distal end of beverage sampler 81 into beverage 86. The sample fills the transparent sampling cavity 82 that acts as the optical path for spectroscopic analysis. Once the user fills the transparent sampling cavity 82 with the sample, beverage sampler 81 is placed in first beverage sampler acceptor 83 that forms a part of DRD detection system 21 configured to execute a spectroscopic assay. The user than activates the spectroscopic function of DRD detection system 21. Once the spectroscopic function is activated, DRD detection system 21 emits light (often within a specific wavelength range) via a corresponding readout position therein through the liquid sample in transparent sampling cavity 82. The detector within DRD detection system 21 measures the interaction of light with the sample, and the resulting data can be displayed on a screen or transmitted to another device for analysis. Interpretation of the spectroscopic results obtained from the device may be carried out by a dedicated software and use remote serves and could computing to complete the DRD detection process.

In one embodiment, the device includes a stylus which serves as a cartridge for releasable DRD detection systems. The releasable DRD detection systems for detecting DRDs are stored inside the stylus, and are dispensed thereby into the beverage or a sample thereof, thereby contacting the releasable DRD detection system with the beverage or a sample thereof. The releasable DRD detection system may be configured to exhibit chemical reagents that are applied on the surface thereof, and are capable of colorimetrically react in the presence of at least one DRD, e.g., chemical reagents of a solid phase colorimetric assay and/or a bleeding colorimetric assay, as these are described hereinabove. The releasable DRD detection systems may take any shape that fits the stylus, namely a spheroid, a polyhedron, a toroid, a cylinder, a cone, a disk, and any other form. Preferably the releasable DRD detection systems are shaped as spheres.

Figure 9:
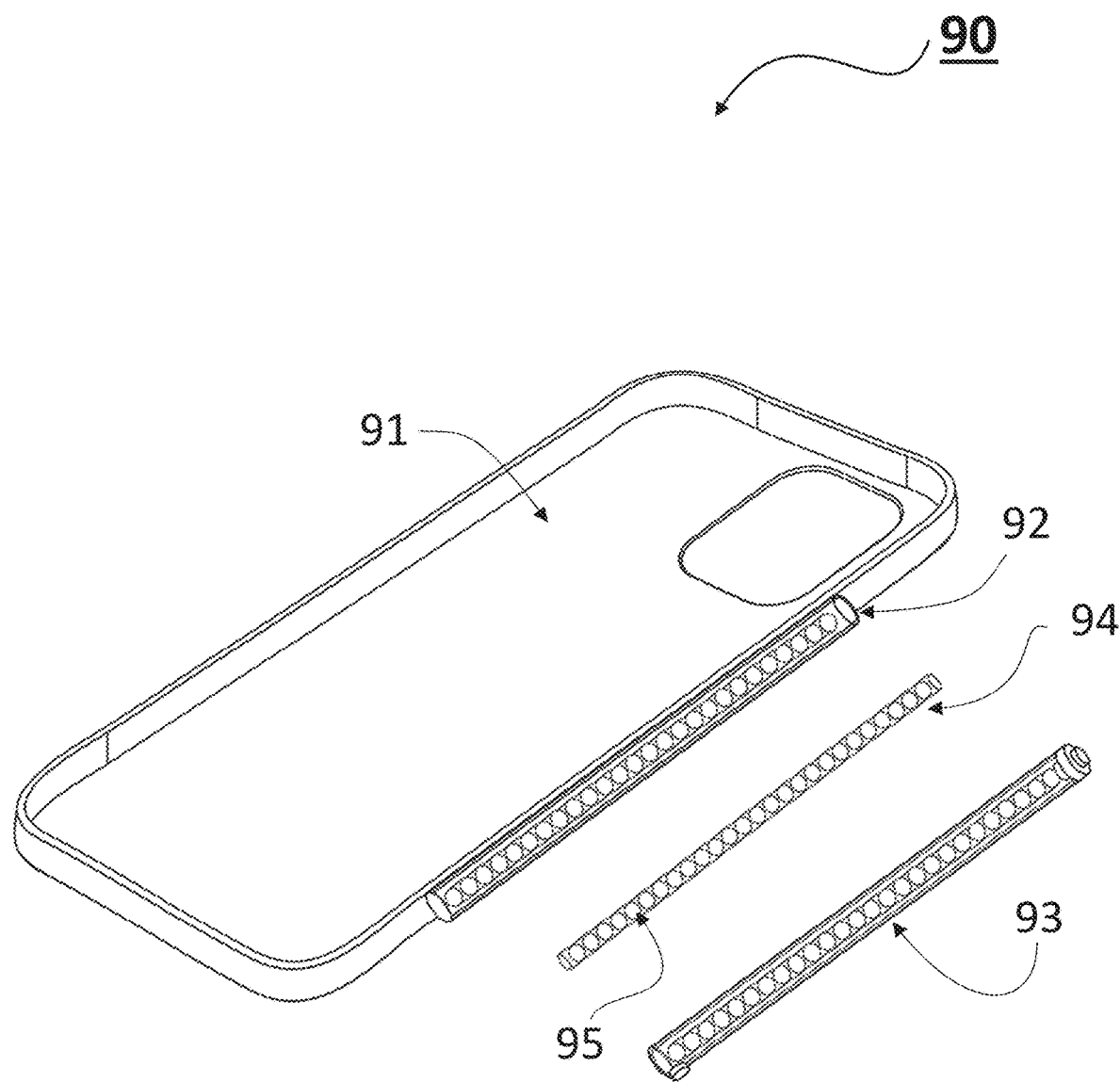
FIG. 9 presents a non-liming embodiment of DRD detection device 90 (cellphone not shown), comprising cellphone protective cover 91 equipped with stylus acceptor 92, designed to securely house stylus 93, that includes cartridge 94 configured to dispense releasable DRD detection systems 95.

FIG. 9 presents a non-liming embodiment of DRD detection device 90 (cellphone not shown), comprising cellphone protective cover 91 equipped with stylus acceptor 92, designed to securely house stylus 93, that includes cartridge 94 configured to dispense releasable DRD detection systems 95.

Further referring to FIG. 9, in some embodiments, DRD detection device 90 includes cellphone protective cover 91 equipped with dedicated cartridge 94 for housing a plurality of releasable DRD detection systems 95.

Further referring to FIG. 9, in some embodiments, DRD detection device 90 includes cellphone protective cover 91 equipped with dedicated holder 92 for holding dedicated releasable cartridge 94 in the form of an elongated member designed for housing a plurality of releasable DRD detection systems 95. In some embodiments, said elongated member may be used as a cellphone stylus.

According to some embodiments of the present invention, the releasable DRD detection systems exhibit positive buoyancy in the beverage to be assayed. Positive buoyancy allows the releasable DRD detection system to float on the liquid sample, which may be necessary to conduct a DRD detection assay and/or make the results of the assay more visible for the user, and/or allow easy removal of the releasable DRD detection system from the liquid. Thus, in some embodiments, the releasable DRD detection system has a specific mass so as to float on the surface of an alcoholic or non-alcoholic beverages. In some embodiments, the releasable DRD detection system has a specific mass that allows it to sink to the bottom of a container containing the beverage to be assayed. Thus, a releasable DRD detection system may exhibit negative buoyancy in a beverage, namely the releasable DRD detection system is designed to float at mid-depth or sink to the bottom of the container of the sample or beverage.

A releasable DRD detection system that is configured to produce a colorimetric response upon contacting at least one DRD, either by bleeding a color into its environment or by changing its color, and either sinking or floating, can serve for continuous monitoring of the beverage or sample, as long as it is in contact therewith. For example, the user takes the stylus out of its acceptor and drops one floating releasable DRD detection system that is configured for a bleeding colorimetric response into the beverage, and observe the releasable DRD detection system once it is sitting on top of the beverage. As long as the releasable DRD detection system does not bleed a color into the beverage, the user may assume that the beverage is free of DRDs. If at any point in time the releasable DRD detection system bleeds color into the beverage, the user may assume that the beverage has been spiked.

The advantage of the DRD detection systems herein is that these systems can be used for continuous monitoring if a DRD was added to a beverage while continuously present in a beverage.

Drugs Associated with Drug-Facilitated Sexual Assault:

In the context of the present invention date rape drugs (DRDs) are substances that are sometimes used to assist in committing a sexual assault. Sexual assault is any type of sexual activity that a person does not agree to. Because of the effects of these substances, victims may be physically helpless and cause impaired judgment, unable to refuse sex, and unable to remember what happened. The substances often have no color, odor or taste and are easily added to flavored drinks without the victim's knowledge. The most common date rape drugs include GHB (gamma hydroxybutyric acid), ketamine (Ketalar) and Rohypnol (flunitrazepam). Street names for GHB include Grievous Bodily Harm, Liquid G, Liquid Ecstasy, Somatomax, Cherry Meth, Easy Lay and Gamma 10. Street names for ketamine include Special K, Ket and K, Vitamin K, Kit Kat, Keller, Cat Valium, Purple and Super C. Street names for Rohypnol include Roofies, R2, Roofenol, Roche, Roachies, La Rocha, Rope, Rib, Circles, Mexican Valium, Roach-2, Roopies, Ropies, Forget Pill, Trip-and-Fall and Mind Erasers.

There are other substances that affect judgment and behavior, and can put a person at risk for unwanted or risky sexual activity, including alcohol (ethanol), which can result in impaired judgment, less ability to protect oneself and blackouts or memory loss.

GHB comes in a liquid with no odor or color, a white powder and a pill. Ketamine is a white powder and Rohypnol is a pill that dissolves in liquid.

GHB may cause any one, or a combination of drowsiness, dizziness, slow heart rate, nausea, loss of consciousness, inability to remember what happened while drugged, seizures, coma, and death.

Ketamine may cause any one, or a combination of hallucinations, lost sense of time and identity, agitation, aggressive or violent behavior, convulsions, loss of consciousness, loss of coordination, and potentially fatal respiratory failure.

Rohypnol may cause any one, or a combination of lower blood pressure, sleepiness, muscle relaxation or loss of muscle control, visual disturbances, loss of consciousness, problems talking, inability to remember what happened while drugged, and nausea.

In the context of the present invention, drugs associated with drug-facilitated sexual assault (DRDs) include, without limitation, γ-hydroxybutyrate (GHB; sodium oxybate, Xyrem), γ-butyrolactone (GBL, a precursor to GHB and has similar effects), flunitrazepam (Rohypnol, Roofies, Hypnodorm), ketamine (Ketalar, Ketanest), ketamine-like analogs (e.g., methoxetamine or MXE), carisoprodol (Soma), various benzodiazepines (Diazepam, Alprazolam, Clonazepam, Lorazepam, Temazepam, etc., a.k.a. Valium, Xanax, Klonopin, Ativan, Restoril, Normison, Temaze, etc.), benzodiazepine-like drugs such as Zolpidem, Zopiclone, a.k.a Ambien, Imovane, Intermezzo), various barbiturates (Phenobarbital, Secobarbital, Pentobarbital, etc. a.k.a. Luminal, Seconal, Nembutal, etc.), MDMA (3,4-methylenedioxymethamphetamine, a.k.a. ecstasy, Molly), scopolamine (Hyoscine, a.k.a. Transderm Scop, Scopoderm TTS, devil's breath), various opioids (morphine, heroin, fentanyl, etc.), chloral hydrate (Aquachloral, Noctec), clonidine (Catapres, Kapvay), diphenhydramine (Benadryl, Nytol), and methamphetamine (Meth, Crystal Meth).

A Method:

According to an aspect of some embodiments of the present invention, there is provided a method designed for the detection of the presence or absence of a DRD in a beverage, which is effected by contacting the DRD detection system with a beverage potentially containing the DRD, and based on the performance of the DRD detection system, e.g., DRD-detection assay results, determining the presence or the absence of the DRD is the beverage.

The key factor in this method lies in the ensuing performance of the DRD detection system. As the DRD detection system engages with the beverage, it executes the DRD-detection assay. This assay generates results that serve as the foundation for making a definitive determination. This determination involves assessing whether the beverage under scrutiny contains the DRD substance or remains free from it.

Personal Safety Enhancement: Imagine an individual in a social setting who is concerned about their safety. They use a smartphone equipped with a DRD-detection detection system. If they suspect a beverage might have been tampered with, they can discreetly use the smartphone to assay the drink. The DRD detection system's assay results quickly inform them whether the drink contains a DRD, empowering them to make informed decisions about their safety.

In essence, the described method centers around leveraging the availability and capabilities of a smartphone's specialized DRD-detection detection system to ascertain whether a beverage contains a DRD or not. This determination is made based on the results generated by the DRD detection system's DRD-detection assay, providing a valuable tool for personal safety and awareness.

A colorimetric assay for detecting a DRD in a beverage may be conducted as follows:

The DRD detecting system comprises a solid phase element configured for colorimetric assay embedded on the cellphone's protective cover. The detecting system is in the form of a sticker affixed to the back of the cellphone's protective cover, wherein the sticker comprises chemical reagents that are selected and designed to interact with at least one DRD, while the interaction causes the area of the sticker one which the chemical reagents are present to change color and/or to emit light. The sticker is optionally divided into several regions, each comprising chemical reagents that are selected and designed to interact with a specific DRD or a specific group of DRDs (e.g., related by chemical properties or otherwise detectible by the same chemical reagents). The sticker is optionally protected by a removable protective film or layer. The sticker may further be divided into sections, each provides the means to conduct one DRD detection assay.

A small sample of the beverage is contacted with a surface comprising solid phase chemical reagents that are present in a designated area on the cellphone's protective cover, which forms a part of the DRD detection system;

The collected sample is contacted with one or more chemical reagents on the cellphone's cover by dipping a tip of a finger in the beverage and swiping the wet part of the finger with one or more areas on the cover, which at least one area comprises chemical reagents that interact with the DRD and produce a colorimetric signal, namely chemical reagents that are purposely selected to effect a color changing reaction upon contacting at least one DRD;

If a DRD is present in the sample of the beverage, the area that was contacted with the sample or the sample itself will change color.

In another example, the device includes a retractable or folding element that includes solid phase chemical reagents that interact with the DRD and produce the colorimetric signal.

In some embodiments, the device analyzes spectral data obtained from the sample by comparing the spectral data to pre-loaded spectral data information stored in the cellphone or on a remote location (a network server, a cloud, etc.), to determine whether the drug is present; and An exemplary GHB detection assay, according to some embodiments of the present invention, involves a specially designed sticker with specific chemical reagents to detect the presence of GHB (gamma-hydroxybutyrate) in a beverage. The sticker's surface is coated with a layer of reagents that undergo a selective chemical reaction with GHB, leading to a distinct color change upon contact. The chemistry on the sticker involves immobilized reagents that react with GHB through an esterification reaction. The reagents include a carboxylic acid compound, such as succinic anhydride, and a pH indicator dye, such as bromothymol blue. The reaction takes place in an aqueous environment upon contact with the beverage containing GHB.

When a drop of the beverage is placed on the designated region of the sticker, GHB reacts with the carboxylic acid compound present on the sticker's surface. This reaction results in the formation of an ester compound, releasing hydrogen ions in the process. The pH indicator dye, bromothymol blue, responds to the change in pH by shifting its color. In the absence of GHB, the sticker retains its original color. However, in the presence of GHB, a notable color change occurs, indicating a positive result for GHB detection.

Specifically, a GHB detection assay is effected by using a colorimetric enzymatic assay. This type of assay is based on the oxidation of GHB to succinic semi-aldehyde (SSA), a reaction that occurs during metabolism in vivo via the enzyme GHB-dehydrogenase (GHB-DH). The particulars of this solid phase assay can be adapted to the sticker-based DRD detection system from several publications, including, for example, Ingels, AS.M.E. et al. ["*Screening and confirmation methods for GHB determination in biological fluids*", *Anal Bioanal Chem*, 2014, 406, 3553-3577], and Bravo D T et al. ["*Reliable, sensitive, rapid and quantitative enzyme-based assay for gamma-hydroxybutyric acid (GHB)*", *J Forensic Sci.*, 2004, 49(2), pp. 379-87], all of which are incorporated by reference in their entirety as if fully set forth herein.

An exemplary electrochemical assay for detecting flunitrazepam, according to some embodiments of the present invention, is based on screen-printed graphene electrodes, and was developed by Enriqueta Garcia-Gutierrez and Carlos Lledo-Fernandez ["Electroanalytical Sensing of Flunitrazepam Based on Screen Printed Graphene Electrodes", Chemosensors, 2013, 1(3), 68-77; incorporated by reference in its entirety as if fully set forth herein]. The assay has an excellent analytical performance for the detection of flunitrazepam and can be used to quantify low levels of the drug in buffer solutions as well as in alcoholic beverages.

An alternative exemplary electrochemical assay for detecting flunitrazepam is based on screen-printed graphite electrodes without the need for any additional pre-treatment or modification. This assay was developed by Jamie P. Smith et al. ["Forensic electrochemistry: the electroanalytical sensing of Rohypnol® (flunitrazepam) using screen-printed graphite electrodes without recourse for electrode or sample pre-treatment", Analyst, 2013,138, 6185-6191; incorporated by reference in its entirety as if fully set forth herein] and can be used to quantify low levels of flunitrazepam in buffered solutions as well as in beverage drinks without any sample pre-treatment.

Both of these assays are adapted for implementation in the device provided herein to offer a rapid, cost-effective, yet suitably sensitive and accurate solution for the detection of flunitrazepam in beverages.

An assay for detecting flunitrazepam using screen-printed graphene or graphite electrodes on a permanently attached appendage that extends from a cellphone could be performed as follows:

The graphene electrodes are printed on an appendage that extends from a cellphone protective cover. The cellphone may be used to provide electric power, computing capabilities, software, and display necessary for running the assay. The appendage is connected to the cellphone via cable or wirelessly, and the necessary software is installed on the cellphone.

The appendage with the screen-printed graphene electrodes is inserted into the sample (beverage), making sure that the electrodes are in contact with the sample, and the assay is initiated by running the software on the cellphone. The software controls the application of a potential to the electrodes and measures the resulting current. The current is proportional to the concentration of flunitrazepam in the sample.

The software analyzes the data and displays the results on the cellphone screen. The results indicate whether flunitrazepam is present in the sample and, if so, its concentration. This assay does not require any additional reagents or tools, other than those mentioned above (i.e., the cellphone, appendage with screen-printed graphene electrodes, and software). The assay can be performed quickly and easily, making it a convenient tool for detecting flunitrazepam in beverages. The device generates a visual, vibrational and/or audible signal intended for the user, providing an indication of presence of a DRD in the beverage.

The invention is not limited to the mode of detection of any particular DRD, or to any type of assay, or to any element or module that forms a part of the DRD detection system. As such, a skilled artisan would appreciate the abundance of guidance and information pertaining to assays, protocols and means for the detection and/or identification of any DRD. Provided below are some exemplary sources of information that is relevant to the implementation of the present invention, all of which are incorporated by reference in their entirety as if fully set forth herein. Following is a list of documents containing information pertaining to various methods/instruments of detecting DRDs. The methods/instruments described in these documents can be adapted by any person ordinarily skilled in the art for use in context of the various DRD detection systems describe herein. Each of the documents is therefore incorporated by reference in its entirety as if fully set forth herein.

Document ID Document Title
US 54115209 A Drug detection straw
US 201113206506 A Drug detection device
US 201213370070 A Discrete, hidden fingernail mounted date rape drug detection device
US 201113204708 A System and method for detection of a contaminated beverage
GB 0118507 A Proofers date rape drug detection
US 201113083580 A Method and apparatus for detecting date rape drugs in a liquid
US 201414156249 A Date rape drug detector
US 201715434557 A System and method for detection of a contaminated beverage
US 201514862105 A Wearable technology that monitors health and safety
US 201715606119 A Methods and apparatus for detecting compounds in liquids
US 201816612559 A Adaptable detection apparatus
US 201716320294 A Apparatus, system, and method for detecting a target substance
U.S. 63/677,200 A Antigen detection device and method
GB 0508182 A Electronic device for detecting contaminants in drinks
US 202117523306 A Methods and apparatus for detecting incapacitating drugs
US 201113991983 A Methods and kits for detection of drugs
GB 0415970 A A device for preventing illicit contamination of potable liquids
GB 2015052013 W Portable method for the detection of drugs
US 202017024620 A Rapid methanol detection device
US 201414553537 A Wearable device for detection of contaminants and method thereof
EP 20212850 A Gamma-hydroxybutyric acid detector sticker and method of manufacturing same
U.S. 62/470,303 A Personal illicit drug detection method
US 201113808810 A Pharmaceutical form for combating chemical submission of a medicament
US 77413201 A Narcotics detector test strips for a beverage
EP 16158820 A An electronic coaster for identifying a beverage
GB 2004005261 W Apparatus for detecting drugs in a beverage
US 2021/0021243 W Devices and methods for detecting a target analyte of interest
EP 2014062569 W Detection of indications of psychoactive components in a liquid
US 90796910 A Nonvisual indication of an unwanted chemical in an ingestible substance
PL 2007000013 W A method of manufacturing a test for the detection of narcotics, particularly gamma-hydroxybutiric acid (ghb), and a method of detecting their presence
ES 202030841 A New Tiourea base compounds, obtaining procedure and its use in the detection of GHB in beverages (Machine-translation by Google Translate, not legally binding)
US 201213554178 A Molecularly imprinted polymer sensing method
ES 202030840 A New compounds derived from benzoxazole, obtaining procedure and its use in the detection of GHB in beverages (Machine-translation by Google Translate, not legally binding)
U.S. Ser. No. 15/050,508 A Buoyant-capable beverage and food content-sensor
DK 2022050277 W Detection case for portable device
US 2015/0055994 W Nonvisual indication of an unwanted chemical in an ingestible substance
US 201514658018 A Nonvisual indication of an unwanted chemical in an ingestible substance
US 201314433177 A Instrument for analysing compounds
US 50326009 A Detechip: molecular color and fluorescent sensory arrays for small molecules
US 201514684022 A Portable chemical testing apparatus, system, and method
US 2018/0035187 W Integrated devices for rapid detection of benzodiazepines or other drugs in solution
US 202217682404 A Apparatus and method for determination of banned substances
US 201514742440 A Device for Detecting Blood Analytes Transdermally
EP 2020077657 W Wristband for testing for k.o. drops
US 201013318054 A Methods for determining the concentration of gamma-hydroxy butyric acid (GHB) in a sample
US 2004/0024799 W Dye solutions for use in methods to detect the prior evaporation of anhydrous ammonia and the production of illicit drugs
EP 21838558 A Reagent composition for detecting illicit drugs and sheet kit for detecting illicit drugs comprising same
US 59882304 A Apparatus for detecting gamma hydroxybutyrate, ketamines and related drugs in beverages
U.S. Pat. No. 9,881,102 A Methods, compositions and apparatuses for detection of gamma-hydroxybutyric acid (GHB)
US 202017606225 A Proximity-driven activation of crispr-cas systems for detection of diverse molecular analytes
US 2020/0030032 W Proximity-driven activation of crispr-cas systems for detection of diverse molecular analytes
US 0000030 W Extraction material and method for determination of gamma-hydroxybutyrate
US 99989304 A Ampoule and method of use
US 94622501 A Method for identification of flunitrazepam
US 201113092736 A Ampoule dispenser assembly and process US 44631303 A Rapid-acting drug analysis system
US 201916241217 A Production of salts of 4-hydroxybutyrate using biobased raw materials
GB 2005004394 W Apparatus for preventing the addition of a foreign substance to a drink
US 201715635798 A Dispenser having applicator connector member
U.S. Ser. No. 16/699,298 A Beverage analysis sample
U.S. 60/702,600 A Method for detection of 4-hydroxybutyric acid and its precursor(s) in fluids
US 202117302743 A System and method for measuring acute and chronic stress
EP 2017073949 W Method and sensor array for identifying an analyte
U.S. Pat. No. 6,260,105 A Video surveillance data analysis algorithms, with local and network-shared communications for facial, physical condition, and intoxication recognition, fuzzy logic intelligent camera system
US 202017598076 A Devices for generation of electromagnetic radiation of predetermined profile
US 201213428232 A Antidotes for nitrobenzodiazepines
EP 12158309 A Dispenser
EP 2022069170 W Lauflumide and derivatives thereof for treating chronic fatigue syndrome and myalgic encephalomyelitis/chronic fatigue syndrome (me/cfs)
US 202017131538 A Ultrasensitive and multiplexed cell-free biosensors using cascaded amplification and positive feedback
US 2020/0063133 W Ultrasensitive and multiplexed cell-free biosensors using cascaded amplification and positive feedback
US 2008/0087123 W Container assembly
US 95913607 A Container assembly
US 95905607 A Container assembly
US 95909507 A Container assembly
EP 07761426 A Multi-chambered dispenser
EP 15813093 A Control system for control of distribution of medication
US 0335156 W Ghb treatment methods
US 201917265785 A On demand, portable, cell-free molecular sensing platform
EP 05800783 A Dispenser and process
US 201414217023 A Money bill authentication and theft prevention system
US 202017593026 A Riboswitch-based fluoride sensing in cell-free extract
US 202217811671 A Dispenser actuator assembly
U.S. Pat. No. 9,066,598 A Prisoner tracking and warning system and corresponding methods
GB 2021050068 W A holographic sensor
US 202117645408 A Dispenser actuator assembly
US 202017098367 A System and Method for Electronically Consenting to Engage in Sexual Activity
EP 17187249 A Multi-chambered dispenser
US 2006/0006730 W A registry method and control system for DEA schedule ii-v medicines
US 2022/0018133 W Cell-free biosensors with DNA strand displacement circuits
US 201916598928 A Dispenser actuator assembly
EP 20194721 A Dispenser actuator assembly
US 202017011709 A Dispenser actuator assembly
US 2019/0037561 W Compositions and methods for treatment of narcolepsy and related disorders
U.S. 66/970,503 A Drug discovery method and apparatus
US 82956301 A Method for assaying biological and other constituents using synthetic nucleounits in lateral flow, liquid, and dry chemistry techniques
US 201614993898 A Fiber Based Molecularly Imprinted Polymers for the Removal of a Significant Fraction of Target Imprintable Entities According to some embodiments of the invention the DRD detection device may include elements which are inherent to the cellphone, in some embodiments all the hardware elements and optionally some general-purpose software elements of the detection device are inherent to the cellphone, provided that at least one part of hardware and/or software are not inherent to the cellphone. As an example, a dedicated application that allows the detection of DRDs may be the sole addition to a cellphone, which application is designed to operate physical and software components of the cellphone to render the cellphone capable of detecting DRDs and reporting of their presence or absence.

As is further explained above, irrespective of the method employed, analyzing the presence or absence of a DRD is a beverage may be complex due to its low concentration and the presence of many other substances therein.

Examples of non-alcoholic beverages commonly consumed in bars, pubs and parties include:

Water, Soda (Coca-Cola, Pepsi, etc.), Ginger ale, Tonic water, Lemonade, Iced tea, Coffee, Hot tea, Fruit punch, Cranberry juice, Orange juice, Apple juice, Pineapple juice, Grapefruit juice, Tomato juice, Cranberry soda, Club soda, Energy drinks (Red Bull, Monster, etc.), Sparkling water, Root beer, Shirley Temple, Virgin Mojito, Virgin Pina Colada, Fruit smoothies, Milkshakes, Chocolate milk, Hot cocoa, Virgin Bloody Mary, Shirley Temple, Arnold Palmer (half iced tea, half lemonade), Virgin Margarita, Virgin Daiquiri, Virgin Piña Colada, Virgin Mojito, Shirley Temple, Roy Rogers, Lemon-lime soda, Grape soda, Cream soda, Limeade, Fruit-infused water, Agua fresca, Sparkling lemonade, Italian soda, Coconut water, Non-alcoholic beer, Virgin Mary, Raspberry lemonade, Strawberry lemonade, Peach iced tea, Mint lemonade, Cucumber water, Blueberry lemonade, Hibiscus tea, Honeydew melon smoothie, Watermelon agua fresca, Elderflower cordial, Lavender lemonade, Green tea, Jasmine tea, Chai latte, Pumpkin spice latte, Matcha latte, Horchata, Pineapple coconut cooler, Mango lassi, Kiwi strawberry smoothie, Blackberry mint lemonade, Rosemary-infused lemonade, Grapefruit mint cooler, Passion fruit iced tea, Peach Bellini mocktail, Virgin Moscow Mule, Caramel iced coffee, Mint julep mocktail, Blueberry basil lemonade, Raspberry iced tea, Mango pineapple smoothie, Watermelon mint agua fresca, Cherry limeade, Cucumber cooler, Hibiscus iced tea, Honey lavender latte, Vanilla bean frappuccino, Strawberry banana smoothie, Raspberry peach iced tea, Apple cinnamon iced tea, Cranberry orange spritzer, Grapefruit ginger fizz, Kiwi cucumber cooler, Mint chocolate chip frappe, Lemon raspberry slush, Peach green tea, Blueberry mojito mocktail, Mango ginger smoothie, Strawberry watermelon cooler, Pineapple mint agua fresca, Raspberry white hot chocolate, Lavender honey iced latte, Coconut mocha frappuccino.

Examples of common alcoholic beverages consumed in pubs, bars and parties include:

Beer, Lager, Ale, Stout, IPA (India Pale Ale), Wheat beer, Pilsner, Pale ale, Porter, Cider, Whiskey, Vodka, Rum, Gin, Tequila, Brandy, Scotch, Bourbon, Rye whiskey, Irish whiskey, Sake, Wine, Red wine, White wine, Rosé wine, Champagne, Sparkling wine, Prosecco, Martini, Margarita, Mojito, Daiquiri, Cosmopolitan, Old Fashioned, Manhattan, Negroni, Sazerac, Pina Colada, Caipirinha, Sangria, Mai Tai, Moscow Mule, Irish Coffee, Long Island Iced Tea, Jagerbomb, Mimosa, Screwdriver, Bloody Mary, Sex on the Beach, Bellini, Mojito, Piria Colada, White Russian, Tom Collins, Tequila Sunrise, Whiskey Sour, Paloma, White Russian, Aperol Spritz, Irish Car Bomb, Sidecar, French 75, Dark and Stormy, Mint Julep, Amaretto Sour, Zombie, Blue Lagoon, Singapore Sling, Kamikaze, Grasshopper, Black Russian, Zombie, French Martini, Mojito, Margarita, Hurricane, Rusty Nail, Gimlet, White Lady, Aviation, Bellini, Whiskey Smash, Irish Coffee, Bramble, Caipiroska, Piria Colada, Spritz, Mojito, Sangria, Dark and Stormy, Bloody Mary, Sazerac, Bellini, Manhattan, Mojito, Margarita, Daiquiri, Old Fashioned, Martini, Whiskey Sour.

Following is a partial list of the ingredients used in the preparation of the alcoholic beverages listed above:

1. Beer—Water, Malted barley, Hops, Yeast
2. Lager—Water, Malted barley, Hops, Yeast
3. Ale—Water, Malted barley, Hops, Yeast
4. Stout—Water, Malted barley, Hops, Yeast, Roasted barley
5. IPA (India Pale Ale)—Water, Malted barley, Hops, Yeast
6. Wheat beer—Water, Malted wheat, Malted barley, Hops, Yeast
7. Pilsner—Water, Malted barley, Hops, Yeast
8. Pale ale—Water, Malted barley, Hops, Yeast
9. Porter—Water, Malted barley, Hops, Yeast
10. Cider—Apple juice, Yeast
11. Whiskey—Malted barley, Corn, Rye, Wheat, Water
12. Vodka—Distilled grains or potatoes, Water
13. Rum—Sugarcane juice or molasses
14. Gin—Neutral spirit, Juniper berries, Botanicals (such as coriander, citrus peel, or angelica root)
15. Tequila—Blue Agave plant
16. Brandy—Distilled wine or fruit juice
17. Scotch—Malted barley, Water, Yeast
18. Bourbon—Corn, Malted barley, Rye or wheat, Water
19. Rye whiskey—Rye, Malted barley, Water, Yeast
20. Irish whiskey—Malted barley, Water, Yeast
21. Sake—Rice, Water, Koji mold
22. Wine—Fermented grapes
23. Red wine—Fermented red grapes
24. White wine—Fermented white grapes
25. Rosé wine—Fermented red or white grapes
26. Champagne—Fermented grapes, Yeast, Sugar
27. Sparkling wine—Fermented grapes, Yeast
28. Prosecco—Glera grapes
29. Martini—Gin or Vodka, Dry vermouth, Olive or lemon twist (for garnish)
30. Margarita—Tequila, Lime juice, Orange liqueur, Salt (for rimming the glass), Lime wedge (for garnish)
31. Mojito—White rum, Lime juice, Sugar, Mint leaves, Soda water
32. Daiquiri—White rum, Lime juice, Simple syrup
33. Cosmopolitan—Vodka, Cranberry juice, Lime juice, Triple sec
34. Old Fashioned—Whiskey or Bourbon, Sugar, Angostura bitters, Orange twist (for garnish)
35. Manhattan—Whiskey or Bourbon, Sweet vermouth, Angostura bitters, Cherry (for garnish)
36. Negroni—Gin, Campari, Sweet vermouth, Orange twist (for garnish)
37. Sazerac—Rye whiskey, Absinthe or Herbsaint, Sugar, Peychaud's bitters, Lemon twist (for garnish)
38. Pina Colada—Rum, Pineapple juice, Coconut cream
39. Caipirinha—Cachaça, Lime, Sugar
40. Sangria—Red or White wine, Brandy, Fruit (such as oranges, lemons, or apples), Soda water
41. Mai Tai—Rum, Lime juice, Orange liqueur, Orgeat syrup, Dark rum (float)
42. Moscow Mule—Vodka, Ginger beer, Lime juice, Lime wedge (for garnish)
43. Irish Coffee—Irish whiskey, Hot coffee, Sugar, Whipped cream (optional)
44. Long Island Iced Tea—Vodka, Rum, Tequila, Gin, Triple sec, Lemon juice, Cola
45. Jagerbomb—Jagermeister, Energy drink
46. Mimosa—Champagne, Orange juice
47. Screwdriver—Vodka, Orange juice
48. Bloody Mary—Vodka, Tomato juice, Worcestershire sauce, Hot sauce, Lemon juice, Celery salt, Pepper, Celery stalk (for garnish)
49. Sex on the Beach—Vodka, Peach schnapps, Cranberry juice, Orange juice
50. Bellini—Prosecco, Peach purée or peach schnapps
51. Mojito—White rum, Lime juice, Sugar, Mint leaves, Soda water
52. Piña Colada—Rum, Pineapple juice, Coconut cream
53. White Russian—Vodka, Coffee liqueur, Cream or milk
54. Tom Collins—Gin, Lemon juice, Simple syrup, Soda water
55. Tequila Sunrise—Tequila, Orange juice, Grenadine
56. Whiskey Sour—Whiskey, Lemon juice, Simple syrup
57. Paloma—Tequila, Grapefruit soda, Lime juice, Salt (for rimming the glass)
58. White Russian—Vodka, Coffee liqueur, Cream or milk
59. Aperol Spritz—Aperol, Prosecco, Soda water, Orange slice (for garnish)
60. Irish Car Bomb—Guinness beer, Irish whiskey, Irish cream liqueur
61. Sidecar—Cognac, Orange liqueur, Lemon juice, Sugar (optional, for rimming the glass)
62. French 75—Gin, Champagne, Lemon juice, Sugar
63. Dark and Stormy—Rum, Ginger beer, Lime juice
64. Mint Julep—Bourbon, Mint leaves, Sugar, Water
65. Amaretto Sour—Amaretto liqueur, Lemon juice, Simple syrup
66. Zombie—Rum, Lime juice, Pineapple juice, Orange juice, Grenadine, Apricot brandy
67. Blue Lagoon—Vodka, Blue curacao, Lemonade
68. Singapore Sling—Gin, Cherry liqueur, Pineapple juice, Lime juice, Soda water
69 Kamikaze—Vodka, Lime juice, Triple sec
70. Grasshopper—Crème de menthe, Crème de cacao, Cream
71. Black Russian—Vodka, Coffee liqueur
72. Zombie—Rum, Lime juice, Pineapple juice, Orange juice, Grenadine, Apricot brandy
73. French Martini—Vodka, Raspberry liqueur, Pineapple juice
74. Mojito—White rum, Lime juice, Sugar, Mint leaves, Soda water
75. Margarita—Tequila, Lime juice, Orange liqueur, Salt (for rimming the glass), Lime wedge (for garnish)
76. Hurricane—Rum, Passion fruit syrup, Lemon juice
77. Rusty Nail—Scotch whisky, Drambuie
78. Gimlet—Gin or Vodka, Lime juice, Simple syrup
79. White Lady—Gin, Triple sec, Lemon juice, Egg white
80. Aviation—Gin, Maraschino liqueur, Crème de violette, Lemon juice
81. Bellini—Prosecco, Peach purée or peach schnapps
82. Whiskey Smash—Whiskey, Lemon juice, Mint leaves, Simple syrup
83. Irish Coffee—Irish whiskey, Hot coffee, Sugar, Whipped cream (optional)

84. Bramble—Gin, Blackberry liqueur, Lemon juice, Simple syrup
85. Caipiroska—Vodka, Lime, Sugar
86. Piña Colada—Rum, Pineapple juice, Coconut cream
87. Spritz—Prosecco, Aperol or Campari, Soda water, Orange slice (for garnish)
88. Mojito—White rum, Lime juice, Sugar, Mint leaves, Soda water
89. Sangria—Red or White wine, Brandy, Fruit (such as oranges, lemons, or apples), Soda water
90. Dark and Stormy—Rum, Ginger beer, Lime juice
91. Bloody Mary—Vodka, Tomato juice, Worcestershire sauce, Hot sauce, Lemon juice, Celery salt, Pepper, Celery stalk (for garnish)
92. Sazerac—Rye whiskey, Absinthe or Herbsaint, Sugar, Peychaud's bitters, Lemon twist (for garnish)
93. Bellini—Prosecco, Peach purée or peach schnapps
94. Manhattan—Whiskey or Bourbon, Sweet vermouth, Angostura bitters, Cherry (for garnish)
95. Mojito—White rum, Lime juice, Sugar, Mint leaves, Soda water
96. Margarita—Tequila, Lime juice, Orange liqueur, Salt (for rimming the glass), Lime wedge (for garnish)
97. Daiquiri—Rum, Lime juice, Simple syrup
98. Old Fashioned—Whiskey or Bourbon, Sugar, Angostura bitters, Orange twist (for garnish)
99. Martini—Gin or Vodka, Dry vermouth, Olive or lemon twist (for garnish)
100. Whiskey Sour—Whiskey, Lemon juice, Simple syrup Each one of these ingredients and their sub-ingredients and sub-sub ingredients has defined chemical and/or physical characteristics. The physical and/or chemical characteristics include, inter alia, various spectra, as this term is defined hereinabove. According to some embodiments of the invention, the spectra, as well as the spectra of water and alcohol, are stored in a memory device which can be, inter alia, the memory of the cellphone itself and/or of a remote server such as a cloud server with which the cellphone communicates, e.g., via a dedicated DRD detection cellphone application and the data communication abilities inherent to the cellphone. In an embodiment of the invention, when the DRD detection system of the DRD detection device of the present invention is used to analyze spectra of a an unknown, DRD tempered or untampered beverage, it communicates with the cellphone and uses the application to compare the spectra of the tested beverage to the stored spectra of the beverage, its ingredients, sub ingredients, sub-sub ingredients and so on and the various spectra of DRDs to more accurately determine the presence or absence and type, concentration or amount of the DRD in the tested beverage.

Figure 10:
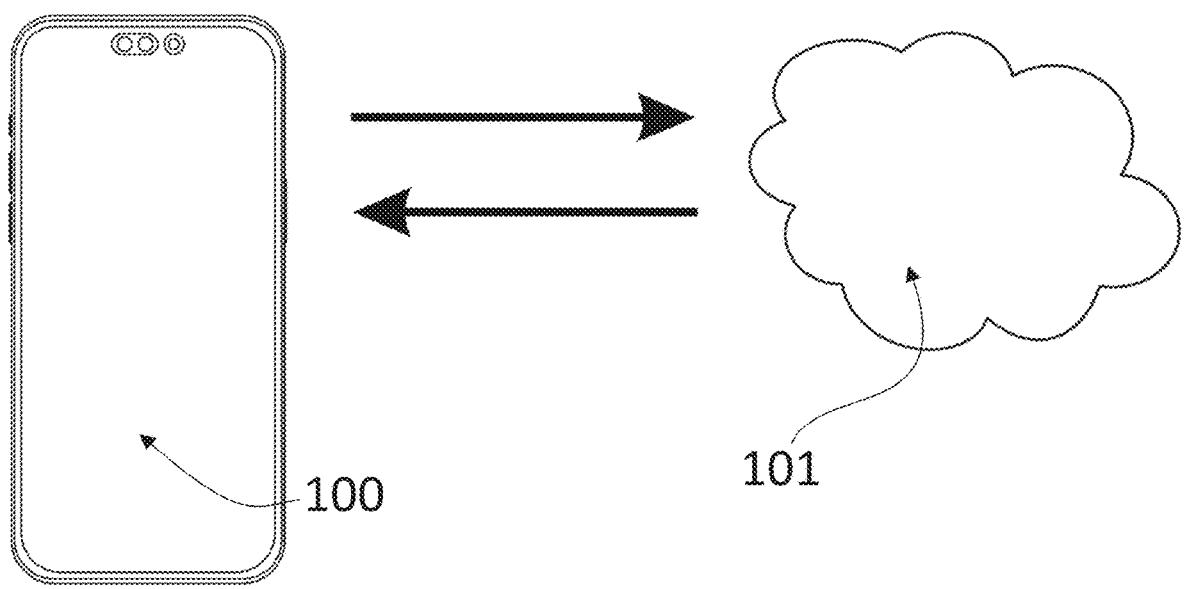
FIG. 10 illustrates DRD detection device 100, according some embodiments of the present invention, in communication with remote server (cloud) 101.

FIG. 10 illustrates DRD detection device 100, according some embodiments of the present invention, in communication with remote server (cloud) 101.

The DRD detection system can also be made to operate using artificial intelligence (AI) pre-trained as follows: Spectra of any given beverage and containing or not containing therein one or more DRDs are measured multiple times and serve as a training set for the AI. Thereafter the trained AI can be used to identify a type of beverage and the presence or absence, concentration or amount of any DRD present in the beverage.

Either way, the result of detection can be displayed using the application by the cellphone in any one or more of the following forms, e.g., an alarming visual, audial and/or vibratory signal should a DRD detected and in some embodiments of the invention further accompanied by more information describing the DRD, such as its chemical name and structure, concentration, amount, common (street) name and the expected cognitive and/or physical influence the DRD may inflict when consumed in sufficient amount, among other. If no DRD is detected, the application may operate the cellphone to issue a relaxing notification. When a DRD is detected, the application may further operate the cellphone to perform one of the following: call local authorities for help; call SOS as defined in the phone for help; call a family member or a friend for help; provide instructions how to treat a user which happened to consume the DRD.

Artificial Intelligence:

Artificial Intelligence (AI) has rapidly advanced in recent years, largely due to the availability of big data and the development of sophisticated AI training protocols. Big data refers to vast amounts of structured and unstructured data that can be analyzed to extract valuable insights. AI training protocols involve the process of training AI models using large-scale datasets to enable them to learn and perform specific tasks.

Big data plays a crucial role in AI training as it provides the raw material for training models. The abundance of data allows AI algorithms to learn patterns, correlations, and relationships that humans may not easily discern. This enables AI models to make predictions, recognize patterns, and perform complex tasks with exceptional accuracy and efficiency.

AI training protocols involve several stages. Firstly, a diverse and representative dataset is collected, containing examples relevant to the task at hand. This dataset is then preprocessed to clean, normalize, and transform the data into a suitable format for training. Next, the AI model is trained using algorithms that analyze the data and adjust the model's internal parameters to optimize its performance. This process often involves iterative training cycles to improve the model's accuracy and robustness.

To train an AI machine to identify a plurality of date rape drugs (DRDs) spectra that may be present or absent in a variety of beverages and deploy it once trained, some or all of the following steps should be employed:

1. Big Data Collection: Prepare a diverse dataset of a variety of beverage samples, including sample positive and negative for various DRDs to form a matrix (type of sample X type of DRD(s)) samples.

2. Spectra Acquisition: Carefully acquire the spectra of the beverage samples in the matrix, using a spectra meter identical or similar to the spectra meter that is used in the DRD detection device of the invention to generate a comprehensive matrix set of spectral data, capturing the unique characteristics of each sample.

3. Data Preprocessing: Clean and preprocess the spectra meticulously to eliminate any potential noise or artifacts that might interfere with the accuracy of subsequent analyses. It is crucial to normalize the spectra to ensure consistency across the samples. Furthermore, if the spectra were acquired at different resolutions or wavelengths, aligning them appropriately becomes necessary.

4. Annotation and Labeling: Annotating the dataset by meticulously labeling each sample with the presence or absence of specific DRD spectra. This manual labeling process serves as the ground truth for training the AI model, providing the necessary reference for subsequent classification.

5. Model Training: Employ machine learning techniques, such as deep learning architectures or support vector machines, to initiate the training process of the AI model. By feeding the preprocessed spectra as input and corresponding labels as output, the model will learn to associate specific spectra patterns with the presence or absence of DRD.

6. Model Optimization: Engage an iterative process of fine-tuning the AI model by carefully adjusting hyperparameters, refining the model architecture, or experimenting with different training algorithms. The objective is to optimize the model's performance and enhance its accuracy in identifying DRD within beverage samples.

7. Evaluation and Validation: Rigorously evaluate the trained model's performance using separate validation datasets that were not utilized during the training phase. Assess a range of metrics, including precision, recall, and accuracy, to comprehensively evaluate how well the AI model can identify and classify DRDs within previously unseen beverage samples.

8. Iterative Improvement: Analyze the model's performance, scrutinize any potential shortcomings or misclassifications, and embark on an iterative improvement process. This may involve incorporating additional data to augment the dataset, refining preprocessing techniques to better handle noise or artifacts, or even modifying the model architecture to enhance its capacity for accurate classification.

9. Deployment and Monitoring: Once the AI model demonstrates satisfactory performance, proceed to deploy it for practical use in real-world scenarios. Continuously monitor its performance, gather feedback, and periodically update the model to adapt to new DRDs and/or variations in beverage preparation techniques.

Figure 11:
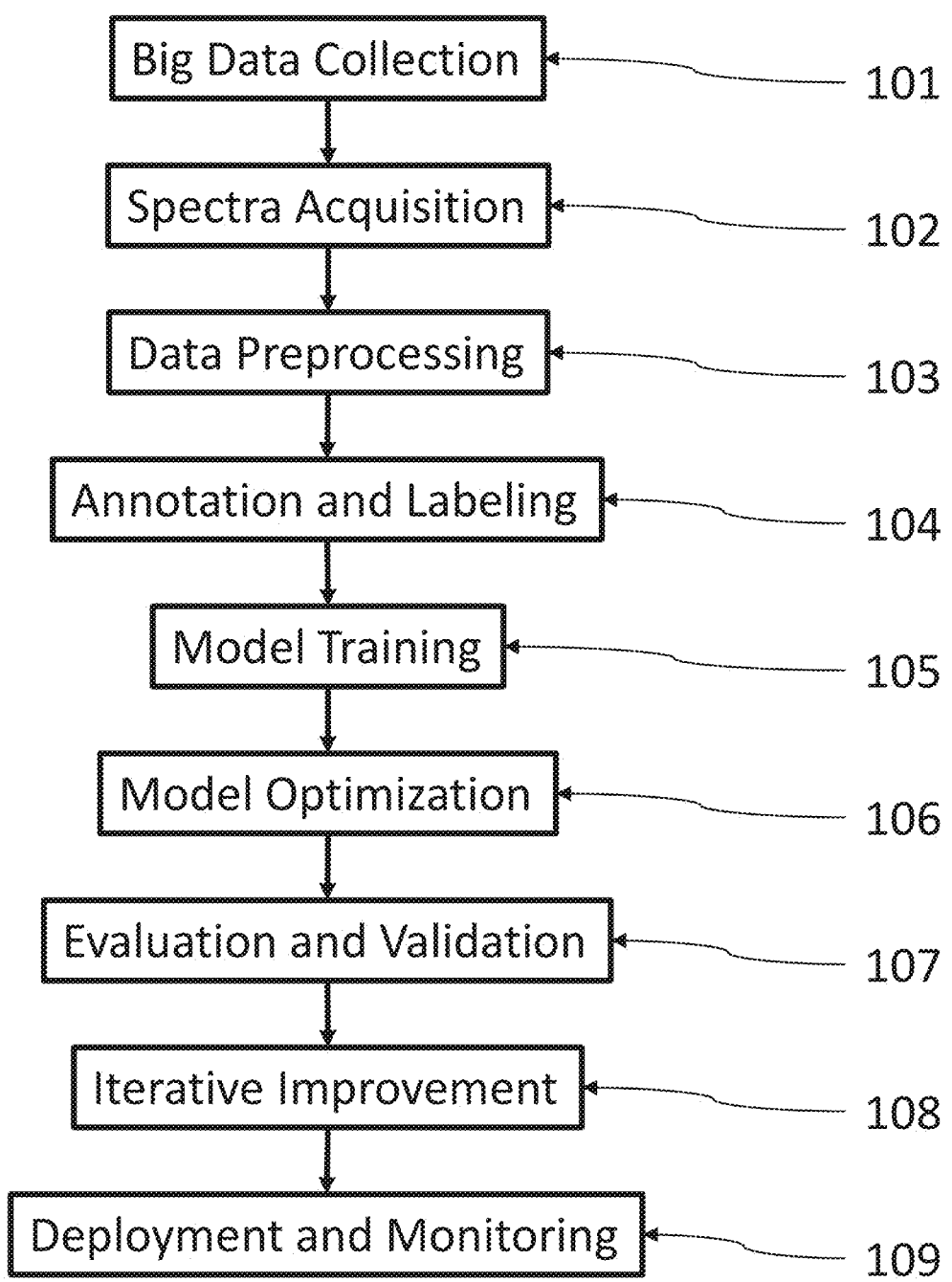
FIG. 11 presents a flow-chart illustrating the process of training an AI machine to identify a plurality of date rape drugs (DRDs) spectra that may be present or absent in a variety of beverages and deploy it once trained, some or all of the following steps should be employed, which include Big Data Collection step 111, Spectra Acquisition step 112, Data Preprocessing step 113, Annotation and Labeling step 114, Model Training step 115, Model Optimization step 116, Evaluation and Validation step 117, Iterative Improvement step 118, and Deployment and Monitoring step 119.

FIG. 11 presents a flow-chart illustrating the process of training an AI machine to identify a plurality of date rape drugs (DRDs) spectra that may be present or absent in a variety of beverages and deploy it once trained, some or all of the following steps should be employed, which include Big Data Collection step 111, Spectra Acquisition step 112, Data Preprocessing step 113, Annotation and Labeling step 114, Model Training step 115, Model Optimization step 116, Evaluation and Validation step 117, Iterative Improvement step 118, and Deployment and Monitoring step 119.

To execute the training and deployment of an AI system for DRD detection, specifically designed for deployment using a cellphone physically associated spectra meter and cloud-based AI communication, the system can be broken down into the following components and workflow:

1. Data Collection and Pre-Processing:

As explained above, extensively collect a diverse dataset of beverage samples ensuring a wide representation of positive and negative samples for DRDs. Employ a cellphone-integrated spectra meter to acquire spectra in a convenient and portable manner. Meticulously preprocess the acquired spectra, employing advanced techniques to remove any noise and artifacts that may affect subsequent analyses. Normalize the spectra to ensure consistency and align them if necessary, accounting for variations in resolution or wavelengths.

2. Cloud-Based AI Training:

Establish a robust cloud infrastructure capable of handling the large-scale dataset and intensive AI training processes. Implement cloud-based AI frameworks and tools to train the AI model on the collected dataset, leveraging the computational power and scalability of the cloud. Employ state-of-the-art deep learning algorithms and techniques to optimize the model's performance in identifying DRDs. Utilize iterative training cycles, adjusting hyperparameters, and refining the model architecture to enhance accuracy and robustness.

3. Communication Between Cellphone and Cloud:

Develop a dedicated mobile application that serves as a communication interface between the cellphone-carried spectrometer and the cloud-based AI system. Implement secure and efficient data transfer protocols, ensuring the privacy and integrity of the acquired spectra during transmission to the cloud. Enable seamless integration of the mobile application with the cloud infrastructure, allowing for seamless data flow and analysis.

4. AI Model Execution and Result Display:

Once the AI model is trained and deployed on the cloud server, the mobile application initiates the execution of the model for DRD analysis. The acquired spectra from the cellphone is securely transmitted to the cloud server for analysis using the trained AI model. The AI model processes the spectra, leveraging its learned patterns and correlations to determine the presence or absence of DRD(s) in the analyzed beverage sample. The results, indicating the presence or absence of DRD spectra, are transmitted back to the mobile application for display to the user in a clear and user-friendly format.

5. User Interface and Interaction:

Design an intuitive and user-friendly interface within the mobile application, ensuring ease of use and efficient interaction for users. Provide a seamless user experience, allowing users to initiate the analysis, monitor the progress, and receive timely updates on the analysis status. Implement real-time feedback or notifications to keep users informed about the analysis progress and completion. Display the analysis results in a comprehensive and easily interpretable manner, clearly indicating the presence or absence of DRD spectra in the analyzed beverage sample.

6. Continuous Improvement and Updates:

Establish a feedback loop with users and experts to gather insights, suggestions, and feedback on the system's performance and usability. Continuously monitor the AI model's performance and accuracy, identifying areas for improvement and refinement. Incorporate additional data and emerging techniques into the training process to enhance the system's accuracy and adaptability. Regularly update the mobile application and the cloud-based infrastructure, ensuring the system remains up to date with the latest advancements and user requirements.

This system, integrating a cellphone-carried spectra meter, cloud-based AI training, and a user-friendly mobile application, provides a comprehensive solution for DRD detection and identification in beverages. It combines the convenience and mobility of a cellphone physically associated spectra meter (e.g., DRD detection device 100 in FIG. 10) with the computational power and scalability of the cloud (e.g., remote server (cloud) 101 in FIG. 10), enabling accurate and efficient analysis. The continuous improvement and updates ensure the system remains effective, adaptable to evolving requirements, and aligned with user expectations.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

General Definitions:

As used herein the term "and/or" in context of a list of items refers to any one on them indecently of the other, and any combination of two or more of them, or any sub combination including any integer number of then less than all of them, or all of them.

As used herein the term "about" refers to ±10%. For example, the term "about 100 μm" encompasses the value 100 μm, as well as the values 90 μm μm 91 μm, 92 μm, 93 μm, 94 μm, 95 μm, 96 μm, 97 μm, 98 μm, 98 μm, 99 μm, 100 μm, 101 μm, 102 μm, 103 μm, 104 μm, 105 μm, 106 μm, 107 μm, 108 μm, 109 μm, and 110 μm.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the phrase "selected from the group consisting of" includes all members of the recited group, each member of the recited group, and all possible combinations. For example, selected from the group consisting of A, B, and C, includes A, only, as well as B, only, as well as C, only, as well as A and B, as well as A and C, as well as B and C, and as well as A, B, and C.

As used herein, the phrases "substantially devoid of" and/or "essentially devoid of" in the context of a certain substance, refer to a composition that is totally devoid of this substance or includes less than about 5, 1, 0.5 or 0.1 percent of the substance by total weight or volume of the composition. Alternatively, the phrases "substantially devoid of" and/or "essentially devoid of" in the context of a process, a method, a property or a characteristic, refer to a process, a composition, a structure or an article that is totally devoid of a certain process/method step, or a certain property or a certain characteristic, or a process/method wherein the certain process/method step is effected at less than about 5, 1, 0.5 or 0.1 percent compared to a given standard process/method, or property or a characteristic characterized by less than about 5, 1, 0.5 or 0.1 percent of the property or characteristic, compared to a given standard.

When applied to an original property, or a desired property, or an afforded property of an object or a composition, the term "substantially maintaining", as used herein, means that the property has not change by more than 20%, 10% or more than 5% in the processed object or composition.

The term "exemplary" is used herein to mean "serving as an example, instance or illustration". Any embodiment described as "exemplary" is not necessarily to be construed as preferred or advantageous over other embodiments and/or to exclude the incorporation of features from other embodiments. Thus, the use of the term "exemplary" means illustrative or by way of example, and any reference herein to "the invention" is not intended to restrict or limit the invention to the exact features or steps of any one or more of the exemplary embodiments disclosed in the present specification. Also, repeated use of the phrase "in one embodiment," "in an exemplary embodiment," or similar phrases do not necessarily refer to the same embodiment, although they may. It is also noted that terms like "preferably," "commonly," and "typically," are not used herein to limit the scope of the claimed invention or to imply that certain features are critical, essential, or even important to the structure or function of the claimed invention. Rather, those terms are merely intended to highlight alternative or additional features that may or may not be used in a particular embodiment of the present invention.

The words "optionally" or "alternatively" are used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the terms "process" and "method" refer to manners, means, techniques and procedures for accomplishing a given task including, but not limited to, those manners, means, techniques and procedures either known to, or readily developed from known manners, means, techniques and procedures by practitioners of the chemical, material, mechanical, computational and digital arts.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

It is expected that during the life of a patent maturing from this application many relevant cellphone-bound devices for detecting a date rape drug (DRD) will be developed and the scope of the phrase "cellphone-bound devices for detecting a date rape drug (DRD)" is intended to include all such new technologies a priori.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination or as suitable in any other described embodiment of the invention. Certain features described in the context of various embodiments are not to be considered essential features of those embodiments, unless the embodiment is inoperative without those elements.

Devices and methods for detecting at least one date rape drug (DRD) in at least one beverage in a social event are provided herein. An exemplary device may include a cellphone and/or a cellphone protective cover and/or a cellphone screen, front or back protective cover and/or a cellphone stylus and/or other cellphone add-on and/or any combination thereof. The device further comprises a DRD detection system for detecting the at least one DRD. The DRD detection system is operable by a laymen for DRD detection and is physically associated with the cellphone and/or the cellphone protective cover and/or the cellphone screen, front or back protective cover and/or the stylus and/or the other cellphone add-on and/or any combination thereof, such that day-to-day use and/or operation of any function of the cellphone and/or the cellphone protective cover and/or the cellphone screen, front or back protective cover and/or the stylus and/or the other cellphone add-on and/or any combination thereof is substantially not affected by the DRD detection system, thereby diminishing the ability, need and/or reducing a chance of removing the DRD detection system from the cellphone and/or the cellphone protective cover and/or the cellphone screen, front or back protective cover and/or the stylus and/or other cellphone add-on and/or any combination thereof, so as to allow instant use of the DRD detection system whenever required.

Various embodiments and aspects of the present invention as delineated hereinabove and as claimed in the claims section below find experimental support in the following examples.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A device for detecting at least one date rape drug (DRD) in at least one beverage in a social event, the device comprising a cellphone and a DRD detection system for detecting the at least one DRD, said DRD detection system being operable by a laymen for DRD detection and being physically associated with said cellphone, in a way such that the device is having a form-factor of a cellphone, and such that day-to-day use and/or operation of any function of said cellphone is substantially not affected by said DRD detection system, thereby diminishing the ability, need and/or reducing a chance of removing said DRD detection system from said cellphone, so as to allow instant use of said DRD detection system whenever required, wherein:

said DRD detection system comprises a spectra meter capable of acquiring a spectra of said beverage, communicating with a software and/or hardware of said cellphone and/or a remote location via said cellphone, and analyzing said spectra of said beverage for a presence or absence of said at least one DRD, and based on said analyzing, the device is configured to alert a user of the device to said presence or absence of said at least one DRD.

2. The device of claim 1, wherein said DRD detection system is physically associated in part with said cellphone and in part with a cellphone protective cover.

3. The device of claim 2, wherein said cellphone protective cover comprises said DRD detection system and said cellphone comprises said software.

4. The device of claim 1, wherein said spectra meter capable of acquiring said spectra is a spectrophotometer.

5. The device of claim 1, wherein said DRD detection system is designed for repeated uses.

6. The device of claim 1, wherein said DRD detection system is washable after use.

7. The device of claim 1, wherein the at least one DRD is selected from the group consisting of gamma-hydroxybutyrate (γ-hydroxybutyrate; GHB), gamma-butyrolactone (γ-butyrolactone; GBL), flunitrazepam (rohypnol), ketamine (Ketalar), methoxetamine (MXE), MDMA (Ecstasy), carisoprodol (Soma), a benzodiazepine, Diazepam, Alprazolam, Clonazepam, Lorazepam, Temazepam, Valium, Xanax, Klonopin, Ativan, Restoril, Normison, Temaze, Zolpidem, Zopiclone, a barbiturate, Phenobarbital, Secobarbital, Pentobarbital, Luminal, Seconal, Nembutal, phenobarbital, scopolamine, Hyoscine, morphine, heroin, fentanyl chloral hydrate, Aquachloral, Noctec, clonidine, Catapres, Kapvay, diphenhydramine, Benadryl, Nytol, and methamphetamine.

8. The device of claim 1, wherein each of said spectra meter and said software is independently integral in said cellphone.

9. The device of claim 8, wherein said DRD detection system and said software are designed to detect more than a single DRD, to alert a user of said cellphone of a presence or absence of said DRD and its chemical, common and/or street name or abbreviation.

10. The device of claim 8, wherein said software is housed in part in said cellphone and in part in said remote location.

11. The device of claim 1, wherein said software comprises an AI software pre-trained to identify a spectra of the at least one DRD in the beverage.

12. A method of detecting a presence or an absence of at least one DRD in a beverage comprising contacting said DRD detection system for detecting the at least one DRD of the device of claim 1 with the beverage and based on the performance of said DRD detection system detecting said presence or said absence of the at least one DRD in the beverage.

* * * * *